(12) United States Patent
Shekdar et al.

(10) Patent No.: US 8,945,848 B2
(45) Date of Patent: Feb. 3, 2015

(54) METHODS AND COMPOSITIONS FOR IDENTIFYING AND VALIDATING MODULATORS OF CELL FATE

(75) Inventors: Kambiz Shekdar, New York, NY (US); Dennis J. Sawchuk, Fanwood, NJ (US); Jessica C. Langer, Highland Park, NJ (US)

(73) Assignee: Chromocell Corporation, North Brunswick, NJ (US)

(*) Notice: Subject to any disclaimer, the term of this patent is extended or adjusted under 35 U.S.C. 154(b) by 217 days.

(21) Appl. No.: 13/387,962

(22) PCT Filed: Jul. 30, 2010

(86) PCT No.: PCT/US2010/043852
§ 371 (c)(1),
(2), (4) Date: Apr. 13, 2012

(87) PCT Pub. No.: WO2011/014740
PCT Pub. Date: Feb. 3, 2011

(65) Prior Publication Data
US 2012/0276572 A1   Nov. 1, 2012

Related U.S. Application Data

(60) Provisional application No. 61/230,581, filed on Jul. 31, 2009.

(51) Int. Cl.
| C12Q 1/68 | (2006.01) |
| G01N 33/50 | (2006.01) |
| C07H 21/00 | (2006.01) |
| C07H 21/02 | (2006.01) |
| C07H 21/04 | (2006.01) |
| C12N 15/00 | (2006.01) |

(52) U.S. Cl.
CPC .......... *G01N 33/5061* (2013.01); *C12Q 1/6897* (2013.01); *G01N 33/5073* (2013.01)
USPC ....... 435/6.13; 435/6.1; 435/6.11; 435/320.1; 435/440; 435/455; 536/22.1; 536/23.1; 536/24.1

(58) Field of Classification Search
None
See application file for complete search history.

(56) References Cited

U.S. PATENT DOCUMENTS

| 6,692,965 | B1 | 2/2004 | Shekdar et al. |
| 2003/0215798 | A1 | 11/2003 | Short et al. |
| 2006/0147937 | A1 | 7/2006 | Shekdar et al. |
| 2008/0220432 | A1 | 9/2008 | Sawchuk et al. |
| 2010/0212040 | A1 | 8/2010 | Shekdar et al. |
| 2010/0297674 | A1 | 11/2010 | Shekdar |
| 2010/0298167 | A1 | 11/2010 | Shekdar et al. |
| 2010/0311610 | A1 | 12/2010 | Shekdar |
| 2011/0003711 | A1 | 1/2011 | Shekdar et al. |
| 2011/0312533 | A1 | 12/2011 | Shekdar et al. |
| 2012/0015841 | A1 | 1/2012 | Shekdar et al. |
| 2012/0028278 | A1 | 2/2012 | Shekdar et al. |
| 2012/0058918 | A1 | 3/2012 | Shekdar et al. |
| 2012/0131701 | A1 | 5/2012 | Shekdar |

FOREIGN PATENT DOCUMENTS

| WO | WO 03/004626 A1 | 1/2003 |
| WO | WO 2005/005662 A2 | 1/2005 |
| WO | WO 2005/079462 A2 | 9/2005 |
| WO | WO 2005/118920 A2 | 12/2005 |
| WO | WO 2008/066909 A1 | 6/2008 |
| WO | WO 2009/094218 A2 | 7/2009 |
| WO | WO 2009/094610 A1 | 7/2009 |
| WO | WO 2009/100040 A2 | 8/2009 |
| WO | WO 2009/102569 A2 | 8/2009 |
| WO | WO 2010/087864 A1 | 8/2010 |
| WO | WO 2010/087997 A2 | 8/2010 |
| WO | WO 2010/088630 A2 | 8/2010 |
| WO | WO 2010/088633 A2 | 8/2010 |
| WO | WO 2011/014740 A2 | 2/2011 |
| WO | WO 2011/017288 A1 | 2/2011 |

OTHER PUBLICATIONS

Greco et al., "Functional Similarities Among Genes Regulated by Oct4 in Human Mesenchymal and Embryonic Stem Cells" 25 Stem Cells 3143-3154 (2007).*
Pasquet et al., "Transcription Enhancer Factor-1-dependent Expression of the a-Tropomyosin Gene in the Three Muscle Cell Types" 281(45) The Journal of Biological Chemistry 34406-34420 (2006).*
Chiter et al., "The production of a transgenic rat expressing nerwew growth fractor using cell-type specific keratin promoters" 26 Biochemical Society Transactions S144 (1998).*
Christensen et al., 2010, "Advances in imaging RNA in plants," *Trends Plant Sci*. 15(4):196-203.
International Search Report mailed Dec. 13, 2010 for International Patent Application No. PCT/US2010/044194, filed Aug. 3, 2010.
International Search Report mailed Mar. 17, 2011 for International Patent Application No. PCT/US2010/043852, filed Jul. 30, 2010.
Karrer et al., 1995, "In situ isolation of mRNA from individual plant cells: Creation of cell-specific cDNA libraries," *Proc. Natl. Acad. Sci.* 92:3814-3818.
Krause et al., 1997, "Regulation of CD34 expression in differentiating M1 cells," *Experimental Hematology* 25:1051-1061.
Li et al., 2008, "Molecular beacons: an optimal multifunctional biological probe," *Biochem. Biophys. Res. Commun*. 373(4):457-461.
Written Opinion of the International Searching Authority mailed Dec. 13, 2010 for International Patent Application No. PCT/US2010/044194, filed Aug. 3, 2010.
Written Opinion of the International Searching Authority mailed Mar. 17, 2011 for International Patent Application No. PCT/US2010/043852, filed Jul. 30, 2010.

* cited by examiner

*Primary Examiner* — Celine Qian
*Assistant Examiner* — Nancy J Leith
(74) *Attorney, Agent, or Firm* — Jones Day

(57) ABSTRACT

The invention provides for compositions and methods for identifying and validating modulators of cell fate, such as such as maintenance, cell specification, cell determination, induction of stem cell fate, cell differentiation, cell dedifferentiation, and cell trans-differentiation. The invention relates to reporter nucleic acid constructs, host cells comprising such constructs, and methods using such cells and constructs. The invention relates to methods for making cells comprising one or more reporter nucleic acid constructs using fluorogenic oligonucleotides. The methods relate to high throughput screens.

19 Claims, No Drawings

METHODS AND COMPOSITIONS FOR IDENTIFYING AND VALIDATING MODULATORS OF CELL FATE

This application claims priority benefit of U.S. provisional application No. 61/230,581, filed Jul. 31, 2009, which is incorporated herein by reference in its entirety.

1. INTRODUCTION

The invention relates to methods and compositions for identifying and validating modulators of cell fate, such as maintenance, cell specification, cell determination, induction of stem cell fate, cell differentiation, cell dedifferentiation, and cell trans-differentiation.

2. BACKGROUND

Cell-type specification that occurs during development and to some extend during adulthood of an animal depends on both quantitative and qualitative differences in gene expression (see, e.g., Lodish et al., *Molecular Cell Biology*, W.H. Freeman and Company, New York, N.Y., 2000). Certain genes are only expressed in a specific cell type or lineage and are important in cell-type specification. Genes involved in housekeeping tasks or in processes fundamental to all cell types generally are more ubiquitously expressed. Regulation of transcription is a widespread form of gene expression regulation involving interaction between transcription factors and co-factors with gene promoters and the basal transcriptional machinery. Genome or chromosomal remodeling may also contribute to transcriptional regulation.

Transcriptional regulation is an important process in regulating gene expression in stem cells, and plays a critical role in cell fate, i.e., cell specification, cell determination, and cell differentiation. Transcriptional control is maintained in embryonic stem cells ("ESCs") by several "key regulators"—transcription factors specifically expressed in ESCs but not expressed in differentiated tissues—which include Oct4, Sox2 and Nanog (see, e.g., Cole and Young, *Cold Spring Harb. Symp. Quant. Biol.*, 2008, 73:183-193). Oct4-Sox2 and Nanog work in concert with one another, and often are bound together to the promoter regions upstream from the same set of genes (see, e.g., Loh, Nat. Genetics, 2006, 38:413-440).

Oct4-Sox2 are specifically expressed in undifferentiated ESCs and form a stable heterodimer. Expression of Oct4 is necessary for the maintenance of stem cell pluripotency, and can serve as a stem cell marker. In the absence of Oct4, pluripotent stem cells revert to the trophoblast lineage.

The Oct4-Sox2 binding sites on promoters are typically adjacent to one another. Sox2 typically binds to a "Sox element" with the consensus sequence CATTGTA, and Oct 4 binds to an "Oct element" with the consensus sequence ATGCAAAA. These two motifs may be contiguous in the DNA sequence, and may be present in forward or reverse orientation.

The promoter region of Oct4 has been well characterized (GenBank Accession No. AP000509). The region encompasses −3917 to +55 basepair (bp) relative to the transcription start site (see, e.g., Nordhoff et al., *Mammalian Genome*, 2001, 12:309-317). The minimal promoter region is within the first 250 bps of the transcription start site, and enhancers and other regulatory elements, such as repressor elements, are further upstream. The full promoter region can drive tissue- and cell-specific expression of a reporter construct containing a gene of interest (see, e.g., Gerrard et al., *Stem Cells*, 2005; 23:124-133).

Nanog (GenBank Accession No. NT_009714, GenBank: AC006517) expression is driven by the Nanog promoter. This Nanog promoter region encompasses roughly 400 bp (−289 to +117 bp relative to the transcription start site) (see, e.g., Rodda et al., *J. Biol. Chem.*, 2005, 280(26):24731-24737). A region of roughly 200 bps within the Nanog promoter is highly conserved. This conserved region contains a "Sox element" (CATTGTA) and an "Oct element" (ATGCAAAA) adjacent to one another, both in reverse orientation. These elements are binding sites for the Sox2-Oct4 heterodimer.

This promoter region can be used to drive ESC-specific expression of a gene of interest. For example, addition of this promoter region upstream from an eGFP reporter drives expression patterns in ESCs that are identical to endogenous Nanog (see, e.g., Rodda et al., *J. Biol. Chem.*, 2005, 280(26): 24731-24737).

Stem cells are self-renewing cells that divide to give rise to daughter cells that can have an identical developmental potential and/or daughter cells with a more restricted (e.g., differentiated) developmental potential (see, e.g., Lodish et al., *Molecular Cell Biology*, W.H. Freeman and Company, New York, N.Y., 2000). Stem cells can also be found in small numbers in various tissues in the fetal and adult body. Stem cells can be obtained from other sources, for example, the umbilical cord of a newborn baby is a source of blood stem cells. Stem cells are described in terms of their potency—that is how many and how broad are the cell types they are capable of producing (see, e.g., Weiner et al., *Methods Mol. Biol.*, 2008, 438:3-8). Multipotent stem cells are capable of repopulating a defined tissue, whereas pluripotent stem cells are capable of giving rise to all three germ layers-endoderm, mesoderm and ectoderm (see, e.g., Smith et al., *J. Cell Physiol.*, 2009, 220(1):21-9). Pluripotent stem cells, such as ESCs, also have the capability of self-renewal. ESCs are derived from the inner cell mass of the blastocyst.

Recently it has been shown that expression of a cocktail of genes (i.e., c-Myc, Klf4, Oct4, and Sox2) known to be important in the maintenance of the stem cell state in ESCs, can reprogram mature or somatic cells to a cell indistinguishable from an ESC, which is termed an induced pluripotent stem (iPS) cell (see, e.g., Woltjen et al., (2009) *Nature*, 458:766-770). Both ESCs and iPS cells are capable of being maintained long term in a stem cell state in vitro. Both cell types when injected into mice, give rise to teratomas, tumors containing cells derived from all three germ layers.

In the adult, there are thought to be stem cells residing in each tissue that are capable of repopulating a defined tissue in the course of maintenance and repair (see, e.g., Pekovic et al., *J. Anat.*, 2008, 213(1):5-25). Hematopoietic stem cells (HSCs) reside in the bone marrow and are capable of giving rise to all the cells in the blood and bone marrow, including red blood cells, macrophages and other immune cells (see, e.g., Weissman I L, Annu Rev. Cell Dev. Biol., 2001, 17:387-403). A special type of HSC from blood and bone marrow called "side population" or "SP" is described as CD34−/low, c-Kit$^+$, and Sca-1$^+$ (see, e.g., Jackson et al., (2001) *J. Clin. Invest.*, 107(11): 1395-1402).

Other well defined adult stem cell populations include neural stem cells, intestinal stem cells, mesenchymal stem cells, endothelial stem cells, adipose stem cells, olfactory stem cells and skin stem cells. These cells reside in a well defined "niche" environment in vivo that plays a key role in maintaining the stem cell state. Ex vivo culture of adult stem cells usually results in the differentiation of these cells. When harvested from a donor and given to a recipient, these cells are able, under certain conditions, to engraft in the recipient and contribute to the mature tissue (see, e.g., Sensebé et al., *Transplantation*, 2009, 87(9 Suppl):S49-S53).

Currently there is a demand for a screening system for modulators of cell fate, wherein the screening system is suitable for high throughput screening. The present invention provides such a system.

3. SUMMARY

The invention provides for compositions and methods for identifying and validating modulators of cell fate. In particular, the invention provides for nucleic acid constructs and recombinant host cells for use in the methods described herein, as well as methods for making such recombinant host cells. The methods described herein allow for introduction of multiple genes required to achieve a cellular context that allows for screening of compound libraries to identify compounds that compensate for the activity of one or more genes that are required for modulating cell fate. This allows for identification of compounds which may act through novel or distinct pathways or mechanisms.

The nucleic acid constructs described herein comprise (a) an open reading frame (ORF) encoding a reporter wherein the ORF is operably linked to a cell type related ("CTR") promoter; and (b) one or more nucleic acid sequences encoding one or more target sequence RNAs ("TSRs"). The TSRs can be detected by fluorogenic oligonucleotides or molecular beacon probes, which may contain a fluorophore and a nucleic acid sequence complementary to a TSR (e.g., a nucleic acid sequence that can hybridize to a TSR), to identify individual recombinant host cells containing one or more nucleic acid constructs. The isolation of such recombinant host cells containing one or more desired nucleic acid constructs and the desired phenotype provides a robust and reliable cell-based system for use in identifying and validating modulators of cell fate/cell type specification.

In some embodiments, the invention described herein relates to a plurality of reporter nucleic acid constructs, wherein each one of the plurality of reporter nucleic acid constructs independently comprises an ORF encoding a reporter operably linked to a different CTR promoter and nucleic acid sequences encoding one or more TSRs operably linked to a promoter, e.g., a ubiquitous promoter. The same reporter may be used with multiple different CTR promoters.

The invention described herein provides several advantages. In one aspect, the use of fluorogenic oligonucleotides allows for less stringent selection processes (e.g., selection without the use of drugs) of recombinant host cells containing the reporter nucleic acid constructs. Without being bound by theory, this allows for the isolated recombinant host cells containing the reporter nucleic acid constructs (i) to be cultured and maintained over a long period of time, and/or (ii) to be utilized in physiologically more relevant screens.

The host cells can also be analyzed at the single cell level. The use of more than one target sequence can minimize false positives. Another advantage of the cell-based system described herein is the ability to streamline the process of isolating the recombinant host cells as well as the process of using such cells to identify and validate modulators of cell fate/cell type specification. Streamlining the process also allow for high throughput applications, which increases efficiency and volume. For example, in certain aspects, host cells for high throughput screening can be engineered to comprise multiple nucleic acid constructs for testing multiple different CTR promoters, wherein each one of the nucleic acid constructs comprise an ORF encoding the same reporter operably linked to a different CTR promoter of interest. The different CTR promoters of interest may be associated with one particular cell type. When host cells engineered to comprise these constructs are used in high throughput screens, compounds that activate the reporter can be identified. It may not be necessary initially to know which one of the different CTR promoters were activated to result in the detected reporter activity; however this would nonetheless result in identifying compounds that could activate at least one of the different CTR promoters. Further testing may be carried out and pursued if required to determine which one of the different CTR promoters were activated. Multiple groups of CTR promoters associated with different cell types may be tested, wherein each group of CTR promoters associated with a particular cell type drives transcription of a particular reporter.

In a particular aspect, it is desirable to isolate and to use recombinant host cells containing a reporter nucleic acid construct wherein the CTR promoter is not active or has low activity in the host cell. In specific embodiments, the activity of the CTR promoter is not above basal transcriptional activity. Basal transcriptional activity relates to transcription involving essentially the basal transcriptional machinery and the minimal promoter region, which generally includes a TATA box or initiator and adjacent nucleic acid sequences (e.g., about 10-100 bps) upstream of the transcription start site, and do not involve enhancers or repressors. In specific embodiments, the activity of the CTR promoter is not more than background activity. Such host cells may be useful for identifying and/or verifying modulators that can induce or increase the activity of the CTR promoter. However, the isolation and establishment of these host cells and cell lines that have the reporter nucleic acid construct, yet does not express the reporter (which is operably linked to the CTR promoter) or expresses the reporter at low levels comparable to background levels, using conventional methods known to one of skill in the art are time consuming, laborious, and difficult. For example, each putative cell would have to be activated, the activity of the reporter would be assessed for selection, and the activating signal would have to be removed after selection. The methods and compositions described herein provide better solutions for isolation and establishment of host cells and cell lines comprising reporter nucleic acid constructs, in part, by using fluorogenic oligonucleotides. In one aspect, the CTR promoter is flanked by two constitutively active promoter sequences driving the expression of two TSRs. The TSRs may be in the same or in the opposite orientation relative to the orientation of the CTR promoter and reporter. Expression of these TSR nucleotides can be detected using fluorogenic oligonucleotides (e.g., nucleotides that are complementary to, or that hybridize with the TSRs). In this way, host cells and cell lines expressing (preferably stably) the reporter nucleic acid constructs, independent of the activity of the CTR promoter, can be rapidly selected. In certain aspects, the invention provides for a reporter nucleic acid construct that comprises an untranslated target sequence encoding a TSR that is cotranscribed with the reporter as a marker for selection of cells wherein the CTR promoter is not active or is active at low levels, above background. In a particular embodiment, the untranslated target sequence is 3' to the ORF encoding the reporter that is operably linked to the CTR. For example, fluorogenic oligonucleotides complementary to the untranslated TSR that is cotranscribed with the reporter is introduced into the cells, and cells that do not transcribe this TSR or transcribe this TSR in low amounts are selected. For example, the fluorogenic oligonucleotides cannot detect the presence of TSR transcripts, or can only detect small amounts of TSR transcripts, in the cells.

In other embodiments, the CTR promoter is active in the host cell. Specifically, cells that have a strong signal using fluorogenic oligonucleotides to detect the untranslated TSR cotranscribed with the reporter are selected. Such selected host cells may be useful for identifying compounds that inhibit or decrease activity of the CTR promoter.

In a specific aspect, the invention provides for a nucleic acid construct comprising:
(a) an ORF encoding a reporter wherein the ORF is operably linked to a CTR promoter; and
(b) a nucleic acid sequence encoding a target sequence RNA1 ("TSR1"). The nucleic acid construct may further comprise a nucleic acid sequence encoding a target sequence RNA2 ("TSR2"). Such nucleic acid construct may further comprise a nucleic acid sequence encoding a target sequence RNA3 ("TSR3"), wherein TSR3 is cotranscribed with the reporter. In specific embodiments, the reporter is firefly luciferase. In other embodiments, the reporter is green fluorescent protein (GFP) or yellow fluorescent protein (YFP). In other embodiments, the reporter is a protease or an enzyme such as alkaline phosphatase.

The reporter nucleic acid constructs described herein allow for monitoring the activity of CTR promoters which may play a role in regulating gene expression of cell type related genes. The reporter nucleic acid constructs described herein also allow for monitoring the profile of activities of a group of CTR promoters associated with regulating expression of cell type related genes. In particular aspects that relate to identification and/or validation of modulators of stem cell fate, the CTR promoter of a reporter nucleic acid construct is a stem cell promoter. Such stem cell promoters may include, but are not limited to, the Oct4 promoter, Sox2 promoter, Klf4 promoter, c-myc promoter, LIN28 promoter, Nanog promoter, SSEA-3 promoter, and SSEA-4 promoter. For example, a reporter nucleic acid construct comprising a stem cell promoter may be introduced into a differentiated host cell wherein the stem cell promoter is not active (over the background) and various stimuli, agents and/or culture conditions may be tested for induction or enhancement of the activity of the stem cell promoter resulting from a change or transition in the cell fate of the host cell (e.g., dedifferentiation of the host cell). This may allow for identification of modulators and/or conditions that are capable of inducing or enhancing dedifferentiation. In similar aspects, the reporter nucleic acid construct comprising a stem cell promoter may be introduced into a stem cell wherein the stem cell promoter is active, and various stimuli and/or culture conditions may be tested for maintenance of the stem cell promoter activity so as to prevent differentiation.

In some aspects, the reporter nucleic acid construct comprising a cell type specific promoter may be introduced into a different cell type, wherein the cell type specific promoter is not active, and various stimuli and/or culture conditions may be tested for induction of the cell type specific promoter activity which is an indication of transdifferentiation. In particular embodiments, the CTR promoter of the reporter nucleic acid construct is a myocyte specific promoter. In some embodiments, the CTR promoter of the reporter nucleic acid construct is a retina cell specific promoter, a skin cell specific promoter, or a heart muscle cell promoter.

The invention also provides for a host cell comprising one or more reporter nucleic acid constructs described herein. In certain embodiments, the CTR promoter of the reporter nucleic acid construct is active above background levels in the host cell. In other embodiments, the CTR promoter of the reporter nucleic acid construct is not active above background levels in the cell. In one embodiment, the CTR promoter is a stem cell promoter that is active in the host cell. In another embodiment, the CTR promoter is a stem cell promoter that is not active above background levels in the host cell. In one embodiment, the CTR promoter is a myocyte specific promoter, a retina cell specific promoter, a skin cell specific promoter, or a heart muscle cell specific promoter that is active in the host cell. In another embodiment, the CTR promoter is a myocyte specific promoter, a retina cell specific promoter, a skin cell specific promoter, or a heart muscle cell specific promoter that is not active above background levels in the host cell. In specific embodiments, the host cell is a stable cell line. In some embodiments, a host cell contains one or more, or two or more different reporter nucleic acid constructs comprising different reporters respectively. In certain embodiments, a host cell contains two or more different reporter nucleic acid constructs, wherein each of the different reporter nucleic acid construct independently comprises an ORF encoding a reporter operably linked to a different CTR promoter. In particular embodiments, the cells may contain multiple different reporter nucleic acid constructs, wherein each of the different reporter nucleic acid construct encodes the same reporter, and each of the different reporter nucleic acid construct comprises a different CTR promoter that is operably linked to the reporter to regulate transcription of the reporter. In particular embodiments, the cells may contain multiple groups of different reporter nucleic acid constructs, wherein each group of the different reporter nucleic acid constructs encodes a different reporter, and wherein each different reporter is operably linked to a CTR promoter of a cell type of interest. For example, a host cell may comprise four different reporter nucleic acid constructs, wherein the first reporter nucleic acid construct comprises a first reporter operably linked to a first CTR promoter, the second reporter nucleic acid construct comprises a first reporter operably linked to a second CTR promoter, the third reporter nucleic acid construct comprises a second reporter operably linked to a third CTR promoter, and a fourth reporter nucleic acid construct comprises a second reporter operably linked to a fourth CTR promoter, wherein the first and second CTR promoters are associated with a first cell type, and the third and fourth CTR promoters are associated with a second cell type.

In specific embodiments, the host cell further comprises one or more recombinant nucleic acids encoding one or more CTR factors. The CTR factor may be a CTR factor that induces or enhances the activity of the CTR promoter in cooperation with other factors or modulators. In some embodiments, the CTR factor may be a CTR factor that inhibits or decreases the activity of the CTR promoter in cooperation with other factors or modulators. In certain embodiments, the CTR factor is involved in transcriptional regulation. In some embodiments, the CTR factor is involved in stem cell maintenance or proliferation, cell differentiation, cell dedifferentiation, or cell transdifferentiation. In certain embodiments, the CTR factor may be involved in methylation, acetylation or deacetylation, e.g., histone acetylation or deacetylation. In particular embodiments, the CTR factor may include, but is not limited to, Oct4, Sox2, Klf4, c-Myc, LIN28, Nanog, SSEA-3, and SSEA-4. In some embodiments, the CTR factor is an RNA (e.g., microRNA). The host cell may comprise recombinant nucleic acid construct(s) encoding one or more of such CTR factors. In particular embodiments, the host cell is isolated. In specific embodiments, the host cell comprises two or more different recombinant nucleic acid constructs encoding different CTR factors respectively. In certain aspects, a CTR factor is encoded by a reporter nucleic acid construct introduced into the host cell.

In specific aspects, the invention relates to a method for making a recombinant host cell comprising the steps of: (a) introducing into a host cell one or more reporter nucleic acid constructs described herein comprising one or more TSRs; (b) introducing into the host cell fluorogenic oligonucleotides that are complementary (or hybridize) to the TSRs; and (c) selecting cells that transcribe one or more TSRs, and do not transcribe other TSRs above background levels. In particular aspects, the invention relates to a method for making a recombinant host cell comprising the steps of: (a) introducing into a host cell a reporter nucleic acid construct described herein; (b) introducing into the host cell fluorogenic oligonucleotides that are complementary (or hybridize) to TSR1, TSR2, and TSR3; and (c) selecting cells that transcribe TSR1 and TSR2, and do not transcribe TSR3 above background levels. In specific embodiments, the fluorogenic oligonucleotide comprise a polynucleotide conjugated to a fluorescent molecule. In certain embodiments, fluorogenic oligonucleotides form stem-loop structures when not hybridized to the target sequence. In specific embodiments, the CTR promoter of the reporter nucleic acid construct is a stem cell promoter, such as the Oct4 promoter, Sox2 promoter, Klf4 promoter, c-myc promoter, LIN28 promoter, Nanog promoter, SSEA-3 promoter, and SSEA-4 promoter. In some embodiments, the CTR promoter of the reporter nucleic acid construct is a myocyte promoter, eye or retina cell promoter, skin cell promoter, hematopoietic cell promoter, or heart muscle cell promoter. In certain embodiments, CTR promoters include promoters, or fragments thereof, of genes or RNAs preferentially expressed in one or more specific cell types. In certain embodiments, the reporter is luciferase, autofluorescent protein such as GFP or YFP, a protease, or an enzyme such as alkaline phosphatase. In specific embodiments, the method described herein further comprises the step of introducing into the cell one or more recombinant nucleic acids encoding one or more CTR factors.

In specific embodiments, the invention relates to a method for making a recombinant host cell comprising the steps of: (a) introducing into a cell a reporter nucleic acid construct described herein; (b) introducing into the cell fluorogenic oligonucleotides that are complementary (or hybridize) to TSR1, TSR2, and TSR3; and (c) selecting cells that transcribe TSR1, TSR2, and TSR3. In specific embodiments, the CTR promoter of the reporter construct is a stem cell promoter, such as the Oct4 promoter, Sox2 promoter, Klf4 promoter, c-myc promoter, LIN28 promoter, Nanog promoter, SSEA-3 promoter, and SSEA-4 promoter. In specific embodiments, the method described herein further comprises the step of introducing into the cell one or more recombinant nucleic acids encoding one or more CTR factors. In particular embodiments, the host cell is a stable cell line. In specific embodiments, a host cell stably expresses RNAs or proteins of interests, e.g., reporter or CTR factor. In certain embodiments, a reporter nucleic acid construct described herein is stably integrated into the genome of a host cell.

In other aspects, the invention relates to a method for identifying a modulator of cell type (or cell fate) comprising the steps of: (a) contact a host cell containing a reporter nucleic acid construct described herein with a compound; and (b) determining the activity or expression level of the reporter; wherein the compound is a modulator of cell type if the expression level of the reporter is increased or decreased in the presence of the compound relative to the expression level of the report in the absence of the compound. In certain embodiments, the invention relates to a method for identifying a modulator of cell type or cell fate, such as cell maintenance, cell specification, cell determination, induction of stem cell fate, cell differentiation, cell dedifferentiation, or cell trans-differentiation. In specific embodiments, the CTR promoter of the reporter construct is a stem cell promoter, such as the Oct4 promoter, Sox2 promoter, Klf4 promoter, c-myc promoter, LIN28 promoter, Nanog promoter, SSEA-3 promoter, and SSEA-4 promoter. In certain embodiments, CTR promoters include promoters, or fragments thereof, of genes or RNAs preferentially expressed in one or more specific cell types. In specific embodiments, the method described herein further comprises the step of introducing into the cell a recombinant nucleic acid encoding a CTR factor. In certain embodiments, the reporter is luciferase, autofluorescent protein such as GFP or YFP, a protease, or an enzyme such as alkaline phosphatase.

In certain aspects, the invention relates to a method for identifying a positive modulator of cell type comprising the steps of: (a) contact a host cell containing a reporter nucleic acid construct described herein with a compound; and (b) determining the expression level of the reporter; wherein the compound is a positive modulator of cell type if the activity or expression level of the reporter is increased in the presence of the compound relative to the activity or expression level of the report in the absence of the compound. In specific embodiments, the CTR promoter of the reporter construct is a stem cell promoter, such as the Oct4 promoter, Sox2 promoter, Klf4 promoter, c-myc promoter, LIN28 promoter, Nanog promoter, SSEA-3 promoter, and SSEA-4 promoter. In specific embodiments, the method described herein further comprises the step of introducing into the cell a recombinant nucleic acid encoding a CTR factor (e.g., RNA or polypeptide).

In some aspects, the invention relates to a method for identifying a modulator of myocyte differentiation comprising the steps of: (a) contact a host cell comprising a reporter nucleic acid construct described herein with a compound; and (b) determining the activity or expression level of the reporter; wherein the compound is a modulator of myocyte differentiation if the activity or expression level of the reporter is increased or decreased in the presence of the compound relative to the expression level of the reporter in the absence of the compound.

In certain aspects, the invention relates to a method for identifying a positive modulator of myocyte differentiation comprising the steps of: (a) contact a host cell comprising a reporter nucleic acid construct described herein with a compound; and (b) determining the activity or expression level of the reporter; wherein the compound is a positive modulator of myocyte differentiation if the activity or expression level of the reporter is increased in the presence of the compound relative to the activity or expression level of the reporter in the absence of the compound. The host cell may comprise more than one different reporter nucleic acid constructs. Each of the different reporter nucleic acid constructs may comprise a different CTR promoter operably linked to an ORF encoding the same reporter. Each of the different reporter nucleic acid constructs may comprise a different CTR promoter operably linked to an ORF encoding different reporters. In specific embodiments, the host cells recombinantly express one or more CTR factors (e.g., RNA or polypeptide).

In other aspects, the invention relates to a method for identifying a modulator of a CTR promoter comprising the steps of: (a) contact a host cell containing a reporter nucleic acid construct described herein (e.g., a construct comprising an ORF encoding a reporter operably linked to a CTR promoter and sequences encoding one or more TSRs) with a compound; and (b) determining the activity or expression level of the reporter; wherein the compound is a modulator of the CTR promoter if the expression level of the reporter is increased or decreased in the presence of the compound relative to the expression level of the report in the absence of the compound. In specific embodiments, the CTR promoter of the reporter construct is a stem cell promoter, such as the Oct4 promoter, Sox2 promoter, Klf4 promoter, c-myc promoter, LIN28 promoter, Nanog promoter, SSEA-3 promoter, and SSEA-4 promoter. In certain embodiments, CTR promoters include promoters, or fragments thereof, of genes or RNAs preferentially expressed in one or more specific cell types. In specific embodiments, the method described herein further comprises the step of introducing into the cell a recombinant nucleic acid encoding a CTR factor. In certain embodiments, the reporter is luciferase, autofluorescent protein such as GFP or YFP, a protease, or an enzyme such as alkaline phosphatase.

In a further aspect of the present invention, differentiated, adult or specialized cells generated according to the methods described herein may be used to generate stem cells. The present invention also provides for methods of identifying compounds that can reprogram differentiated, adult or specialized cells to become stem cells. In some embodiments, cells described wherein the cell type or specification is a differentiated, adult or specialized cell may be dedifferentiated into stems cells including but not limited to multipotent stem cells, pluripotent stem cells, omnipotent stem cells, induced pluripotent stem (iPS) cells, embryonic stem cells, cancer stem cells, and organ or tissue specific stem cells. Stem cells generated from the cells described herein may be differentiated into one or more cells of a differentiated, adult, or specialized cell type or specification. Embryonic stem cells and iPS cells generated from the cells described herein may be used to produce a whole non-human organism, e.g., a mouse. Methods of producing mice using mouse embryonic stem cells are known to those skilled in the art (see, e.g., Ohta et al., *Biol Reprod.*, 79(3):486-92 (2008)). Methods of producing mice using iPS cells are known to those skilled in the art (see, e.g., Zhao et al., "iPS cells produce viable mice through tetraploid complementation," *Nature*, advance online publication 23 Jul. 2009).

In some embodiments, cells described herein wherein the cell type or specification is a differentiated, adult or specialized cell may be dedifferentiated into stems cells including but not limited to multipotent stem cells, pluripotent stem cells, omnipotent stem cells, iPS cells, embryonic stem cells, cancer stem cells, and organ or tissue specific stem cells, and the stem cells thus produced may be differentiated into one or more cells of a differentiated, adult, or specialized cell type or specification.

In some embodiments, cells described herein wherein the cell type or specification is a differentiated, adult or specialized cell may be dedifferentiated into embryonic stem cells or iPS cells, and the stem cells thus produced may be used to produce a whole non-human organism, e.g., a mouse.

In some embodiments, cells described herein wherein the cell type or specification is a differentiated, adult or specialized cell may be dedifferentiated into embryonic stem cells or iPS cells, and the stem cells thus produced may be used to produce a whole non-human organism, e.g., a mouse, wherein the cells in the non-human organism of the same cell type or specification comprise the same properties for which the cells described herein were selected, e.g., expression of a protein or RNA of interest.

In some embodiments, cells of a specialized cell or tissue type comprising an RNA or protein or a functional or physiological form of an RNA or protein may be used to produce an embryonic stem cell or iPS cell that may be used to produce a non-human organism, e.g., a mouse, wherein the cells or tissues of the non-human organism of the same type comprise the RNA or protein or the functional or physiological form of the RNA or protein. In some embodiments, the non-human organism thus produced comprises the RNA or protein of a different species. In some embodiments, the non-human organism is mouse and the RNA or protein is of a human origin. In some embodiments, the non-human organism thus produced comprises an in vitro correlate. In some embodiments, the non-human organism thus produced may be used in testing, including preclinical testing. In some embodiments, the testing or preclinical testing is used to predict the activity of test compounds in humans.

In specific aspects, the invention provides for modulators identified from the methods described herein. Such modulators may be useful, alone or in combination, in therapies for treating conditions where tissue rejuvenation or regeneration may be beneficial, e.g., spinal cord injury, Parkinson's disease, macular degeneration, and diabetes. Modulators identified by the methods described herein may also be useful for tissue engineering to generate tissue or organs for transplantation, or to expand cells (e.g., HSCs) isolated from a patient ex vivo for subsequent transplantation back into the patient or into another patient. In certain aspects, modulators of cancer stem cells may be useful, alone or in combination, as therapies for treating cancer or preventing cancer recurrence.

In certain embodiments, a modulator identified from the methods described herein may specifically bind to a CTR promoter, or a region thereof such as an enhancer or repressor region and increase or enhance or decrease or inhibit transcription. In other embodiments, the modulator may specifically interact with a protein or polypeptide. Such protein or polypeptide may be a transcription factor, a signaling molecule, an enzyme or a protease. In specific embodiments, the modulator is an agonist. In other embodiments, the modulator is an antagonist.

The invention also relates to kits comprising one or more containers, each comprising one or more compositions described herein, e.g., recombinant host cells described herein. Such kits may also comprise one or more containers comprising one or more nucleic acid constructs described herein; and one or more fluorogenic oligonucleotides. The kits may also comprise one or more CTR factors or nucleic acid constructs encoding the CTR factors.

4. DETAILED DESCRIPTION

Described herein are compositions and methods for identifying and validating modulators of cell fate such as maintenance, cell specification, cell determination, induction of stem cell fate, cell differentiation, cell dedifferentiation, and cell trans-differentiation. The invention provides for reporter nucleic acid constructs, recombinant host cells comprising such constructs, and modulators of cell fate identified by the methods described herein. The methods described herein include high throughput screens.

In some aspects, the methods described herein are for making host cells comprising one or more reporter nucleic acid constructs, each comprising (i) an ORF encoding a reporter, wherein the ORF is operably linked to a CTR promoter, and (ii) one or more nucleic acid sequence encoding one or more TSRs. Such method comprises (a) introducing into a host cell one or more reporter nucleic acid constructs described herein comprising one or more TSRs; (b) introducing into the host cell fluorogenic oligonucleotides that are capable of detecting the TSRs; and (c) selecting cells that transcribe one or more TSRs above background levels. In certain embodiments, step (c) involves selecting cells that do not transcribe one or more TSRs above background levels. In specific embodiments, step (c) involves selecting cells that transcribe one or more TSRs whose transcription are independent from the CTR promoter (e.g., whose transcription are regulated by a constitutive promoter that is not the CTR promoter), and that do not transcribe one or more TSRs which are cotranscribed with the reporter (e.g., transcription of the TSR is regulated by the CTR promoter). In other embodiments, step (c) involves selecting cells that transcribe one or more TSRs whose transcription are independent from the CTR promoter, and that transcribe one or more TSRs cotranscribed with the reporter. The TSRs are used to identify host cells that contain one or more reporter nucleic acid constructs. In specific embodiments, the TSRs are used to identify host cells that contain one or more reporter nucleic acid constructs integrated into the genome in such a manner that the insertion sites do not affect transcription of the reporter (e.g., transcription of the reporter is not upregulated due to the insertion sites).

In certain embodiments, a reporter nucleic acid construct is stably integrated in the genome of a host cell. Stable integration can be tested by the presence of one or more TSRs in the host cell line over multiple cell passages. In other embodiments, a reporter nucleic acid construct is transiently introduced into the host cells. In such case, the host cells lose the reporter nucleic acid construct after several rounds of passages.

In certain embodiments, a reporter nucleic acid construct has at least two TSRs, wherein one or more TSR is under control of a promoter that is or can be active in the host cell, such as a constitutively active promoter, and a different TSR is cotranscribed with the reporter, i.e., the TSR is also under transcriptional control of the CTR promoter.

In certain embodiments, provided herein is a screening system for activators of a CTR promoter. To establish such a system, a reporter nucleic acid construct is introduced into host cells, e.g., via transfection, and subsequently host cells that are positive for TSRs transcriptionally regulated by a constitutive promoter but negative for TSRs co-transcribed with a reporter, i.e., transcriptionally regulated by a CTR promoter, are selected. Such selected host cells comprise a reporter nucleic acid construct, but the CTR promoter is inactive or active at low or basal levels, relative to background activity (e.g., background activity in negative control cells). Such selected host cells can then be contacted with compounds to identify compounds that upregulate the activity or expression level of the CTR promoter. Compounds that upregulate the CTR promoter are predicted to be inducers of the cell type in which the CTR promoter is active.

In certain embodiments, provided herein is a screening system for inhibitors of a CTR promoter. Such a system can be established by introducing one or more reporter nucleic acid constructs into host cells, and subsequently host cells that are positive for transcription of TSRs controlled by a constitutive promoter or a CTR promoter. Such selected host cells comprise the reporter nucleic acid construct, and the CTR promoter is active in the host cells. Such host cells can then be contacted with compounds to identify compounds that downregulate the activity or expression level of the CTR promoter. Compounds that downregulate the CTR promoter are predicted to be inhibitors of the cell type in which the CTR promoter is active.

Screening systems may also be established for one or more groups of different CTR promoters transcriptionally regulating expression of the same reporter. In this system, the activity or expression of a reporter correlates with the activity of a group of different CTR promoters. The different CTR promoters may be associated to a particular cell type. Thus, the screens may be carried out to identify modulators of any one of the different CTR promoters of interest. It may not be necessary initially to know which one of the different CTR promoters were activated to result in the detected reporter activity; however this would nonetheless result in identifying compounds that could activate at least one of the different CTR promoters. Further testing may be carried out and pursued if required to determine which one of the different CTR promoters were activated. For example, cells used in this system comprise three reporter nucleic acid constructs, wherein each reporter nucleic acid construct comprises an ORF of the same reporter operably linked to one of three different CTR promoters, such as the Nanog promoter, Oct4 promoter, and c-myc promoter. Multiple groups of CTR promoters may also be used, wherein each group comprises a different reporter. For example, a first group of CTR promoters transcriptionally regulate a first reporter, and a second group of CTR promoters transcriptionally regulate a second reporter.

In particular aspects, the present invention relates to Screening methods and systems for identifying and/or validating compounds that are modulators of cell fate, such as maintenance, cell specification, cell determination, induction of stem cell fate, cell differentiation, cell dedifferentiation, and cell trans-differentiation. The methods and screening systems described herein utilizes hosts cells comprising reporter nucleic acid constructs, which allow for introduction of multiple CTR factors (e.g., RNAs and polypeptides) that may cooperate with the screened compounds to modulate cell fate. In specific embodiments, the methods described herein provide for identifying and validating compounds that are capable of reprogramming differentiated, adult or specialized cells to generate stem cells (e.g., multipotent stem cells, pluripotent stem cells, omnipotent stem cells, iPS cells, embryonic stem cells, cancer stem cells, and organ or tissue specific stem cells). In other aspects, the methods described herein provide for identifying and validating compounds that are capable of reprogramming stem cells generated from the methods described herein to differentiate into one or more cells of a differentiated, adult, or specialized cell type or specification. Embryonic stem cells and iPS cells generated from the cells and methods described herein may be used to produce a whole non-human organism, e.g., a mouse.

The invention provides for many variations on the methods and compositions described herein. Discussed in more detail in the sections below are further non-limiting embodiments of the present invention, e.g., the reporter nucleic acid constructs can encode three or more TSRs, cells with intermediate activity of the CTR promoter can also be used with the methods described herein, cells that can be used with the screening methods disclosed herein can also be engineered to express additional factors that are important in cell fate regulation.

4.1 Reporter Nucleic Acid Constructs

Provided herein is a reporter nucleic acid construct comprising: (a) an ORF encoding a reporter wherein the ORF is operably linked to a CTR promoter; and (b) a nucleic acid sequence encoding a TSR, e.g., TSR1. The nucleic acid construct may further comprise a nucleic acid sequence encoding a second TSR, TSR2. In certain embodiments, TSR2 is cotranscribed with the reporter. In other embodiments, TSR2 is transcribed independently from the reporter. In specific embodiments, a reporter nucleic acid construct comprises TSR1 and TSR2, wherein TSR1 is transcribed independently from the reporter, and TSR2 is cotranscribed with the reporter. In certain embodiments, the nucleic acid construct may further comprise a nucleic acid sequence encoding a third TSR, TSR3, wherein the TSR3 is cotranscribed with the reporter. In other embodiments, TSR3 is transcribed independently from the reporter. In certain embodiments, the reporter nucleic acid construct may comprise nucleic acid sequences encoding four or more TSRs (e.g., TSR4, TSR5, TSR6, etc.). The TSRs (e.g., TSR1, TSR2, TSR3, etc.) are capable of hybridizing to fluorogenic oligonucleotides which have sequences that are complementary to the TSRs, respectively, and wherein the fluorogenic properties of the fluorogenic oligonucleotides change upon hybridization to a TSR. Hybridization may occur when the nucleic acid sequences of the TSR and the fluorogenic oligonucleotide are 100% complementary, or less than 100% complementary. As used herein, "complementary" refers to two nucleic acid sequences or strands that can form a based-pair double helix with each other. In specific embodiments, hybridization can occur when the nucleic acid sequences of the TSR and the fluorogenic oligonucleotide are at least about 99%, 98%, 97%, 96%, 95%, 94%, 93%, 92%, 91%, 90%, 85%, 80%, 75%, 70%, 65%, or 65% complementary, or any percentage complementary in between. In specific embodiments, at most 1, 2, 3, 4, 5, 6, 7, 8, 9, 10, 15, or 20 nucleic acid(s) of a TSR do(es) not form a base-pair with a nucleic acid(s) of a fluorogenic oligonucleotide. As used herein "hybridize" or "hybridization" refers to the association, non-covalently, of two nucleic acid strands to form double-stranded molecules based on Watson-Crick pairing (i.e., A-T/U and G-C pairing), such as two DNA strands, two RNA strands, or one RNA and one DNA strands. In specific embodiments, a TSR is capable of hybridizing to a stem-loop fluorogenic oligonucleotide.

In certain embodiments, a TSR is at most 10 nucleotides, 15 nucleotides, 20 nucleotides, 25 nucleotides, 30 nucleotides, 35 nucleotides, 40 nucleotides, 45 nucleotides, 50 nucleotides, 55 nucleotides, 60 nucleotides, 65 nucleotides, 70 nucleotides, 75 nucleotides, 80 nucleotides, 85 nucleotides, 90 nucleotides, 95 nucleotides, or 100 nucleotides in length.

In some embodiments, a TSR does not comprise a transcription termination signal or sequence. In other embodiments, a TSR is not a UTR (e.g., 5' UTR or 3' UTR). In other embodiments, a TSR is not translated. In some embodiments, a TSR is not a coding region of a gene. In particular embodiments, a TSR is not a native sequence of the genome (e.g., genome of a human, mouse, rat, monkey, dog, cat, pig, sheep, goat, horse, chicken, frog, worm, insect (e.g., fly), or cow).

In particular embodiments, a reporter nucleic acid construct comprises two ORFs, encoding two different reporters (e.g., reporter 1 and reporter 2), respectively, wherein each ORF is operably linked to different CTR promoters (e.g., CTR promoter 1 and CTR promoter 2). The reporter nucleic acid construct further comprises two TSRs which are cotranscribed with each of the different reporters respectively. In certain embodiments, a reporter nucleic acid construct comprises two ORFs, encoding the same reporter, wherein each ORF is operably linked to a different CTR promoter (e.g., CTR promoter 1 and CTR promoter 2). In specific embodiments, the distance between elements (e.g., ORFs or nucleic acid sequences encoding TSRs) in the reporter nucleic acid construct may be between about 1-100 nucleotides, about 100-300 nucleotides, about 100-500 nucleotides, 500-1,000 nucleotides, 1,000-2,000 nucleotides, 1,000-3,000 nucleotides, 1,000-5,000 nucleotides, 5,000-10,000 nucleotides, or 5,000-15,000 nucleotides.

In particular embodiments, a reporter nucleic acid construct may also comprise nucleic acid sequences encoding an RNA or a CTR factor, which may play a role in modulating the activity of the CTR promoter. The nucleic acid sequences encoding an RNA or a CTR factor may be operably linked to an inducible promoter or a constitutive or ubiquitous promoter.

In other embodiments, a host cell may comprise two or more reporter nucleic acid constructs, wherein a first reporter nucleic acid construct comprises an ORF encoding a first reporter which is operably linked to a first CTR promoter, and nucleic acid sequences encoding one or more TSRs, wherein one of said one or more TSRs is cotranscribed with the first reporter, wherein a second reporter nucleic acid construct comprises an ORF encoding a second reporter (different from the first reporter) operably linked to a second CTR promoter, and nucleic acid sequences encoding one or more TSRs, and wherein one of said one or more TSRs of the second reporter nucleic acid construct is cotranscribed with the second reporter.

In other embodiments, a host cell may comprise two or more different reporter nucleic acid constructs, wherein each of the different reporter nucleic acid constructs comprises an ORF of a reporter operably linked to a different CTR promoter, and nucleic acid sequences encoding one or more TSRs, wherein one of said one or more TSRs is cotranscribed with the reporter. When host cells engineered to comprise these constructs are used in high throughput screens, compounds that activate the reporter can be identified. It may not be necessary initially to know which one of the different CTR promoters were activated to result in the detected reporter activity; however this would nonetheless result in identifying compounds that could activate at least one of the different CTR promoters. Further testing may be carried out and pursued if required to determine which one of the different CTR promoters were activated.

Nucleic acid constructs described herein may be any construct known in the art. Nucleic acid constructs generally refer to a recombinantly or synthetically generated polynucleotide containing elements that permit expression of a particular coding sequence in a host cell. Nucleic acid constructs may include, but are not limited to, cosmids, plasmids, vectors, and viral vectors. Nucleic acid constructs may be used for introduction of nucleic acids into a cell transiently or stably (e.g., stable integration into the genome of a host cell).

4.1.1. Reporter Genes

The reporter nucleic acid constructs described herein may comprise an ORF encoding any reporter, which is operably linked to a CTR promoter. The activity, signal, or expression of the reporter may serve as a marker for the activity of the CTR promoter in a specific cellular context. The activity, signal, or expression of the reporter also may serve as a marker of a particular cell type or cellular context. In specific embodiments, the change in activity, signal, or expression level of the reporter in the presence and absence of a compound or in different culture conditions is detectable.

In a specific embodiment, the reporter is firefly Luciferase, or a variant thereof. Other non-limiting examples of reporters include autofluorescent proteins such as green fluorescent protein (GFP), red fluorescent protein (RFP), blue fluorescent protein (BFP), or yellow fluorescent protein (YFP). In specific embodiments, the reporter is a mutated variant of and autofluorescent protein such as GFP that has different excitation/emission spectra than the wild-type autofluorescent protein. Other non-limiting examples of reporters may include chloramphenicol acetyltransferase (CAT) and β-galactosidase.

In certain embodiments, a reporter may be a cell-surface localized protein or peptide that may be detected using fluorescently labeled antibody reagents or other labeled reagents that bind to the protein or peptide.

In some embodiments, a reporter may be an enzyme (e.g. alkaline phosphatase) that catalyzes or converts substrates into detectable products (e.g., fluorescent products).

In some embodiments, a reporter may be a protease that catalyzes reactions that result in a detectable signal or affect. For example, a cell may comprise a GFP-fusion protein that is cytosolic and that comprises an amino acid sequence that may be cleaved by a protease, and upon cleavage, the portion of the fusion protein comprising the fluorescent label may be, for instance, designed to be secreted, degraded or translocated (e.g. into the nucleus). Thus, a reporter can therefore include a protease that acts on such a substrate.

In other embodiments, reporters may also include enzymes that when expressed, result in a detectable change in the cell or the production of a detectable reagent. The detectable change in the cell may be a morphological change, biological, or chemical change.

In certain embodiments, the reporter nucleic acid construct comprises an ORF encoding a variant or a fragment of a reporter. In some embodiments, the reporter nucleic acid construct comprises an ORF encoding a modified version of the reporter that has improved expression, detection signal or stability. In some embodiments, the report variants are allelic variants, splice variants, truncated forms, isoforms, chimeric subunits and mutated forms that comprise amino acid substitutions (conservative or non-conservative), modified amino acids including chemically modified amino acids, and non-naturally occurring amino acids.

In some embodiments, the reporter nucleic acid construct comprises an ORF encoding a reporter that has one, two, three, four, five, six, seven, eight, nine, ten, fifteen, twenty, or more conservative mutations. In certain embodiments, the reporter nucleic acid construct comprises an ORF encoding a reporter that has less than three, four, five, six, seven, eight, nine, ten, fifteen, twenty, thirty, forty, or fifty conservative mutations.

"Conservative mutations" of a nucleic acid sequence refers to those nucleotides that encode identical or essentially identical amino acid sequences, or where the nucleotide does not encode an amino acid sequence, to essentially identical sequences. This is based on the fact that the genetic code is "degenerate," that is to say a number of distinct nucleic acids encode for the same amino acid. For instance, the codons GTT, GTA, GTC, and GTG all encode the amino acid valine. Thus, at every position where a valine is specified by a codon, the codon can be altered to any of the corresponding codons described without altering the encoded polypeptide. Such nucleic acid variations are "silent mutations," which are one species of "conservative mutation." Unless otherwise described every nucleotide sequence described herein which encodes an amino acid also includes every possible silent variation. One of ordinary skill will recognize that each codon in a nucleic acid (except ATG, which is ordinarily the only codon for methionine) can be modified to yield a functionally identical molecule by standard techniques. Accordingly, in each instance where mutagenesis is used each "silent mutation" of a nucleic acid, which encodes an amino acid, is implicitly included.

Furthermore, one of ordinary skill will recognize that "conservative mutations" also include the substitution, deletion or addition of nucleic acids that alter, add or delete a single amino acid or a small number of amino acids in a coding sequence where the nucleic acid alterations result in the substitution of a chemically similar amino acid. Amino acids that may serve as conservative substitutions for each other include the following: Basic: Arginine (R), Lysine (K), Histidine (H); Acidic: Aspartic acid (D), Glutamic acid (E), Asparagine (N), Glutamine (Q); hydrophilic: Glycine (G), Alanine (A), Valine (V), Leucine (L), Isoleucine (I); Hydrophobic: Phenylalanine (F), Tyrosine (Y), Tryptophan (W); Sulfur-containing: Methionine (M), Cysteine (C).

In particular embodiments, the reporter nucleic acid construct comprises an ORF encoding a reporter, wherein the ORF is codon optimized. Codon optimization allows for substitutions of nucleotides within the framework of the genetic code that do not alter the translated amino acid residue, but can enhance the stability and/or level of expression in a specific species. In particular embodiments, condon usage can be optimized for efficient and stable expression in a specific species such as humans.

The reporter may optionally comprise a tag, such as a His-tag or a FLAG-tag, which is translated with the reporter. Other non-limiting examples of a tag include a myc tag, a hemagglutinin (HA) tag, protein C, vesicular stomatitis virus (VSV)-G, FLU, BCCP, maltose binding protein tag, Nus-tag, Softag-1, Softag-2, Strep-tag, S-tag, thioredoxin, GST, V5, TAP or CBP. A tag may be used as a marker to determine protein expression levels, intracellular localization, protein-protein interactions, regulation of the protein of interest, or the protein's function. Tags may also be used to purify or fractionate proteins. Tags may comprise one or more protease sequences that are sensitive to protease cleavage. In specific embodiments, the reporter does not comprise a tag.

Methods for detecting the activity, signal, and expression levels of reporters are known to one skilled in the art. Non-limiting examples of such methods are discussed in further detail in the sections below. For example, luciferase activity may be detected via bioluminescent assays, autofluorescent proteins may be detected via microscopy or flow cytometry, and enzymes and protease may be detected in suitable assays with the appropriate substrates. Proteins of the reporters may be detected using for example, enzyme-linked immunosorbent assays (ELISAs) or immunoblots. Transcripts of reporter may be detected by, e.g., Northern blots, reverse transcriptase polymerase chain reaction (RT-PCR), real time PCR, quantitative PCR, or microarray analysis. Proper controls to determine the activity, signal, or expression level of reporter over background or noise are readily available to one skilled in the art. In certain embodiments, a reporter is active if its activity is higher than background activity in a control sample, and a reporter is considered not active if its activity is lower or equal to the background activity in a control sample. I 4.1.2. CTR Promoters Driving Transcription of the Reporter Generally, a promoter includes reference to a region of DNA upstream from the transcription start site involved in recruiting and binding of RNA polymerase and other proteins to initiate transcription and to regulate transcription. The reporter nucleic acid constructs described herein may comprise any CTR promoter. A CTR promoter regulates transcription of a CTR gene. As used herein, a CTR gene encodes a protein or polypeptide which has a function in cell fate, such as maintenance, cell specification, cell determination, induction of stem cell fate, cell differentiation, cell dedifferentiation, and/or cell trans-differentiation. As used herein, a CTR gene may be a cell-type specific gene or cell-type associated gene. A cell-type specific gene refers to a gene that is predominantly expressed in one specific cell type or a few specific cell types, and not in other cell types. In some embodiments, a cell-type specific gene refers to a gene that is exclusively expressed in a specific cell type. As used herein, a cell-type associated gene refers to a gene that is expressed at higher levels in one specific cell type or some specific cell types than in other cell types. In certain embodiments, a cell-type associated gene is expressed in several similar cell types (e.g., cells from a tissue, organ, or lineage) and is not expressed, or expressed in low levels, in other cell types (e.g., cells from other tissues, organs, or lineages). Cell-type specific and cell-type associated genes, alone or in combination, may serve as markers for a specific cell type. In combination, an expression profile of cell-type specific and cell-type associated genes, including ratios, may correlate with a particular cell type, and may serve as markers for that particular cell type. In specific embodiments, a CTR promoter regulates transcription of a cell-type specific gene. In certain embodiments, a CTR promoter regulates transcription of a cell-type associated gene. Unless otherwise stated, a CTR promoter refers to a promoter that regulates transcription of a CTR gene which can be either a cell-type specific gene or a cell-type associated gene. For example, a stem cell promoter refers to a promoter that regulates transcription of a stem cell specific gene or a stem cell associated gene. In certain embodiments, CTR promoters include promoters, or fragments thereof, of genes or RNAs (including microRNAs (miRNAs), small interfering RNAs (siRNAs), or RNAs that mediate RNA interference (RNAi)) preferentially expressed in one or more specific cell types.

In certain aspects where multiple reporter nucleic acid constructs are used, a pattern/profile of the level of activity of the different CTR promoters relative to each other correlates with a profile of CTR gene expression that is representative of a particular cell type. In such cases, whether a CTR promoter is active or inactive is not as representative of a particular cell type, as the pattern/profile collectively of the level of activity of the different CTR promoters relative to each other. For example, the pattern/profile of CTR gene expression of a stem cell is different than that of a myocyte. In certain embodiments, the pattern or profile of CTR gene expression representative of a particular cell type may be determined from microarray analysis, so that an appropriate pattern/profile is selected as the baseline pattern/profile of interest for the methods described herein. In other embodiments, microarray analysis may be performed subsequent to the methods described herein to confirm the pattern or profile of CTR gene expression representative of a particular cell type.

A CTR promoter comprises an element or region of a promoter which is necessary for transcription in a cell type of interest, wherein the element or region can be determined by any technique known in the art to a skilled artisan. In specific embodiments, a CTR promoter is a promoter involved in cell fate, such as maintenance, cell specification, cell determination, induction of stem cell fate, cell differentiation, cell dedifferentiation, or cell trans-differentiation.

In specific embodiments, the CTR promoter of a reporter nucleic acid construct comprises the minimal promoter element of a CTR gene or one or more promoter elements of a CTR gene, wherein these elements contribute to transcriptional regulation of CTR genes to confer cell type specificity. The promoter element can be an enhancer or a repressor. CTR promoters may also include enhancer and repressor elements upstream of the transcription initiation start site that contribute to transcriptional regulation conferring cell type specificity. Generally, the minimal promoter refers to nucleotides, which includes the transcription start site and nearby nucleotides of a promoter sequence, that are required for basal transcription involving the transcription-initiation complexes, which include RNA polymerase II ("Pol II") and general transcription factors. General transcription factors are initiation factors which position Pol II at transcription-initiation sites, and are thought to be required for transcription of most genes that are transcribed by Pol II. The transcription-initiation complexes bind to promoters and initiate transcription.

Many minimal promoters may contain a "TATA box" sequence (e.g., TATAAA in eukaryotes or some variation of that sequence) and other sequences that are required for transcription. In general, TATA boxes can be found approximately 25-35 bps upstream of the transcription start site. Some promoters do not contain a TATA box, and TATA-less transcription involves a multisubunit complex comprising TBP and TBP-associated factors (TAFs). Some promoters comprise an initiator instead of a TATA box. In general, many initiator elements have a cytosine at the −1 position and an adenine residue at the transcription start site (+1), and have the consensus sequence from 5' to 3': YYAN(T/A)YYY, where A is at the +1 position, Y is either C or T, (T/A) is T or A at position +3, and N is any of the four bases (see Lodish et al., *Molecular Cell Biology*, W.H. Freeman and Company, New York, N.Y., 2000, at page 365-266). In some embodiments, the CTR promoter comprises a promoter comprising a TATA box. In other embodiments, the CTR promoter comprises a promoter that does not comprise a TATA box. In certain embodiments, the CTR promoter comprises an initiator element. In certain embodiments, the CTR promoter does not comprise an initiator element. In specific embodiments, the CTR promoter comprises one or more enhancer regions from a CTR gene promoter. In particular embodiments, the CTR promoter comprises one or more (consensus) transcription factor binding sites. In certain embodiments, the CTR promoter does not comprise any repressor region, which recruits repressors that inhibit or decrease promoter activity. In specific embodiments, the CTR promoter comprises one or more repressor regions. In specific embodiments, the CTR promoter lacks one or more repressor regions of a CTR gene. In some embodiments, a region of a CTR promoter functions as an enhancer region in a particular cell type, and functions as a repressor region in a different cell type. In certain embodiments, the CTR promoter is a hybrid or heterologous promoter (e.g., the promoter contains heterologous sequences or contains sequences from a different source). For example, the CTR promoter comprises a minimal promoter from a first source and an enhancer element from a second source.

Techniques to determine regions in a CTR promoter that are minimal promoter regions or that have regulatory functions (e.g., activator or repressor functions) are described in the art, e.g., see Lodish et al., *Molecular Cell Biology*, W.H. Freeman and Company, New York, N.Y., 2000, at page 366. Briefly, a genomic DNA fragment upstream of the initiation start site of a gene is cloned into a reporter construct so that the genomic DNA fragment is operably linked to an ORF encoding a reporter. This construct is introduced into cells and the activity or expression level of the reporter is determined. Various fragments, e.g., fragments between 10 bps to 10,000 bps may be tested for transcriptional regulatory function. In addition, overlapping linker scanning mutations can be introduced from one end of the region being analyzed to the other end, and the mutant reporter constructs can be assayed in cells for the activity of the reporter. Mutations that affect the activity of the reporter relative to the wild-type control (promoter region with no mutations) may be promoter elements that are involved in transcriptional regulation. Using this method, minimal promoter regions, enhancer promoter regions and repressor promoter regions may be identified and validated.

Other methods known in the art include, but are not limited to, electrophoretic mobility shift assay (EMSA), DNase footprinting assay, and chromatin immuprecipitation (Chip) assay. Such assays can be used to identify and/or validate a promoter region that has specific affinity for a transcription factor. In vitro transcription assays using HeLa cell extracts may also be used to analyze promoter elements.

Many transcription factors and their corresponding consensus DNA binding elements have been described in the art and can readily be determined (see, e.g., Ghosh, D., Nucleic Acids Res., 21:3117-3118, 1993). In specific embodiments, a CTR promoter may comprise one or more transcription factor consensus DNA binding elements. Non-limiting examples of transcription factors and their consensus DNA binding elements include the following (numbers in "{ }" indicate the range of number of bps that can be present; "Pu" represents purines (adenine (A) or guanine (G)); "Py" represents pyrimidines (thymine (T) or cytosine (C)); " . . . " indicates one or more bps separating the sequences; nucleic acids in "[ ]" indicate choices of nucleic acids that may be in the position):

```
p53: PuPuPuC[A/T][T/A]GPyPyPy{0-13}PuPuPuC[A/T][T/A]GPyPyPy (SEQ ID NO: 1),
or

GGACATGCCCGGGCATGTCC (SEQ ID NO: 2)(see, e.g., El-Deiry et al., Nat. Genet.,
1992, 1: 45-49, and Funk et al., Mol. Cell. Biol., 1992, 12: 2866-2871);

Smads: GTCT, or AGAC (see, e.g., Zawel et al., Mol. Cell, 1998, 1: 611-617);

ERE: GGTCA . . . TGACC(SEQ ID NO: 3);

Sox2-Oct4: C[A/T]TTGT[A/T/G].{1,3}ATG[C/A][A/T][A/T][A/G][T/C](SEQ ID NO: 4);

BPV-E2: ACCG . . . CGGT;

GR: AGAACAGATG(SEQ ID NO: 5);

NF-I: TGAATATGGGCCA(SEQ ID NO: 6);

SRF: AAGATGCGGATATTGGCGAT(SEQ ID NO: 7);

Sp1: ACGCCC;

c-Fos: AACATGACTCAGAGGAA(SEQ ID NO: 8);

60k-protein: ATTAAATTTTAAATT(SEQ ID NO: 9);

ABF1: [A/T][G/A/T]C.[T/C] . . . ACGA[G/A/T](SEQ ID NO: 10);

ACE1: TTTTTTGCTGGAACGGTTCAG(SEQ ID NO: 11);

ADR1: TAAGTTGGAGAA(SEQ ID NO: 12);

AP-1: ACTCAGAGGAAAA(SEQ ID NO: 13);

AP-2: AAAGGGCCGGTGGGCGGGAGATT(SEQ ID NO: 14);

AP-3: ACTTTCCACACC(SEQ ID NO: 15);

AP-4: [T/C]CAGCTG[T/C]GG(SEQ ID NO: 16);

AP-5: CTGTGGAATG(SEQ ID NO: 17);

APF: AGGTTAATAATTTTCCA(SEQ ID NO: 18);

APF/HNF1: TGGTTAATGATCTACAGT(SEQ ID NO: 19);

ATF: GTGACGT[A/C][G/A];

ATF/CREB: AAATTGACGTCATGGTAA(SEQ ID NO: 20);

Adf-1: GAGATCGCGTAACGGTAGATAA(SEQ ID NO: 21);

B1: AA[G/A][G/A]GGAA[G/A][T/C]G(SEQ ID NO: 22);

B1/B2: ATTTGTAT;

B2: TCCTATCA;

BGP1: AATTGCAGAGCTGGGAATCGGGGGGGGGG(SEQ ID NO: 23);

BPV-E2: ACC . . . GGT;

C/EBP: ACAGGATATCTGTGGTAAGCAGTT(SEQ ID NO: 24);

CBF: GG[T/C]CAATCT;

CDF1: CTAAATAC;
```

COUP: CCAGGGGTCAGGGGGGGGGTGCTT(SEQ ID NO: 25);

CP1: AGCCAAT;

CP2: AGCCACT;

CREB: CCCATGGCCGTCATACTGTGACGTC(SEQ ID NO: 26);

CREB/ATF: GGCTTTCGTCACAGGGTG(SEQ ID NO: 27);

CTF: ACCCCGCCCA(SEQ ID NO: 28);

CTF/CBP: GATTGG;

CTF/CP1: GCCAATGACAAGACG(SEQ ID NO: 29);

CTF/NF-1: ACTGGCCAGCAGCCAAC(SEQ ID NO: 30);

CTF/NF-I: AGCCAAT;

CYP1: CTAATAGCGATAATAGCGAGGG(SEQ ID NO: 31);

DTF: AAAAGAACATCTTTT(SEQ ID NO: 32);

E-box-factors: CAGGTGGC;

E2F: CAATTTTCGCGCGG(SEQ ID NO: 33);

E2aECb: TGGGAATT;

E4F1: ACGTAACGT;

E4TF1: [G/A]TGACGT;

EBNA1: TAGCATATGCTA(SEQ ID NO: 34);

EBP1: GGGACTTTCC(SEQ ID NO: 35);

EF-1: CAACTGATAAGGAT(SEQ ID NO: 36);

EF-C: AAGTGTTTGCTGACGCAACCCCCACT(SEQ ID NO: 37);

EFI: AAGCACCGTGCATGCCGATTGGTGGAAGTA(SEQ ID NO: 38);

EFII: TATGCA;

EKLF: CCACACCC;

ENKTF1: TGGCGTA;

ETF: CAGCCCCCGGCGCAG(SEQ ID NO: 39);

ETFA: AACTACGTCA(SEQ ID NO: 40);

EivF: GT[G/T]ACGT;

EivF/CREB: GT[G/T]ACG[A/T];

GATA-1: AAGTATCACT(SEQ ID NO: 41);

GC2: GAGCTTCTAAATTATCCATCAGCACAAGC(SEQ ID NO: 42);

GCN4: AAGAGTCAT;

GHF-1: CAGTGGCCCCATGCATAAATGTACACAGAA(SEQ ID NO: 43);

Gin: TTATCCAAAACCTCGGTTTACAGGAAAC(SEQ ID NO: 44);

H2TFI: TGGGGATTCCCCA(SEQ ID NO: 45);

H4TF-1: GATTTC;

HAP: CTGCGAATGTTCGCG(SEQ ID NO: 46);

HAP1: AACCTCCGTTATCTCCATT(SEQ ID NO: 47);

HAP2/3: TGATTGGT;

HIVEN86A: GGGGAATCTCCC(SEQ ID NO: 48);

HNF-1: CTGTGAAATATTAACTAAA(SEQ ID NO: 49);

-continued

HNF1: CCTTGGTTAATATTCACCAGCAGCCTC(SEQ ID NO: 50);

HNFI: AACAAACTGTCAAATATTAACTAAAGGGAG(SEQ ID NO: 51);

HSTF: AAATAAAGAATATTCTAGAATCCC(SEQ ID NO: 52);

HiNF-A: AGAAATG;

ICP4: CGGATGGGCGGGGCCGGGGGTTCGACCAAC(SEQ ID NO: 53);

ICSBP: [T/C][G/A]GTTTC[G/A][T/C]TT[T/C][T/C](SEQ ID NO: 54);

ICSbf: AGTTTCACTTCT(SEQ ID NO: 55);

IEF1: GCCATCTG;

ITF: GAGAAGTGAAAGTGG(SEQ ID NO: 56);

IgNF-A: ATGCAAAT;

IgPE-1: ATATGGGCCAAACAGGATATCTGTGGTAAG(SEQ ID NO: 57);

IgPE-2: CCACCAAACCGAAAGTCCAGG(SEQ ID NO: 58);

IgPE-3: CCTGGGTAATTTGCATTTCTAAAAT(SEQ ID NO: 59);

KBF1: GGGGATTCCCC(SEQ ID NO: 60);

LF-A1: CAGATCCCAGCCAGTGGACTTAGCCCCTGT(SEQ ID NO: 61);

LF-A2: CTCCGATAACTG(SEQ ID NO: 62);

LF-B1: ACCTTGGTTAATATTCACCAGCA(SEQ ID NO: 63);

LF-B2: GGGTGACCTTGGTTAATATT(SEQ ID NO: 64);

LF-C: TGCCCCTCTGGATCCACTGCTTAA(SEQ ID NO: 65);

LSF: CCGCCC;

LVa: GAACAG;

LVb: CAGGATA;

MAT-alpha-1: ATGTAGAAAAGTACAT(SEQ ID NO: 66);

MAT-alpha-2: AATTACAT;

MATa1: ATGTGAATGAATACAT(SEQ ID NO: 67);

MBF-I: TTTTGCACACGGCAC(SEQ ID NO: 68);

MCM1: TTCCTAATTAGGAA(SEQ ID NO: 69);

MEP-1: CTCTGCACTCCGCCC(SEQ ID NO: 70);

MLTF: CGTGAC;

MTF1: CT.TGC[G/A]C.CGGCCC(SEQ ID NO: 71);

NF-GMa: GAGATTCCAC(SEQ ID NO: 72);

NF-GMb: TCAGGTA;

NF-I: AAAACCTTAAATAGGTTTAGAA(SEQ ID NO: 73);

NF-I/CTF: TAGTTGGCCCGCTGCCCTGG(SEQ ID NO: 74);

NF-InsE1: GGCCATCTTG(SEQ ID NO: 75);

NF-InsE2: TGCCAGCTGC(SEQ ID NO: 76);

NF-InsE3: TGCCACATGA(SEQ ID NO: 77);

NF-MHCIIA: GAGTGATGACTCACGTCAAG(SEQ ID NO: 78);

NF-MHCIIB: AGAACCAATGGGCAC(SEQ ID NO: 79);

NF-X: CCTAGCAACAGATG(SEQ ID NO: 80);

NF-Y: ATTTTTCTGATTGGTTAAAAGT(SEQ ID NO: 81);

NF-kB: AGGGACTTTCC(SEQ ID NO: 82);

NF-kB/H2TF1: GGGGAATCCCC(SEQ ID NO: 83);

NF-uE1: AAGATGGC;

NF-uE2: AGCAGCTGGC(SEQ ID NO: 84);

NF-uE3: AGGTCATGTGGCAAG(SEQ ID NO: 85);

NF-uE4: CAGGTGGT;

NFBK: GGGAATGCAGCCAAA(SEQ ID NO: 86);

NFI: ACATTCTCCTTGCCAAG(SEQ ID NO: 87);

Oct-1: AAGTATGCAAAG(SEQ ID NO: 88);

Oct-1/C1/C2: G[T/C]ATG.TAATGA[G/A]ATTC[T/C]TTG.GGG(SEQ ID NO: 89);

Oct-1/C1/a'-TIF: GTGCATGCTAATGATATTCTTTGGGG(SEQ ID NO: 90);

Oct-2: ATTTGCAT;

Oct-factors: ATGCAAAT;

PEA1: GAAGTGACTAACTG(SEQ ID NO: 91);

PEA2: ACTAACTGACCGCAGCTGGCC(SEQ ID NO: 92);

PEA3: AGGAAG;

PEB1: CAGAGGGCAGTGTG(SEQ ID NO: 93);

PEBP2: GACCGC;

RFX1: ACCCTTCCCCTAGCAACAGAT(SEQ ID NO: 94);

SBF-B: TAAATATAAAA(SEQ ID NO: 95);

SBF-E: ATGGGTTTTTG(SEQ ID NO: 96);

SCR-indf: CAGTTCCCGTCAATG(SEQ ID NO: 97);

STE7/12: GTTAGACGTTTCAGCTTCCAAAACAGAAGA(SEQ ID NO: 98);

SWI4: CACGAAAA;

Sp1: ACCCCGCCCA(SEQ ID NO: 108);

Sp1/CRF: CGGGCGGGATTGG(SEQ ID NO: 99);

T3rec: AGGTAAGATCAGGGGACG(SEQ ID NO: 100);

TAB: TATAAAAGCAGACGC(SEQ ID NO: 101);

TAF: TCGTTTTGTACGTTTTTCA(SEQ ID NO: 102);

TEF1: AAGCATGCA;

TEF2: GGGTGTGG;

TUF: AACATCCGTGCA(SEQ ID NO: 103);

TyBF: GTCATCATAGACG(SEQ ID NO: 104);

UBP1: CTCTCTGG;

XREbf: CACGC[A/T];

XlHbox1: CAATTAAA;

f-EBP: GATGTCCATATTAGGACATC(SEQ ID NO: 105);

myosin-specific: GTCGCC;

oct-B1A: CTTTGCAT;

oct-B1B: CTTTGCAT;

```
oct-B2:  CTTGCAT;

oct-B3:  CTTTGCAT uEBP-E:  T . . . A[G/T][T/C] . . . [G/T] . . . [A/C]T.ATGA(SEQ ID NO: 106);
and x-box-bp: C CTAGCAACAGATG(SEQ ID NO: 107).
```

A non-limiting example of a consensus binding sequence for the Spl/KLF family based on mutational analysis of a KLF family member (KLF4) binding site is (G/A)(G/A)GG(C/T)G(C/T) (see, e.g., Shields et al., *Nucleic Acids. Res.*, 1998, 26:796-802). A non-limiting example of a consensus binding sequence for c-Myc is PuACCACGTGCTC (SEQ ID NO: 109), wherein "Pu" represents a purine nucleotide (see, e.g., Papoulas et al., *J. Biol. Chem.*, 1992, 267(15): 10470-10480).

In certain aspects, a CTR promoter is a promoter regulating transcription of a CTR gene that is an RNA molecule, such as ribozymes and microRNAs (miRNAs) that is not translated. miRNAs are single-stranded RNA molecules processed into 21-23 nucleotides in length, and regulate gene expression of other genes predominantly via binding to mRNA of target genes and inhibiting translation of the target mRNA. Precursors of miRNAs are single-stranded RNA that form a short stem-loop structure which is further processed into a functional miRNA. Mature miRNA molecules are partially complementary to one or more mRNA molecules. Ribozymes are RNA molecules that catalyze a chemical reaction.

The choice of CTR promoter is dependent on the specific cellular process of interest and the methods described herein. For example, to identify modulators of stem cell maintenance/self-renewal and/or proliferation, the CTR promoter can be a stem cell promoter (e.g., a promoter that regulates expression of a stem cell specific gene or a stem cell associated gene). The stem cell promoters may be, but are not limited to, ESC promoters, neural stem cell promoters, hair follicle (bulge) stem cell promoters, epithelial stem cell promoters, muscle stem cell promoters, mesenchymal stem cell promoters, skin stem cell promoters, or HSC promoters.

Other non-limiting examples of CTR promoters include a somatic cell promoter, ESC promoter, progenitor cell promoter, myocyte promoter (e.g., myocyte specific or myocyte associated promoter), keratinocyte promoter, fibroblast promoter, epidermal basal cell promoter, Beta cell (pancreas) promoter, hepatocyte promoter, skeletal muscle promoter, hepatic stellate cell promoter, heart muscle cell promoter, monocytes promoter, retinal pigment epithelial cell promoter, and dopaminergic neuron promoter. In certain embodiments, the CTR promoter comprises a fragment of such promoters.

In some embodiments, a CTR promoter is a promoter regulating gene expression of genes specific for, or associated with, one of the following cell types: epidermal keratinocyte (differentiating epidermal cell), epidermal basal cell (stem cell), keratinocyte of fingernails and toenails, nail bed basal cell (stem cell), medullary hair shaft cell, cortical hair shaft cell, cuticular hair shaft cell, cuticular hair root sheath cell, hair root sheath cell of Huxley's layer, hair root sheath cell of Henle's layer, external hair root sheath cell, hair matrix cell (stem cell), surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, urinary epithelium cell (lining urinary bladder and urinary ducts), salivary gland mucous cell (polysaccharide-rich secretion), salivary gland serous cell (glycoprotein enzyme-rich secretion), von Ebner's gland cell in tongue (washes taste buds), mammary gland cell (milk secretion), lacrimal gland cell (tear secretion), ceruminous gland cell in ear (wax secretion), eccrine sweat gland dark cell (glycoprotein secretion), eccrine sweat gland clear cell (small molecule secretion), apocrine sweat gland cell (odoriferous secretion, sex-hormone sensitive), gland of Moll cell in eyelid (specialized sweat gland), sebaceous gland cell (lipid-rich sebum secretion), bowman's gland cell in nose (washes olfactory epithelium), Brunner's gland cell in duodenum (enzymes and alkaline mucus), seminal vesicle cell (secretes seminal fluid components, including fructose for swimming sperm), prostate gland cell (secretes seminal fluid components), bulbourethral gland cell (mucus secretion), Bartholin's gland cell (vaginal lubricant secretion), gland of Littre cell (mucus secretion), uterus endometrium cell (carbohydrate secretion), isolated goblet cell of respiratory and digestive tracts (mucus secretion), stomach lining mucous cell (mucus secretion), gastric gland zymogenic cell (pepsinogen secretion), gastric gland oxyntic cell (hydrochloric acid secretion), pancreatic acinar cell (bicarbonate and digestive enzyme secretion), paneth cell of small intestine (lysozyme secretion), type II pneumocyte of lung (surfactant secretion), clara cell of lung, anterior pituitary cells, somatotropes, lactotropes, thyrotropes, gonadotropes, corticotropes, intermediate pituitary cell, secreting melanocyte-stimulating hormone, magnocellular neurosecretory cells (secreting oxytocin and/or secreting vasopressin), gut and respiratory tract cells (secreting serotonin, secreting endorphin, secreting somatostatin, secreting gastrin, secreting secretin, secreting cholecystokinin, secreting insulin, secreting glucagons, and/or secreting bombesin), thyroid gland cells, thyroid epithelial cell, parafollicular cell, parathyroid gland cells, parathyroid chief cell, oxyphil cell, adrenal gland cells, chromaffin cells, adrenal gland secreting steroid hormones (mineralcorticoids and gluco corticoids), Leydig cell of testes secreting testosterone, theca interna cell of ovarian follicle secreting estrogen, corpus luteum cell of ruptured ovarian follicle secreting progesterone (Granulosa lutein cells, and Theca lutein cells), juxtaglomerular cell (renin secretion), macula densa cell of kidney, peripolar cell of kidney, mesangial cell of kidney, hepatocyte (liver cell), white fat cell, brown fat cell, liver lipocyte, kidney glomerulus parietal cell, kidney glomerulus podocyte, kidney proximal tubule brush border cell, loop of Henle thin segment cell, kidney distal tubule cell, kidney collecting duct cell, type I pneumocyte (lining air space of lung), pancreatic duct cell (centroacinar cell), nonstriated duct cell (of sweat gland, salivary gland, mammary gland, etc.) such as principal cell and intercalated cell, duct cell (of seminal vesicle, prostate gland, etc.), intestinal brush border cell (with microvilli), exocrine gland striated duct cell, gall bladder epithelial cell, ductulus efferens nonciliated cell, epididymal principal cell, epididymal basal cell, blood vessel and lymphatic vascular endothelial fenestrated cell, blood vessel and lymphatic vascular endothelial continuous cell, blood vessel and lymphatic vascular endothelial splenic cell, synovial cell (lining joint cavities, hyaluronic acid secretion), serosal cell (lining peritoneal, pleural, and pericardial cavities), squamous cell (lining perilymphatic space of ear), squamous cell (lining endolymphatic space of ear), columnar cell of endolymphatic sac with microvilli (lining endolymphatic space of ear), columnar cell of endolymphatic sac without microvilli (lining endolymphatic space of ear), dark cell (lining endolymphatic space of ear), vestibular membrane cell (lining endolymphatic space of ear), stria vascularis basal cell (lining endolymphatic space of ear), stria vascularis marginal cell (lining endolymphatic space of ear), cell of Claudius (lining endolymphatic space of ear), cell of Boettcher (lining endolymphatic space of ear), choroid plexus cell (cerebrospinal fluid secretion), pia-arachnoid squamous cell, pigmented ciliary epithelium cell of eye, nonpigmented ciliary epithelium cell of eye, corneal endothelial cell, respiratory tract ciliated cell, oviduct ciliated cell (in female), uterine endometrial ciliated cell (in female), rete testis ciliated cell (in male), ductulus efferens ciliated cell (in male), ciliated ependymal cell of central nervous system (lining brain cavities), ameloblast epithelial cell (tooth enamel secretion), planum semilunatum epithelial cell of vestibular apparatus of ear (proteoglycan secretion), organ of Corti interdental epithelial cell (secreting tectorial membrane covering hair cells), loose connective tissue fibroblasts, corneal fibroblasts (corneal keratocytes), tendon fibroblasts, bone marrow reticular tissue fibroblasts, other nonepithelial fibroblasts, pericyte, nucleus pulposus cell of intervertebral disc, cementoblast/cementocyte (tooth root bonelike cementum secretion), ontoblast/odontocyte (tooth dentin secretion), hyaline cartilage chondrocyte, fibrocartilage chondrocyte, elastic cartilage chondrocyte, oteoblast/osteocyte, osteoprogenitor cell (stem cell of osteoblasts), hyalocyte of vitreous body of eye, stellate cell of perilymphatic space of ear, hepatic stellate cell (Ito cell), pancreatic stellate cell, skeletal muscle cells (such as Red skeletal muscle cell (slow), white skeletal muscle cell (fast), intermediate skeletal muscle cell, nuclear bag cell of muscle spindle, and nuclear chain cell of muscle spindle), satellite cell (stem cell), heart muscle cells (such as ordinary heart muscle cell, nodal heart muscle cell, and purkinje fiber cell), smooth muscle cell (various types), myoepithelial cell of iris, myoepithelial cell of exocrine glands, erythrocyte (red blood cell), megakaryocyte (platelet precursor), monocytes, connective tissue macrophage (various types), epidermal Langerhans cell, osteoclast (in bone), dendritic cell (in lymphoid tissues), microglial cell (in central nervous system), neutrophil granulocyte, eosinophil granulocyte, basophil granulocyte, mast cell, helper T cell, suppressor T cell, cytotoxic T cell, natural Killer T cell, B cell, natural killer cell, reticulocyte, stem cells and committed progenitors for the blood and immune system (various types), auditory outer hair cell of organ of Corti, basal cell of olfactory epithelium (stem cell for olfactory neurons), cold-sensitive primary sensory neurons, heat-sensitive primary sensory neurons, merkel cell of epidermis (touch sensor), olfactory receptor neuron, pain-sensitive primary sensory neurons (various types), photoreceptor cells of retina in eye (such as photoreceptor rod cells, photoreceptor blue-sensitive cone cell of eye, photoreceptor green-sensitive cone cell of eye, photoreceptor red-sensitive cone cell of eye), proprioceptive primary sensory neurons (various types), touch-sensitive primary sensory neurons (various types), type I carotid body cell (blood pH sensor), type II carotid body cell (blood pH sensor), type I hair cell of vestibular apparatus of ear (acceleration and gravity), type II hair cell of vestibular apparatus of ear (acceleration and gravity), type I taste bud cell, cholinergic neural cell (various types), adrenergic neural cell (various types), peptidergic neural cell (various types), inner pillar cell of organ of Corti, outer pillar cell of organ of Corti, inner phalangeal cell of organ of Corti, outer phalangeal cell of organ of Corti, border cell of organ of Corti, hensen cell of organ of Cortim vestibular apparatus supporting cell, type I taste bud supporting cell, olfactory epithelium supporting cell, schwann cell, satellite cell (encapsulating peripheral nerve cell bodies), enteric glial cell, astrocyte (various types), neuron cells (large variety of types, still poorly classified), oligodendrocyte, spindle neuron, anterior lens epithelial cell, crystallin-containing lens fiber cell, melanocyte, retinal pigmented epithelial cell, oogonium/oocyte, spermatid, spermatocyte, spermatogonium cell (stem cell for spermatocyte), spermatozoon, ovarian follicle cell, sertoli cell (in testis), thymus epithelial cell, and interstitial kidney cells. In some embodiments, a CTR promoter comprises a fragment of a promoter regulating gene expression of genes specific for, or associated with, one of the cell types described above.

In particular embodiments relating to modulators of stem cells or of iPS cells, CTR promoters may include, but are not limited to, promoters or elements of promoters of Oct4, Sox2, Klf4, c-myc, LIN28, Nanog, SSEA-3, or SSEA-4. In certain embodiments, the CTR promoter is a promoter or an element of a promoter of one of the following genes: Notch, WNT, Dax1, Eras, Fbox, Foxd3, Rex1, and Zfp296. In specific embodiments, the CTR promoter comprises a region of the Oct4 promoter such as a region of the Oct4 promoter comprising −3917 bp to +55 bp relative to the transcription start site, or a portion thereof, which may comprise the minimal promoter region. In certain embodiments, the CTR promoter comprises the first 250 bps from the transcription start site of the Oct4 promoter. In specific embodiments, the CTR promoter comprises a region of the Nanog promoter such as a region of the Nanog promoter comprising −289 bp to +117 bp relative to the transcription start site, or a portion thereof, which may comprise the minimal promoter region. In some embodiments, the CTR promoter comprises about 200 bps of the Nanog promoter. In certain embodiments, the CTR promoter comprises a region of the Nanog promoter that contains a Sox transcription factor binding element (CATTGTA). In particular embodiments, the CTR promoter comprises a region of the Nanog promoter that contains an Oct transcription factor binding element (ATGCAAAA).

In some embodiments relating to modulators of hair follicle (bulge) stem cell, CTR promoters may include, but are not limited to, promoters or promoter fragments of NFATc1, Sox9, TCF3, or Lhx2. In certain embodiments, a CTR promoter may be a promoter or promoter fragment of a hair follicle (bulge) stem cell marker, such as, K15, CD200, CD34, CD271, nestin, or Lgr5.

In some embodiments relating to modulators of epidermal basal cell, CTR promoters may include, but are not limited to, promoters or promoter fragments of c-rel, RelA, Delta1, or Fringe. In certain embodiments, a CTR promoter may be a promoter or promoter fragment of an epidermal basal cell, such as $\beta_1$-integrin, $\alpha$6-integrin, keratin 15, p63, or CD34.

In some embodiments relating to modulators of epithelial stem cell, CTR promoters may include, but are not limited to, promoters or promoter fragments of Bmi-1, Tcf-4, β- or catenin. In certain embodiments, a CTR promoter may be a promoter or promoter fragment of an epithelial stem cell marker, such as ABCG2, Bmi-1, DeltaNp63, p75, HEA, CD44, $\alpha2\beta1$ integrin, amin A, CD49f, Lgr5, or CD133.

In other embodiments relating to modulators of skin tissue cells, CTR promoters may include, but are not limited to, promoters or promoter fragments of a gene selected from the group consisting of: NFATc1, SOX9, TCF3, LHX2, CD200, K15, ID2, DKK3, WIF1, FZD1, FZD2, PHLDA1, FOLLISTATIN, DIO2, LCE2B, ASPRV1, DEFB4, PI3, RNASE7, K19, ITGB1, REL, RELA, DLL1, BMI1, TCF4, CTNNB1, MC1R, SLC45A2, and SLC24A5.

In some embodiments relating to modulators of Beta cell (pancreas), CTR promoters may include, but are not limited to, promoters or promoter fragments of Mnx1, Pdx1, Nkx6-1, Nkx2-2, Mafb, Mafa, Ins1, or Slc2a2. In certain embodiments, a CTR promoter may be a promoter or promoter fragment of a pancreatic Beta cell marker, such as Ins1.

In some embodiments relating to modulators of hepatocytes, CTR promoters may include, but are not limited to, promoters or promoter fragments of Prox1, Rex3, WT1, C/EBP alpha and beta, HNF-1, HNF-4, albumin, alpha-Fetoprotein (AFP), alpha-anti-Trypsin, Annexin I, or Annexin II. In certain embodiments, a CTR promoter may be a promoter or promoter fragment of a hepatocyte marker, such as alpha-Fetoprotein (AFP), alpha-anti-Trypsin, Annexin I, or Annexin II.

In some embodiments relating to modulators of skeletal muscle cells, CTR promoters may include, but are not limited to, promoters or promoter fragments of MyoD, Myf5, myogenin, Mrf4, Mef2, MURC, myosin Heavy Chain, troponin, or tropomyosin. In certain embodiments, a CTR promoter may be a promoter or promoter fragment of a skeletal muscle cell, such as Myosin Heavy Chain, troponin, or tropomyosin.

In some embodiments relating to modulators of hepatic stellate cells, CTR promoters may include, but are not limited to, promoters or promoter fragments of Foxl1, PPARgamma, Egr-1, alpha-smooth muscle actin, reelin, or p75NTR. In certain embodiments, a CTR promoter may be a promoter or promoter fragment of a hepatic stellate cell marker, such as alpha-smooth muscle actin, reelin, or p75NTR.

In some embodiments relating to modulators of muscle stem cells, CTR promoters may include, but are not limited to, promoters or promoter fragments of MyoD, Pax7, Runx2, Myf5, M-cadherin, neural cell adhesion molecule-1, CD56, CD34, or CD144. In certain embodiments, a CTR promoter may be a promoter or promoter fragment of a muscle stem cell marker such as M-cadherin, neural cell adhesion molecule-1, CD56, CD34, or CD144.

In some embodiments relating to modulators of heart muscle cells, CTR promoters may include, but are not limited to, promoters or promoter fragments of Nkx2.5, MEF2C, GATA4, myosin heavy chain, alpha-actinin, desmin, antinatruretic peptide, or cardiac troponin. In certain embodiments, a CTR promoter may be a promoter or promoter fragment of a heart muscle cell marker such as myosin heavy chain, alpha-actinin, desmin, antinatruretic peptide, or cardiac troponin.

In some embodiments relating to modulators of monocytes, CTR promoters may include, but are not limited to, promoters or promoter fragments of PU.1, C/EBPalpha, AML1, RARalpha, MZF-1, Hox, STAT, CD11b, CD14, CD16, CD36, CD64, CD163, M-CSF receptor, or GM-CSF receptor. In certain embodiments, a CTR promoter may be a promoter or promoter fragment of a monocyte marker such as CD11b, CD14, CD16, CD36, CD64, CD163, M-CSF receptor, and GM-CSF receptor.

In some embodiments relating to modulators of retinal pigment epithelial cells, CTR promoters may include, but are not limited to, promoters or promoter fragments of microphthalmia, ELF3, bestrophin, cytokeratins 8 and 18, ZO-1, TIMP3, or RPE 65. In certain embodiments, a CTR promoter may be a promoter or promoter fragment of a retinal pigment epithelial cell marker such as bestrophin, cytokeratins 8 and 18, ZO-1, TIMP3 or RPE65.

In some embodiments relating to modulators of cells from the eye, a CTR promoter may be, but is not limited to, the Six6 (NP_031400) promoter or a fragment thereof. In other embodiments relating to modulators of cells from the eye, CTR promoters may include, but are not limited to, promoters or promoter fragments of a gene selected from the group consisting of: RPE65, ABCA4, COLL11A1, GNAT2, RHO, GNB3, GNAT1, GNGT1, PDE6A, PDE6B, PDE6G, CNGA1, CNGB1, RCVN, SAG, GUCA1A, SLC24A1, NRG4, ABCA4, PRPH2, ROM1, RDH5, TTR, BEST1, CTSD, CST3, HMCN1, RD3, EFEMP1, ALMS1, CNGA3, CNNM4, MERTK, ARR3, PDE6H, CPLX4, OPAL MPP4, NRL, CLUL1, RDH12, RBP3, PDC, CRX, IMPG1, RAX RTBDN, RP1, CRABP1, RLBP1, RS1, STRA13, PROM1, LRAT, TULP1, GUCY2D, VSX1, RGS16, NR2E3, GUCY2F, AOC2, RGR, RDH11, FSCN2, POU6F2, SLC1A7, SLC24A1, ZNF385A, SDR16C5, HSD17B14, DHRS7, SLC24A2, PITPNC1, ALDH1A1, ALDH1A2, and ALDH1A3.

In some embodiments relating to modulators of mesenchymal stem cells, CTR promoters may include, but are not limited to, promoters or promoter fragments of ETV1, ETV5, FOXP1, GATA6, HMGA2, SIM2, SOX11, STRO-1, CD90, CD105, or p75NTR. In certain embodiments, a CTR promoter may be a promoter or promoter fragment of mesenchymal stem cell marker such as STRO-1, CD90, CD105, or p75NTR.

In some embodiments relating to modulators of neural stem cells, CTR promoters may include, but are not limited to, promoters or promoter fragments of PLZF, PLAGL1, Dach1, Foxg1, NR2F1, Nestin, PSA-NCAM, p75 Neurotrophin R, or Vimentin. In certain embodiments, a CTR promoter may be a promoter or promoter fragment of a neural stem cell marker such as Nestin, PSA-NCAM, or p75 Neurotrophin R Vimentin.

In some embodiments relating to modulators of dopaminergic neurons, CTR promoters may include, but are not limited to, promoters or promoter fragments of Otx2, Lmx1a, Ngn2, Fox2a, Pitx3, engrailed, Nurr1, Wnt1, Fgf8, Shh, or Raldh1 (Ahd2). In certain embodiments, a CTR promoter may be a promoter or promoter fragment of a dopaminergic neuron marker such as Wnt1, Fgf8, Shh, or Raldh1 (Ahd2).

In some embodiments relating to modulators of hematopoietic stem cells, CTR promoters may include, but are not limited to, promoters or promoter fragments of Evi1, GATA-2, EGR1, Gfi-1, CD34, CD38, CD59, CD133, c-Kit, Sca-1, or ABCG2. In certain embodiments, a CTR promoter may be a promoter or promoter fragment of a hematopoietic stem cell marker such as CD34, CD59, CD133, or ABCG2.

In other embodiments relating to modulators of cardiac muscle cells, CTR promoters may include, but are not limited to, promoters or promoter fragments of a gene selected from the group consisting of: ACTN2, ADBR1, AFP, ALK3, ALK6, ANKRD1, ATF2, BMPR2, CKM, CMYA, COL3A1, CSRP3, CVD1, CXCL14, DCN, DES, DNM3, FGB, GATA4, GATA4, HSBP7, ISL1, KCNG2, KCNIP2, KCNJ2, KCNJA5, LDB3, LUM, MEF2C, MGP, MLC2v, MYBPC3, MYH6, MYH7, MYL3, MYLK3, MYOCD, MYOM1, MYOZ2, NKX2.5, NPPA, NPPB, PLN, RYR2, SLC4A3, SMAD1, SMAD5, SMAD8, SMPX, SYNPO2L, TAK1, TBX5, TBX5, TNNI1, TNNI3K, and TNNT2.

Table 1 provides a list of non-limiting examples of markers of certain cell types. Without being limited by theory, marker genes are specific to, or associated with, a particular cell type or they are predominantly or preferentially expressed in a particular cell type. In specific embodiments, the CTR promoter described herein is a promoter, or comprises a region of a promoter, of a marker gene, such as a marker gene selected from the group of genes presented in Table 1.

TABLE 1

Marker Genes and Associated Cell Type

| Marker Name | Cell Type |
|---|---|
| Blood Vessel | |
| Fetal liver kinase-1 (Flk1) | Endothelial |
| Smooth muscle cell-specific myosin heavy chain | Smooth muscle |
| Vascular endothelial cell cadherin | Smooth muscle |
| Bone | |
| Bone-specific alkaline phosphatase (BAP) | Osteoblast |
| Hydroxyapatite | Osteoblast |
| Osteocalcin (OC) | Osteoblast |
| Bone Marrow and Blood | |
| Bone morphogenetic protein receptor (BMPR) | Mesenchymal stem and progenitor cells |
| CD4 and CD8 | White blood cell (WBC) |
| CD34 | Hematopoietic stem cell (HSC), satellite, endothelial progenitor |
| CD34$^+$Sca1$^+$ Lin$^-$ profile | Mesencyhmal stem cell (MSC) |
| CD38 | Absent on HSC Present on WBC lineages |
| CD44 | Mesenchymal |
| c-Kit | HSC, MSC |
| Colony-forming unit (CFU) | HSC, MSC progenitor |
| Fibroblast colony-forming unit (CFU-F) | Bone marrow fibroblast |
| Hoechst dye | Absent on HSC |
| Leukocyte common antigen (CD45) | WBC |
| Lineage surface antigen (Lin) | HSC, MSC Differentiated RBC and WBC lineages |
| Mac-1 | WBC |
| Muc-18 (CD146) | Bone marrow fibroblasts, endothelial |
| Stem cell antigen (Sca-1) | HSC, MSC |
| Stro-1 antigen | Stromal (mesenchymal) precursor cells, hematopoietic cells |
| Thy-1 | HSC, MSC |
| Cartilage | |
| Collagen types II and IV | Chondrocyte |
| Keratin | Keratinocyte |
| Sulfated proteoglycan | Chondrocyte |
| Fat | |
| Adipocyte lipid-binding protein (ALBP) | Adipocyte |
| Fatty acid transporter (FAT) | Adipocyte |
| Adipocyte lipid-binding protein (ALBP) | Adipocyte |
| General | |
| Y chromosome | Male cells |
| Karyotype | Most cell types |
| Liver | |
| Albumin | Hepatocyte |
| B-1 integrin | Hepatocyte |
| Nervous System | |
| CD133 | Neural stem cell, HSC |
| Glial fibrillary acidic protein (GFAP) | Astrocyte |
| Microtubule-associated protein-2 (MAP-2) | Neuron |
| Myelin basic protein (MPB) | Oligodendrocyte |

TABLE 1-continued

Marker Genes and Associated Cell Type

| Marker Name | Cell Type |
|---|---|
| Nestin | Neural progenitor |
| Neural tubulin | Neuron |
| Neurofilament (NF) | Neuron |
| Neurosphere | Embryoid body (EB), ES |
| Noggin | Neuron |
| O4 | Oligodendrocyte |
| O1 | Oligodendrocyte |
| Synaptophysin | Neuron |
| Tau | Neuron |
| Pancreas | |
| Cytokeratin 19 (CK19) | Pancreatic epithelium |
| Glucagon | Pancreatic islet |
| Insulin | Pancreatic islet |
| Insulin-promoting factor-1 (PDX- 1) | Pancreatic islet |
| Nestin | Pancreatic progenitor |
| Pancreatic polypeptide | Pancreatic islet |
| Somatostatin | Pancreatic islet |
| Pluripotent Stem Cells | |
| Alkaline phosphatase | Embryonic stem (ES), embryonal carcinoma (EC) |
| Alpha-fetoprotein (AFP) | Endoderm |
| Bone morphogenetic protein-4 | Mesoderm |
| Brachyury | Mesoderm |
| Cluster designation 30 (CD30) | ES, EC |
| Cripto (TDGF-1) | ES, cardiomyocyte |
| GATA-4 gene | Endoderm |
| GCTM-2 | ES, EC |
| Genesis | ES, EC |
| Germ cell nuclear factor | ES, EC |
| Hepatocyte nuclear factor-4 (HNF-4) | Endoderm |
| Nestin | Ectoderm, neural and pancreatic progenitor |
| Neuronal cell-adhesion molecule (N-CAM) | Ectoderm |
| OCT4/POU5F1 | ES, EC |
| Pax6 | Ectoderm |
| Stage-specific embryonic antigen-3 (SSEA-3) | ES, EC |
| Stage-specific embryonic antigen-4 (SSEA-4) | ES, EC |
| Stem cell factor (SCF or c-Kit ligand) | ES, EC, HSC, MSC |
| Telomerase | ES, EC |
| TRA-1-60 | ES, EC |
| TRA-1-81 | ES, EC |
| Vimentin | Ectoderm, neural and pancreatic progenitor |
| Skeletal Muscle/Cardiac/Smooth Muscle | |
| MyoD and Pax7 | Myoblast, myocyte |
| Myogenin and MR4 | Skeletal myocyte |
| Myosin heavy chain | Cardiomyocyte |
| Myosin light chain | Skeletal myocyte |

In particular embodiments, a CTR promoter is a promoter of a gene of CTR factor, such as those described in section 4.2.1.

In specific embodiments, a CTR promoter is a human promoter. In particular embodiments, a CTR promoter is a mouse, rat, monkey, dog, cat, pig, sheep, goat, horse, chicken, frog, worm, insect, or cow promoter. In some embodiments, a CTR promoter is homologous to a human promoter. In certain embodiments, the CTR promoter is a mammalian promoter.

In specific embodiments, a CTR promoter comprises about 10 bps to 10,000 bps, 1 bp to 50 bps, 10 bps to 100 bps, 20 bps to 200 bps, 50 bps to 200 bps, 50 bps to 300 bps, 50 bps to 400 bps, 50 bps to 500 bps, 100 bps to 600 bps, 100 bps to 700 bps, 100 bps to 800 bps, 100 bps to 900 bps, 100 bps to 1,000 bps, 500 bps to 1,500 bps, 500 bps to 2,000 bps, 500 bps to 5,000 bps, or 1,000 bps to 10,000 bps, or any range in between.

In certain embodiments, the CTR promoter comprises at most about 10,000 bps, at most about 9,000 bps, at most about 8,000 bps, at most about 7,000 bps, at most about 6,000 bps, at most about 5,000 bps, at most about 4,000 bps, at most about 3,000 bps, at most about 2,000 bps, at most about 1,500 bps, at most about 1,000 bps, at most about 900 bps, at most about 800 bps, at most about 700 bps, at most about 600 bps, at most about 500 bps, at most about 400 bps, at most about 300 bps, at most about 200 bps, at most about 150 bps, at most about 100 bps, at most about 75 bps, at most about 50 bps, at most about 40 bps, at most about 30 bps, at most about 25 bps, at most about 20 bps, at most about 15 bps or at most about 10 bps.

In certain embodiments, the CTR promoter comprises at most about 10,000 bps, at most about 9,000 bps, at most about 8,000 bps, at most about 7,000 bps, at most about 6,000 bps, at most about 5,000 bps, at most about 4,000 bps, at most about 3,000 bps, at most about 2,000 bps, at most about 1,500 bps, at most about 1,000 bps, at most about 900 bps, at most about 800 bps, at most about 700 bps, at most about 600 bps, at most about 500 bps, at most about 400 bps, at most about 300 bps, at most about 200 bps, at most about 150 bps, at most about 100 bps, at most about 75 bps, at most about 50 bps, at most about 40 bps, at most about 30 bps, at most about 25 bps, at most about 20 bps, at most about 15 bps or at most about 10 bps upstream of the transcription initiation site.

In certain embodiments, the CTR promoter comprises at most about 200 bps, at most about 150 bps, at most about 100 bps, at most about 90 bps, at most about 80 bps, at most about 70 bps, at most about 60 bps, at most about 50 bps, at most about 40 bps, at most about 30 bps, at most about 20 bps, at most about 15 bps, at most about 10 bps, at most about 8 bps, at most about 9 bps, at most about 7 bps, at most about 6 bps, at most about 5 bps, at most about 4 bps, at most about 3 bps or at most about 2 bps downstream of the transcription initiation site.

In certain embodiments, the CTR promoter comprises at most about 10,000 bps, at most about 9,000 bps, at most about 8,000 bps, at most about 7,000 bps, at most about 6,000 bps, at most about 5,000 bps, at most about 4,000 bps, at most about 3,000 bps, at most about 2,000 bps, at most about 1,500 bps, at most about 1,000 bps, at most about 900 bps, at most about 800 bps, at most about 700 bps, at most about 600 bps, at most about 500 bps, at most about 400 bps, at most about 300 bps, at most about 200 bps, at most about 150 bps, at most about 100 bps, at most about 75 bps, at most about 50 bps, at most about 40 bps, at most about 30 bps, at most about 25 bps, at most about 20 bps, at most about 15 bps or at most about 10 bps.

In certain embodiments, the CTR promoter comprises at least about 10,000 bps, at least about 9,000 bps, at least about 8,000 bps, at least about 7,000 bps, at least about 6,000 bps, at least about 5,000 bps, at least about 4,000 bps, at least about 3,000 bps, at least about 2,000 bps, at least about 1,500 bps, at least about 1,000 bps, at least about 900 bps, at least about 800 bps, at least about 700 bps, at least about 600 bps, at least about 500 bps, at least about 400 bps, at least about 300 bps, at least about 200 bps, at least about 150 bps, at least about 100 bps, at least about 75 bps, at least about 50 bps, at least about 40 bps, at least about 30 bps, at least about 25 bps, at least about 20 bps, at least about 15 bps or at least about 10 bps upstream of the transcription initiation site.

In certain embodiments, the CTR promoter comprises at least about 100 bps, at least about 90 bps, at least about 80 bps, at least about 70 bps, at least about 60 bps, at least about 50 bps, at least about 40 bps, at least about 30 bps, at least about 20 bps, at least about 15 bps, at least about 10 bps, at least about 8 bps, at least about 9 bps, at least about 7 bps, at least about 6 bps, at least about 5 bps, at least about 4 bps, at least about 3 bps or at least about 2 bps downstream of the transcription initiation site.

Methods for isolating and cloning promoters are well known to one of skill in the art. For example, a genomic DNA fragment upstream of the initiation start site of a gene can be cloned into a reporter construct so that the genomic DNA fragment is operably linked to an ORF encoding a reporter. This reporter construct can be used to analyze the activity of the promoter or various fragments of the promoter. For certain genes, the promoter region has been identified.

Any technique known to the skilled artisan can be used to conduct a promoter analysis of a CTR gene of interest to identify those elements of the promoter with transcriptional regulation function that can confer cell type specificity (see, e.g., *Analytics of Protein-DNA Interactions*, Seitz et al. eds., Springer-Verlag New York, LLC, 2007). In certain embodiments, fragments of genomic DNA that surround the transcription start site of a CTR gene are cloned into a reporter construct so that they are operatively linked to a reporter gene. In specific embodiments, the genomic DNA fragment is also operably linked to a minimal promoter, such as a heterologous minimal promoter. In certain embodiments, the genomic DNA fragment already contains a minimal promoter. The resulting DNA construct is then introduced into a cell type that expresses the CTR gene of interest. If the reporter gene is expressed in the resulting cell, the genomic fragment contains the promoter element that confers cell type specificity for that cell type. The genomic fragment can then be further dissected to identify the minimum sequences that are required for expression in that cell type. In other embodiments, if the transcription factor(s) is known that activates the expression of the CTR gene of interest, an EMSA or DNA footprint experiment can be conducted with genomic DNA that surrounds the transcription start of the CTR gene of interest.

4.1.3. Target Sequences

The reporter nucleic acid constructs described herein comprises one or more target sequence nucleic acids, that encode RNA transcripts, referred to herein as target sequence RNA ("TSR"), e.g., TSR1, TSR2, TSR3, etc. When the target sequence encoded by the reporter nucleic acid is transcribed into RNA, i.e., the TSR, the transcribed TSR can be detected by a fluorogenic oligonucleotide, which comprises nucleic acid sequences that are partially or completely complementary to the target sequence and can hybridize to the transcribed TSR.

Any technique known to the skilled artisan can be used to detect the TSRs in a cell. In certain embodiments, fluorogenic oligonucleotides can be used. In certain embodiments, molecular beacons can be used. See e.g., U.S. Pat. No. 6,692,965, and International PCT Patent Application Publication No. WO 2005/079462 A2. In certain embodiments, the fluorogenic oligonucleotide is conjugated to a fluorophore and a quencher. The fluorogenic oligonucleotide adopts a structure or conformation when it is not bound to or hybridized with a target sequence, and adopts a different structure or conformation when it is bound to or hybridized with a target sequence. That is, conformational change of the fluorogenic oligonucleotide may occur in the presence of the target sequence, where this change results in decreased efficiency for the quenching of the signal that is emitted from the fluorophore when this is excited. In specific embodiments, the fluorescent signal that is emitted from the fluorogenic oligonucleotide in the presence of the target sequence is higher than the fluorescent signal that is emitted from the fluorogenic oligonucleotide in the absence of the target sequence. In specific embodiments, the fluorescent signal is quenched when the fluorogenic oligonucleotide is not hybridized to the target sequence. The unhybridized fluorogenic oligonucleotide may form a stem-loop structure. In certain aspects, the quenched detection signal may be a result of this stem-loop structure.

In specific embodiments, the fluorescent signal that is emitted from the fluorogenic oligonucleotide in the presence of the target sequence is at least about 5%, 10%, 20%, 30%, 40%, 50%, 60%, 70%, 80%, 90%, or 100% higher than the fluorescent signal that is emitted from the fluorogenic oligonucleotide in the absence of the target sequence. In specific embodiments, the fluorescent signal that is emitted from the fluorogenic oligonucleotide in the presence of the target sequence is at least about 1 fold, 1.5 fold, 2 fold, 3 fold, 4 fold, 5 fold, 10 fold, 15 fold, 20 fold, 50 fold, 100 fold, 500 fold, or 1,000 fold higher than the fluorescent signal that is emitted from the fluorogenic oligonucleotide in the absence of the target sequence.

A variety of RNA sequences, any of which may be used as target sequences (e.g., TSR1, TSR2, TSR3, etc.), including those encoding the reporters described above, or an untranslated region ("UTR") of the reporter. The target sequence may be a heterologous sequence (e.g., a sequence unrelated to the transcribed reporter nucleic acid sequence). The target sequence, which is for binding or hybridizing to the fluorogenic oligonucleotide, may be a part of a 3' UTR, such as the 3' UTR of the reporter nucleic acid construct that is cotranscribed with the reporter transcript. In certain embodiments, the target sequence, which is for binding or hybridizing to the fluorogenic oligonucleotide, may be a part of a 5' UTR, such as the 5' UTR of the reporter nucleic acid construct that is cotranscribed with the reporter transcript.

In certain embodiments, a TSR is cotranscribe with the reporter gene. The TSR that is cotranscibed with the reporter may or may not encode an amino acid sequence. In some embodiments, the target sequence can be in frame with the protein-coding portion of the message of the reporter gene or out of frame with it. Thus, the target sequence does not have to be translated for detection by the fluorogenic oligonucleotide. The target sequences may comprise multiple target sequences that are the same or different, wherein one fluorogenic oligonucleotide hybridizes to each target sequence. The target sequence may be located within the RNA encoding the gene of interest, such as the reporter, or the target sequence may be located within a 5'- or 3'-UTR, or immediately following or preceding the 5' or 3' UTR. In other embodiments, the target sequence is a heterologous sequence that is not homologous to any sequence within the ORF of the reporter, the 5' UTR, or the 3' UTR.

In particular embodiments, the reporter nucleic acid construct comprises a target sequence (e.g., TSR3) that is cotranscribed with the reporter. In specific embodiments, the target sequence that is cotranscribed with the reporter is located in the 3' UTR of the reporter transcript. In specific embodiments, the target sequence that is cotranscribed with the reporter is located in the 5' UTR of the reporter transcript. In specific embodiments, the target sequence that is cotranscribed with the reporter is located within the reporter transcript. In specific embodiments, the target sequence that is cotranscribed with the reporter is not homologous to any contiguous fragment of the reporter transcript. In certain aspects, a target sequence that is cotranscribed with the reporter, allows for selection of cells that have low basal transcription of the reporter using the fluorogenic oligonucleotides complementary to the target sequence. In some embodiments, the 3' UTR of the reporter transcript which contains a target sequence is a heterologous sequence.

The TSR may be an RNA having a secondary structure. The structure may be a three-arm junction structure. In some embodiments, the fluorogenic oligonucleotide may detect a sequence within the coding sequence for the protein of interest such as the reporter. In this case, the mRNA of the reporter serves as a TSR.

In specific embodiments, the reporter nucleic acid construct comprises one or more TSRs that are not cotranscribed with the reporter, but whose transcription are under the control of separate promoters. In particular embodiments, the first target sequence is 5' to the ORF encoding the reporter. In some embodiments, the first target sequence is 3' to the ORF encoding the reporter. The reporter nucleic acid construct comprises one or more target sequences, wherein the first and second target sequences flank the ORF encoding the reporter (e.g., one target sequence is 5' to the ORF encoding the reporter, and the second target sequence is 3' to the ORF encoding the reporter).

In certain embodiments, a target sequence operably linked to a constitutive promoter is in opposite orientation from that of the reporter. For example, the promoter construct upstream of the reporter ORF may result in transcription from the opposite strand of DNA from which transcription of the reporter occurs. In certain embodiments, a target sequence operably linked to a constitutive promoter which is downstream from the reporter ORF may be in the same orientation as the reporter ORF and may result in transcription from the same strand of DNA from which transcription of the reporter occurs. In some embodiments, a target sequence operably linked to a constitutive promoter is in the same orientation as that of the reporter ORF in a reporter nucleic acid construct.

In specific embodiments, a target sequence operably linked to a constitutive promoter is positioned at a certain distance from the other target sequences or from the reporter ORF to minimize cross transcriptional regulation or activation. In certain embodiments, a target sequence operably linked to a constitutive promoter is positioned at least 100 bps, 200 bps, 300 bps, 400 bps, 500 bps, 600 bps, 700 bps, 800 bps, 900 bps, 1,000 bps, 1,500 bps, 2,000 bps, 2,500 bps, 3,000 bps, 3,500 bps, 4,000 bps, 4,500 bps, 5,000 bps, 6,000 bps, 7,000 bps, 8,000 bps, 9,000 bps, or 10,000 bps from the other target sequences or from the reporter ORF. In certain embodiments, a target sequence operably linked to a constitutive promoter is positioned at most about 100 bps, 200 bps, 300 bps, 400 bps, 500 bps, 600 bps, 700 bps, 800 bps, 900 bps, 1,000 bps, 1,500 bps, 2,000 bps, 2,500 bps, 3,000 bps, 3,500 bps, 4,000 bps, 4,500 bps, 5,000 bps, 6,000 bps, 7,000 bps, 8,000 bps, 9,000 bps, or 10,000 bps from the other target sequences or from the reporter ORF.

The TSR may be an RNA having secondary structure. The structure may be a three-arm junction structure. In particular embodiments, the target sequence has a GC-content of about 30%-70%. In specific embodiments, the target sequence is at least about 30%, 35%, 40%, 45%, 50%, 55%, 60%, 65%, 70%, or 75% GC-rich. In other embodiments, the target sequence is at most about 30%, 35%, 40%, 45%, 50%, 55%, 60%, 65%, 70%, or 75% GC-rich.

In a specific embodiment, a target sequence or TSR is about 5 to 1,000 nucleotides, about 5 to 750 nucleotides, about 5 to 500 nucleotides, about 5 to 250 nucleotides, about 5 to 200 nucleotides, about 5 to 150 nucleotides, about 5 to 100 nucleotides, about 5 to 100 nucleotides, about 5 to 75 nucleotides, about 5 to 500 nucleotides, about 10 to 100 nucleotides, about 10 to 75 nucleotides, about 10 to 50 nucleotides, about 10 to 30 nucleotides, about 5 to 20 nucleotides, about 20 to 100 nucleotides, about 20 to 75 nucleotides, or about 30 to 100 nucleotides, in length, or any length in between. In a specific embodiment, a target sequence or TSR is about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In certain embodiments, a target sequence or TSR is at most 10 nucleotides, 15 nucleotides, 20 nucleotides, 25 nucleotides, 30 nucleotides, 35 nucleotides, 40 nucleotides, 45 nucleotides, 50 nucleotides, 55 nucleotides, 60 nucleotides, 65 nucleotides, 70 nucleotides, 75 nucleotides, 80 nucleotides, 85 nucleotides, 90 nucleotides, 95 nucleotides, or 100 nucleotides in length. In a specific embodiment, a target sequence or TSR is less than 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length.

In some embodiments, a TSR does not comprise a transcription termination sequence. In eukaryotic cells, purified RNA Polymerase III terminate transcription after polymerizing a series of U residues. The transcription termination sequence may comprise a series of U residues such as UUU, UUUU, UUUUU, UUUUUU, UUUUUUU, UUUUUUUU, or UUUUUUUUU. In certain embodiments a RNA Polymerase III transcription termination sequence may comprise an RNA sequence comprising 10 or more U residues, consecutively or nonconsecutively. In particular embodiments, the transcription termination sequence may comprise at least 40%, 50%, 55%, 60%, 65%, 70%, 75%, 80%, 85%, 90%, 95%, or 99% U residues. In bacteria, transcription termination may include Rho-independent termination or Rho-dependent termination. Rho-independent termination involves a series of U residues preceded by a GC-rich self-complementary region with several intervening nucleotides in the transcribed RNA. The GC-rich self-complementary region may form a stem-loop structure.

In specific embodiments, a TSR does not comprise a polyadenylation sequence, AAUAAA. In some embodiments, a TSR does not comprise or is not a poly(A) tail. In certain embodiments, a TSR is a ribozyme the cleaves the 3' end of a transcript, which may create consistent 3' ends. In particular embodiments, a TSR is not a ribozyme the cleaves the 3' end of a transcript.

In other embodiments, a TSR is not a UTR (e.g., 5' UTR or 3' UTR), or a fragment thereof. In other embodiments, a TSR is not translated. In some embodiments, a TSR is not a coding region of a gene or an mRNA, or fragment thereof. In particular embodiments, a TSR is not a native sequence of a genome (e.g., genome of a human, mouse, rat, monkey, dog, cat, pig, sheep, goat, horse, chicken, frog, worm, insect (e.g., fly), or cow). In specific embodiments, a TSR is not an siRNA or a miRNA, or a precursor thereof.

4.1.4. Promoters Driving Transcription of Target Sequences

In specific embodiments, transcription of a target sequence of a reporter nucleic acid construct described herein is driven by a promoter, i.e., a nucleic acid sequence encoding a target sequence RNA is operably linked to a promoter. One of skill in art would be able to select a suitable promoter for transcription of a target sequence.

In particular embodiments, transcription of a target sequence of a reporter nucleic acid construct described herein is driven by a constitutive promoter. In some embodiments, transcription of a target sequence of a reporter nucleic acid construct described herein is driven by an inducible promoter (e.g., Tet on/off system). In certain embodiments, the promoter driving transcription of a target sequence is not a CTR promoter. In some embodiments, transcription of a target sequence of a reporter nucleic acid construct described herein is driven by a CTR promoter. In certain embodiments, transcription of a target sequence of a reporter nucleic acid construct described herein is driven by a CTR promoter that is different from the CTR promoter operably linked to the ORF of a reporter. In some embodiments, the promoter driving transcription of each of the one or more target sequences are different, respectively. For example, a first promoter drives transcription of TSR1, a second promoter (different from the first promoter) drives transcription of TSR2, etc. In certain embodiments, a promoter driving transcription of a TSR that is not cotranscribed with a reporter can be active in a host cell initially, but as the host cell undergoes a transition in cell fate, e.g., differentiation, dedifferentiation, or trans-differentiation, the promoter becomes inactive in the cellular context of the new cell fate of the host cell.

In some embodiments, transcription of a target sequence may be driven by an RNA polymerase III promoter. In some embodiments, transcription of a target sequence may be driven by an RNA polymerase II promoter. In certain embodiments, the promoter driving transcription of a target sequence is a heterologous promoter. In particular embodiments, the promoter driving transcription of a target sequence comprises or consists essentially of the minimal promoter region. In some embodiments, the promoter driving transcription of a target sequence comprises one or more enhancer elements.

Non-limiting examples of promoters that can be used to drive transcription of one or more target sequences described herein include the cytomegalovirus (CMV) promoter, nuclear T7 promoter, and SV40 early promoter region, the promoter contained in the 3' long terminal repeat of Rous sarcoma virus, the herpes thymidine kinase promoter, and the regulatory sequences of the metallothionein gene.

4.1.5. Cloning Nucleic Acid Constructs

As will be appreciated by those of skill in the art, any methods that are suitable may be used to clone the nucleic acid constructs described herein (see, for example, *Current Protocols in Molecular Biology*, eds. Ausubel et al., John Wiley & Sons: 1992). Various methods employed in the preparation of the constructs and plasmids and in transformation of host cells are well known in the art. For non-limiting examples of suitable expression systems for both host cells, as well as general recombinant procedures, see *Molecular Cloning A Laboratory Manual*, 3rd Ed., ed. by Sambrook, Fritsch and Maniatis (Cold Spring Harbor Laboratory Press, 2001).

Techniques for introducing nucleic acids into cells are well-known and readily appreciated by the skilled worker. The methods include but are not limited to transfection, viral delivery, protein or peptide mediated insertion, coprecipitation methods, lipid based delivery reagents (lipofection), cytofection, lipopolyamine delivery, dendrimer delivery reagents, electroporation or mechanical delivery.

Examples of vectors that may be used to introduce the nucleic acids into host cells include but are not limited to plasmids, viruses, including retroviruses, lentiviruses, adenoviruses, cosmids, and artificial chromosomes. Non-limiting examples of plasmids may include, for example, pCMV-Script, pcDNA3.1 Hygro, pcDNA3.1neo, pcDNA3.1puro, pSV2neo, piRES puro, pSV2 neo. Exemplary mammalian expression vectors that are useful to make the cells and cell lines described herein include: pFN11A (BIND) FLEXI® Vector, pGL4.31, pFC14A HALOTAG® 7 CMV FLEXI® Vector, pFC14K HALOTAG® 7 CMV FLEXI® Vector, pFN24A HALOTAG® 7 CMVd3 FLEXI® Vector, pFN24K HALOTAG® 7 CMVd3 FLEXI® Vector, HALOTAG™ pHT2 Vector, PACT® Vector, PADVANTAGE™ Vector, PALTER®-MAX Vector, pBIND, PCAT® 3-Basic Vector, PCAT® 3-Control Vector, PCAT® 3-Enhancer Vector, Promoter PCAT® 3-Promoter Vector, pCI, pCMVTNT™, pG5luc, pSI, pTARGET™, pTNT™, pF12A RM FLEXI® Vector, pF12K RM FLEXI® Vector, pReg neo, pYES2/GS, pAcYCMVN5-DEST GATEWAY® Vector, pA&PL-DEST™ GATEWAY® Vector, GATEWAY® pDEST™ 27 Vector, GATEWAY® pEF-DEST51 Vector, GATEWAY® pcDNA™-DEST47 Vector, pCMV/Bsd Vector, pEF6/His A, B, & C, pcDNA™ 6.2DEST, pLenti6/TR, pLP-AcGFP1-C, pLPS-AcGFP1-N, pLP-IRESneo, pLP-TRE2, pLP-RevTRE, pLP-LNCX, pLP-CMV-HA, pLP-CMV-Myc, pLP-RetroQ and pLPCMVneo. Another non-limiting example of a plasmid that may be used in the methods described herein is the PB-TET transposon plasmid.

In some embodiments, the vectors comprise expression control sequences such as constitutive or conditional promoters. One of ordinary skill in the art will be able to select such sequences. For example, suitable promoters include but are not limited to CMV, TK, SV40 and EF10. In some embodiments, the promoters are inducible, temperature regulated, tissue specific, repressible, heat-shock, developmental, cell lineage specific, eukaryotic, prokaryotic or temporal promoters or a combination or recombination of unmodified or mutagenized, randomized, shuffled sequences of anyone or more of the above. In other embodiments, the protein of interest, such as a CTR factor, is expressed by gene activation or episomally.

In some embodiments, the vector (e.g., reporter nucleic acid construct) lacks a selectable marker or drug resistance gene. In other embodiments, the vector (e.g., reporter nucleic acid construct) optionally comprises a nucleic acid encoding a selectable marker, such as a protein that confers drug or antibiotic resistance or more generally any product that exerts selective pressure on the cell. Where more than one vector is used, each vector may have the same or a different drug resistance or other selective pressure marker. If more than one of the drug resistance or selective pressure markers are the same, simultaneous selection may be achieved by increasing the level of the drug. Suitable markers are well-known to those of skill in the art and include but are not limited to polypeptides products conferring resistance to anyone of the following: neomycin/G418, puromycin, hygromycin, zeocin, methotrexate and blasticidin. Although drug selection (or selection using any other suitable selection marker) is not a required step in producing the cells and cell lines described herein, it may be used to enrich the transfected cell population for stably transfected cells, provided that the transfected constructs are designed to confer drug resistance. If subsequent selection of cells expressing the protein of interest is accomplished using fluorogenic oligonucleotides, selection too soon following transfection can result in some positive cells that may only be transiently and not stably transfected. However, this effect can be minimized by allowing sufficient cell passage to allow for dilution of transient expression in transfected cells.

4.2 Host Cells

Any host cell suitable for the methods described herein may be used. In specific embodiments, a host cell is a human cell. In certain embodiments, a host cell is not a human cell. In particular embodiments, a host cell is a cell derived from a mouse, rat, monkey, dog, cat, pig, sheep, goat, horse, chicken, frog, worm, insect (e.g., fly), or cow. In some embodiments, a host cell is a mammalian cell, or a eukaryotic cell.

The selection of a particular host cell/CTR combination depends on the cell fate modulator that is to be identified. For example, where it is desired to identify modulators that can induce pluripotent stem cells from fibroblasts, fibroblast host cells comprising a reporter nucleic acid construct comprising an ORF of a reporter operably linked to a pluripotent stem cell CTR promoter, may be chosen for the methods describe herein.

The invention provides for host cells for use in the methods described herein, such as methods for identifying and/or validating modulators of cell fate, e.g., stem cell maintenance, cell specification, cell determination, induction of stem cell fate, cell differentiation, cell dedifferentiation, and cell transdifferentiation. The invention also provides for methods of making and isolating such host cells.

In certain embodiments, the host cells described herein can be transplanted into a mammal, such as a human, mouse, rat, dog, cat, sheep, goat, cow, frog, or monkey. The cells can be used for in vivo assays to assess the biological activities of the modulators described herein in cell fate/cell type specification. The activity of a reporter may be detected in vivo.

In particular embodiments, host cells described herein may be useful for generating new tissue, organs, or whole animals or organisms. For example, fibroblast host cells are engineered to contain a reporter nucleic acid construct comprising a stem cell promoter, and the fibroblast host cells are exposed to conditions to produce iPS cells from the fibroblast host cells. Subsequently, the iPS cells are exposed to conditions to generate a new differentiated cell, new tissue, a new organ, or a whole non-human organism. The host cell may contain a combination of reporter nucleic acid constructs that allow for monitoring or detecting the progression of the host cells from a somatic cell, to an iPS cell, and to a different cell type. The invention relates to methods for generating new tissue, a new organ, or a whole non-human organism from a host cell, such as a somatic host cell induced to become iPS cells. The invention also relates to methods for identifying compounds that can modulate these transition processes. Any engineered cells may be used to generate iPS cells for use in the methods described herein.

In specific embodiments, the invention provides for host cells comprising the reporter nucleic acid constructs described herein, e.g., a nucleic acid construct comprising an ORF encoding a reporter operably linked to a CTR promoter, and a nucleic acid sequence encoding a target sequence. In particular embodiments, host cells described herein comprise two or more reporter nucleic acid constructs, each comprising a ORF encoding a different reporter gene. For example, a first reporter nucleic acid construct comprises a first ORF encoding a first reporter operably linked to a first CTR promoter, and a nucleic acid sequence encoding a first TSR which is cotranscribed with the first reporter; a second reporter nucleic acid construct comprises a second ORF encoding a second reporter operably linked to a second CTR promoter and a nucleic acid sequence encoding a second TSR which is cotranscribed with the second reporter. In certain embodiments, host cells may also comprise three or more reporter nucleic acid constructs described herein.

In specific embodiments, a host cell may comprise more than one different reporter nucleic acid constructs. Each of the different reporter nucleic acid constructs may comprise a different CTR promoter operably linked to an ORF encoding the same reporter. In some embodiments, Each of the different reporter nucleic acid constructs may comprise a different CTR promoter operably linked to an ORF encoding different reporters. For example, host cells may comprise three different reporter nucleic acid constructs, wherein each reporter nucleic acid construct comprises an ORF of the same reporter operably linked to one of three different CTR promoters, such as the Nanog promoter, Oct4 promoter, and c-myc promoter. Multiple groups of CTR promoters may also be used, wherein each group comprises a different reporter. For example, host cells may comprise a first group of CTR promoters transcriptionally regulate a first reporter, and a second group of CTR promoters transcriptionally regulate a second reporter. Host cells may further comprise a third or fourth group of CTR promoters driving expression of a third reporter and fourth reporter, respectively. In specific embodiments, the CTR promoters in the first group are associated with a first cell type, the CTR promoters in the second group are associated with a second cell type, etc. In such system, the same cells may be used to identify compounds involved in involved in achieving a first cell type (e.g., stem cell) as well as in achieving a second cell type (e.g., muscle cell).

In specific aspects, the invention provides for an expression library, wherein a panal of different cells are engineered to comprise one or more of the reporter nucleic acid constructs described herein. Such expression library may be useful for identifying or selecting host cells wherein a CTR promoter is active or inactive. In particular embodiments, an expression library comprises more than 100 different cell types which comprise one or more reporter nucleic acid constructs described herein. In certain embodiments, an expression library comprises at least 3, 4, 5, 6, 7, 8, 9, 10, 11, 12, 13, 14, 15, 16, 17, 18, 19, 20, 30, 40, 50, 60, 70, 75, 80, 90, 100, 125, 150, 175, 200, 250, 300, 400, 500, 600, 700, 800, 900, or 1,000 different cell types which comprise one or more reporter nucleic acid constructs described herein. In some embodiments, an expression library comprises at least 5-10, 5-15, 10-20, 10-40, 20-40, 20-50, 30-60, 40-100, 100-150, 100-200, 100-300, 100-400, 100-500, 200-600, or 500-1,000 different cell types which comprise one or more reporter nucleic acid constructs described herein.

In specific embodiments, host cells of the expression library may be engineered to recombinantly express one or more CTR factors. In specific embodiments, host cells of the expression library may be engineered to recombinantly express one or more CTR factors which are RNAs. The RNAs may be encoded by the reporter nucleic acid constructs introduced into the host cell. For example, a library of reporter nucleic acid constructs are generated so that the reporter nucleic acid constructs comprise (i) a reporter ORF operably linked to a CTR promoter, (ii) sequences encoding one or more TSRs, and (iii) an ORF encoding an test RNA. Each reporter nucleic acid construct of the library encodes for a different test RNA. The activity of the reporter in the host cells is determined, and the test RNA encoded by the reporter nucleic acid construct contained in the host cells with the desired reporter activity is identified. In particular embodiments, the test RNAs are encoded by a different nucleic acid expression construct.

Cells that can be used with the methods described herein are any suitable host cell or cell line, such as eukaryotic cells and cell lines. In some embodiments, host cells are mammalian cell or cell lines. Selection of a suitable host cell depends on various factors. In certain embodiments, it is desirable that the CTR promoter of the reporter nucleic acid construct is not active in a host cell. In another embodiment, it is desirable that the CTR promoter of the reporter nucleic acid construct is active in a host cell.

Non-limiting examples of host cells that may be used in the methods described herein include: Human Embryonic Kidney-293T cells, neuronal cells, established neuronal cell lines, pheochromocytomas, neuroblastomas fibroblasts, rhabdomyosarcomas, dorsal root ganglion cells, NS0 cells, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26), MRC-5 (ATCC CCL 171), L-cells, HEK-293 (ATCC CRL1573) and PC12 (ATCC CRL-1721), HEK293T (ATCC CRL-11268), RBL (ATCC CRL-1378), SH-SY5Y (ATCC CRL-2266), MDCK (ATCC CCL-34), SJ-RH30 (ATCC CRL-2061), HepG2 (ATCC HB-8065), ND7/23 (ECACC 92090903), CHO (ECACC 85050302), Vero (ATCC CCL 81), Caco-2 (ATCC HTB 37), K562 (ATCC CCL 243), Jurkat (ATCC TIB-152), Per.C6 (Crucell, Leiden, The Netherlands), Huvec (ATCC Human Primary PCS 100-010, Mouse CRL 2514, CRL 2515, CRL 2516), HuH-7D12 (ECACC 01042712), 293 (ATCC CRL 10852), A549 (ATCC CCL 185), IMR-90 (ATCC CCL 186), MCF-7 (ATC HTB-22), U-2OS (ATCC HTB-96), T84 (ATCC CCL 248), or any established cell line (polarized or nonpolarized) or any cell line available from repositories such as American Type Culture Collection (ATCC, 10801 University Blvd. Manassas, Va. 20110-2209 USA) or European Collection of Cell Cultures (ECACC, Salisbury Wiltshire SP4 0JG England).

In some embodiments, the host cells that may be used in the methods described herein are stem cells such as embryonic stem cells, cancer stem cells, progenitor cells, somatic cells, myocytes, keratinocytes, fibroblasts, epidermal basal cells, Beta cells (pancreas), hepatocytes, skeletal muscle cells, hepatic stellate cells, heart muscle cells, monocytes, retinal pigment epithelial cells, or dopaminergic neurons. As used herein, stem cells refer to any self-renewing cell that divides to give rise to a cell with an identical developmental potential and/or one with a more restricted developmental potential. Stem cells may include, but are not limited to, totipotent, pluripotent, and multipotent cells. Non-limiting examples of stem cells include ESCs, iPS cells, cancer stem cells, and organ or tissue specific stem cells such as HSCs, neuronal stem cells, eye stem cells, and skin stem cells.

In a certain embodiment, host cells are cells engineered by somatic cell nuclear transfer (SCNT), which is a technique in which the nucleus of a somatic cell, that is any cell of the body apart from the sperm or egg, is transferred into an egg that has had its original nucleus removed. The egg now has the same DNA, or genetic material, as the donor somatic cell. Given the right signals, the egg can be coaxed into developing as if it had been fertilized. The egg would divide to form 2 cells, then 4 cells, then 8 cells and so on until the blastocyst is formed. Embryonic stem cells can be derived from this blastocyst to create cell lines that are genetically identical to the donor somatic cell.

Other non-limiting examples of host cells that may be used in the methods described herein include: epidermal keratinocyte (differentiating epidermal cell), epidermal basal cell (stem cell), keratinocyte of fingernails and toenails, nail bed basal cell (stem cell), medullary hair shaft cell, cortical hair shaft cell, cuticular hair shaft cell, cuticular hair root sheath cell, hair root sheath cell of Huxley's layer, hair root sheath cell of Henle's layer, external hair root sheath cell, hair matrix cell (stem cell), surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, urinary epithelium cell (lining urinary bladder and urinary ducts), salivary gland mucous cell (polysaccharide-rich secretion), salivary gland serous cell (glycoprotein enzyme-rich secretion), von Ebner's gland cell in tongue (washes taste buds), mammary gland cell (milk secretion), lacrimal gland cell (tear secretion), ceruminous gland cell in ear (wax secretion), eccrine sweat gland dark cell (glycoprotein secretion), eccrine sweat gland clear cell (small molecule secretion), apocrine sweat gland cell (odoriferous secretion, sex-hormone sensitive), gland of Moll cell in eyelid (specialized sweat gland), sebaceous gland cell (lipid-rich sebum secretion), bowman's gland cell in nose (washes olfactory epithelium), Brunner's gland cell in duodenum (enzymes and alkaline mucus), seminal vesicle cell (secretes seminal fluid components, including fructose for swimming sperm), prostate gland cell (secretes seminal fluid components), bulbourethral gland cell (mucus secretion), Bartholin's gland cell (vaginal lubricant secretion), gland of Littre cell (mucus secretion), uterus endometrium cell (carbohydrate secretion), isolated goblet cell of respiratory and digestive tracts (mucus secretion), stomach lining mucous cell (mucus secretion), gastric gland zymogenic cell (pepsinogen secretion), gastric gland oxyntic cell (hydrochloric acid secretion), pancreatic acinar cell (bicarbonate and digestive enzyme secretion), paneth cell of small intestine (lysozyme secretion), type II pneumocyte of lung (surfactant secretion), clara cell of lung, anterior pituitary cells, somatotropes, lactotropes, thyrotropes, gonadotropes, corticotropes, intermediate pituitary cell, secreting melanocyte-stimulating hormone, magnocellular neurosecretory cells (secreting oxytocin and/or secreting vasopressin), gut and respiratory tract cells (secreting serotonin, secreting endorphin, secreting somatostatin, secreting gastrin, secreting secretin, secreting cholecystokinin, secreting insulin, secreting glucagons, and/or secreting bombesin), thyroid gland cells, thyroid epithelial cell, parafollicular cell, parathyroid gland cells, parathyroid chief cell, oxyphil cell, adrenal gland cells, chromaffin cells, adrenal gland secreting steroid hormones (mineralcorticoids and gluco corticoids), Leydig cell of testes secreting testosterone, theca interna cell of ovarian follicle secreting estrogen, corpus luteum cell of ruptured ovarian follicle secreting progesterone (Granulosa lutein cells, and Theca lutein cells), juxtaglomerular cell (renin secretion), macula densa cell of kidney, peripolar cell of kidney, mesangial cell of kidney, hepatocyte (liver cell), white fat cell, brown fat cell, liver lipocyte, kidney glomerulus parietal cell, kidney glomerulus podocyte, kidney proximal tubule brush border cell, loop of Henle thin segment cell, kidney distal tubule cell, kidney collecting duct cell, type I pneumocyte (lining air space of lung), pancreatic duct cell (centroacinar cell), nonstriated duct cell (of sweat gland, salivary gland, mammary gland, etc.) such as principal cell and intercalated cell, duct cell (of seminal vesicle, prostate gland, etc.), intestinal brush border cell (with microvilli), exocrine gland striated duct cell, gall bladder epithelial cell, ductulus efferens nonciliated cell, epididymal principal cell, epididymal basal cell, blood vessel and lymphatic vascular endothelial fenestrated cell, blood vessel and lymphatic vascular endothelial continuous cell, blood vessel and lymphatic vascular endothelial splenic cell, synovial cell (lining joint cavities, hyaluronic acid secretion), serosal cell (lining peritoneal, pleural, and pericardial cavities), squamous cell (lining perilymphatic space of ear), squamous cell (lining endolymphatic space of ear), columnar cell of endolymphatic sac with microvilli (lining endolymphatic space of ear), columnar cell of endolymphatic sac without microvilli (lining endolymphatic space of ear), dark cell (lining endolymphatic space of ear), vestibular membrane cell (lining endolymphatic space of ear), stria vascularis basal cell (lining endolymphatic space of ear), stria vascularis marginal cell (lining endolymphatic space of ear), cell of Claudius (lining endolymphatic space of ear), cell of Boettcher (lining endolymphatic space of ear), choroid plexus cell (cerebrospinal fluid secretion), pia-arachnoid squamous cell, pigmented ciliary epithelium cell of eye, nonpigmented ciliary epithelium cell of eye, corneal endothelial cell, respiratory tract ciliated cell, oviduct ciliated cell (in female), uterine endometrial ciliated cell (in female), rete testis ciliated cell (in male), ductulus efferens ciliated cell (in male), ciliated ependymal cell of central nervous system (lining brain cavities), ameloblast epithelial cell (tooth enamel secretion), planum semilunatum epithelial cell of vestibular apparatus of ear (proteoglycan secretion), organ of Corti interdental epithelial cell (secreting tectorial membrane covering hair cells), loose connective tissue fibroblasts, corneal fibroblasts (corneal keratocytes), tendon fibroblasts, bone marrow reticular tissue fibroblasts, other nonepithelial fibroblasts, pericyte, nucleus pulposus cell of intervertebral disc, cementoblast/cementocyte (tooth root bonelike cementum secretion), ontoblast/odontocyte (tooth dentin secretion), hyaline cartilage chondrocyte, fibrocartilage chondrocyte, elastic cartilage chondrocyte, oteoblast/osteocyte, osteoprogenitor cell (stem cell of osteoblasts), hyalocyte of vitreous body of eye, stellate cell of perilymphatic space of ear, hepatic stellate cell (Ito cell), pancreatic stellate cell, skeletal muscle cells (such as Red skeletal muscle cell (slow), white skeletal muscle cell (fast), intermediate skeletal muscle cell, nuclear bag cell of muscle spindle, and nuclear chain cell of muscle spindle), satellite cell (stem cell), heart muscle cells (such as ordinary heart muscle cell, nodal heart muscle cell, and purkinje fiber cell), smooth muscle cell (various types), myoepithelial cell of iris, myoepithelial cell of exocrine glands, erythrocyte (red blood cell), megakaryocyte (platelet precursor), monocytes, connective tissue macrophage (various types), epidermal Langerhans cell, osteoclast (in bone), dendritic cell (in lymphoid tissues), microglial cell (in central nervous system), neutrophil granulocyte, eosinophil granulocyte, basophil granulocyte, mast cell, helper T cell, suppressor T cell, cytotoxic T cell, natural Killer T cell, B cell, natural killer cell, reticulocyte, stem cells and committed progenitors for the blood and immune system (various types), auditory outer hair cell of organ of Corti, basal cell of olfactory epithelium (stem cell for olfactory neurons), cold-sensitive primary sensory neurons, heat-sensitive primary sensory neurons, merkel cell of epidermis (touch sensor), olfactory receptor neuron, pain-sensitive primary sensory neurons (various types), photoreceptor cells of retina in eye (such as photoreceptor rod cells, photoreceptor blue-sensitive cone cell of eye, photoreceptor green-sensitive cone cell of eye, photoreceptor red-sensitive cone cell of eye), proprioceptive primary sensory neurons (various types), touch-sensitive primary sensory neurons (various types), type I carotid body cell (blood pH sensor), type II carotid body cell (blood pH sensor), type I hair cell of vestibular apparatus of ear (acceleration and gravity), type II hair cell of vestibular apparatus of ear (acceleration and gravity), type I taste bud cell, cholinergic neural cell (various types), adrenergic neural cell (various types), peptidergic neural cell (various types), inner pillar cell of organ of Corti, outer pillar cell of organ of Corti, inner phalangeal cell of organ of Corti, outer phalangeal cell of organ of Corti, border cell of organ of Corti, hensen cell of organ of Cortim vestibular apparatus supporting cell, type I taste bud supporting cell, olfactory epithelium supporting cell, schwann cell, satellite cell (encapsulating peripheral nerve cell bodies), enteric glial cell, astrocyte (various types), neuron cells (large variety of types, still poorly classified), oligodendrocyte, spindle neuron, anterior lens epithelial cell, crystallin-containing lens fiber cell, melanocyte, retinal pigmented epithelial cell, oogonium/oocyte, spermatid, spermatocyte, spermatogonium cell (stem cell for spermatocyte), spermatozoon, ovarian follicle cell, sertoli cell (in testis), thymus epithelial cell, and interstitial kidney cells.

In specific embodiments, a host cell is a fibroblast cell comprising a reporter nucleic acid construct described herein, e.g., reporter nucleic acid construct comprising an ORF encoding a reporter, which ORF is operably linked to a CTR promoter, and a nucleic acid sequence encoding one or more target sequence, and the CTR promoter comprises a region of the promoter of Oct4, Sox2, Klf4, c-myc, LIN28, Nanog, SSEA-3, or SSEA-4. Such host cell may be useful for methods of identifying and/or validating modulators of induced pluripotent stem cells.

In some embodiments, host cells are stem cells (e.g., ESCs) comprising a reporter nucleic acid construct described herein, and the CTR promoter of the nucleic acid construct comprises a region of the promoter of Oct4, Sox2, Klf4, c-myc, LIN28, Nanog, SSEA-3, or SSEA-4. Such host cells may be useful for methods of identifying and/or validating modulators for stem cell maintenance, such as self-renewal, growth, and/or proliferation.

In certain embodiments, host cells are stem cells comprising a reporter nucleic acid construct described herein, and the CTR promoter of the reporter nucleic acid construct comprises a region of a differentiation marker promoter (e.g., a promoter for cell-type specific or cell-type associated gene). Such host cells may be useful for methods of identifying and/or validating modulators of cell differentiation. For example, where the host cells are stem cells and the CTR promoter is a promoter of a differentiation marker, the basal expression level of the reporter is low or not detectable, and positive modulators of differentiation will be able to increase or induce expression of the reporter relative to expression in the host cells in the absence of the positive modulators.

In particular embodiments, the host cells are differentiated cells comprising a reporter nucleic acid construct described herein, and the CTR promoter of the nucleic acid construct comprises a region of a promoter of a differentiation marker. In other embodiments, the host cells are differentiated cells comprising a reporter nucleic acid construct described herein, and the CTR promoter is a promoter of a stem cell marker. Such host cells may be useful in methods related to dedifferentiation.

In certain aspects relating to cell transdifferentiation from a first cell type to a second cell type, host cells are differentiated cells of a first cell type comprising a reporter nucleic acid construct described herein, and the CTR promoter of the reporter nucleic acid construct comprises a region of a promoter of a gene that is a differentiation marker of a specific second cell type, e.g., skin cell, myocyte, fibroblast, or pancreatic Beta cells. For example, where the host cells are differentiated skin cells and the CTR promoter is a promoter of a differentiation marker of neurons, the basal expression level of the reporter is low in the host differentiated skin cells, and positive modulators of transdifferentiation into neurons will be able to increase or induce expression of the reporter relative to expression in the host cells in the absence of the positive modulators of transdifferentiation.

In particular embodiments, host cells are engineered to express one or more CTR factors, which may provide the cellular context in the host cells for stem cell maintenance (e.g., self-renewal, growth and/or proliferation), cell differentiation, cell dedifferentiation, or cell transdifferentiation. In other embodiments, host cells are engineered to express one or more CTR factors, which may provide the cellular context in the host cells for inducing pluripotent stem cells.

In particular embodiments, the host cell are primary cells. In other embodiments, the host cells are cell lines. In certain embodiments, the host cells are transiently transfected with the reporter nucleic acid construct. In particular embodiments, the host cells are stable cells comprising the reporter nucleic acid construct. In specific embodiments, the host cells comprises the reporter nucleic acid construct described herein, wherein the reporter nucleic acid construct has been stably integrated into the genome of the host cells. In specific embodiments, a host cell stably expresses RNAs or proteins of interests, e.g., reporters or CTR factors. In certain embodiments, host cells or cell lines described herein, e.g., host cells comprising a reporter nucleic acid construct and optionally one or more CTR factors such as RNAs or proteins, are stable with less than 30% variation over 3 or more months, with and without selection pressure.

As will be appreciated by those of skill in the art, any vector and method that are suitable for use with a chosen host cell may be used to introduce a nucleic acid construct of interest into a cell. In specific embodiments, the nucleic acid constructs described herein may be introduced into the cells by liposomal methods, such as OLIGOFECTAMINE™ transfection reagent, TFX™ transfection reagents, DOTAP/DOPE, METAFECTENE® transfection reagent, Fecturi, LIPOFECTAMINE™ transfection reagent, LIPOFECTAMINE™ 2000 transfection reagent, and FUGENE® 6 transfection reagent.

Host cells may be selected that have desirable properties for use in the methods described herein. Any desired property that can be detected may be selected for. Those of skill in the art will aware of such characteristics. By way of non-limiting example, such properties include: fragility, morphology and adherence to a solid surface, monodispersion by trypsin or cell dissociation reagent, adaptability to the automated culture conditions, performance under serum-containing conditions, performance in serum-free conditions, convertability to serum-free suspension conditions, propensity to form clumps, propensity to form monodisperse cell layers following passaging, resilience, propensity to remain attached to growth chamber surfaces under fluid addition of different force, non-fragmented nucleus, lack of intracellular vacuoles, lack of microbial contamination, lack of mycoplasma, lack of viral contamination, clonality, consistency of gross physical properties of cells within wells, propensity for growth below/at/above room temperature, propensity for tolerance of various temperatures for various time periods, propensity of cells to evenly uptake plasmid/oligonucleotides/fluorogenic oligonucleotides/peptides/proteins/compounds, propensity of cells to withstand incubation with OMSO/EtOH/MeOH, organic solvent/detergent, propensity of cells to withstand maintained UPR induction, propensity of cells to withstand exposure to OTT, propensity of cells to be infected with viral/lentiviral/cosmid vectors, endogenous expression of desired RNA(s)/protein(s) or lack thereof, chromosomal number, chromosomal aberrations, amenable to growth at 5/6/7/8/9 pH, tolerance to UV/mutagen/radiation, ability to maintain the above characteristics under altered/manual/scaled-up growth conditions (i.e., including reactors).

4.2.1. CTR Factors

The invention provides for host cells comprising a reporter nucleic acid construct described herein for use in methods for identifying and/or validating modulators of cell fate/cell type specification. In specific aspects, additional CTR factors may cooperate with other factors or agents to modulate cell fate/cell type specification, e.g., stem cell maintenance and proliferation, cell differentiation, transdifferentiation, or dedifferentiation. In specific embodiments, cells lacking (e.g., cells that do not endogenously express) a CTR factor are not capable of maintaining or changing cell type in response to certain conditions or compounds. Specific combinations of CTR factors may provide a cellular context that allows for modulation of cell fate/cell-type specification by compounds. For example, certain host cells may not endogenously express one or more CTR factors so that contacting such host cells with a compound does not have an effect; and engineering such host cells to recombinantly express one or more CTR factors to provide a cellular context so that contacting the host cells with a compound has an effect, such as induction of increase in CTR promoter activity or expression of the reporter, promotion of stem cell maintenance, or promotion of cell differentiation, dedifferentiation or transdifferentiation. Certain embodiments, host cells may endogenously express a few CTR factors, but not a sufficient amount or combination of CTR factors for achieving the desired effect with a compound.

CTR factors described herein may be polypeptides or polynucleotides (e.g., DNA or RNA) that can modulate cell fate/cell type specification. In certain embodiments, CTR factors are RNAs that are important for maintaining or changing cell type. Non-limiting examples of such RNAs include messenger RNAs that encode proteins; antisense RNA; small interfering RNA (siRNA); miRNAs; structural RNAs; cellular RNAs (e.g., ribosomal RNAs, tRNAs, hnRNA, and snRNA); random RNAs; RNAs corresponding to cDNAs or ESTs; RNAs that may be incorporated into various macromolecular complexes; RNAs that are ribozymes; RNAs corresponding to viral or foreign RNAs, linker RNA, or sequence that links one or more RNAs; or RNAs that do not have the aforementioned function or activity but which may be expressed by cells nevertheless.

In some embodiments, CTR factors are small molecules. In certain embodiments, the CTR factor is not endogenously expressed in the host cell. In specific embodiments, the CTR factor is exogenously or recombinantly expressed in the host cell. In specific embodiments, CTR factors that are polypeptides are soluble (e.g., secreted), cell membrane bound, or intracellular polypeptides. In particular embodiments, CTR factors that are polypeptides are human CTR factors or murine CTR factors. For example, CTR factors secreted from a host cell may have activity on the cells in the same culture.

Thus, the invention provides for host cells that comprises a reporter nucleic acid construct described herein, and a recombinant nucleic acid construct encoding one or more CTR factors. In certain embodiments, the host cells, comprising a reporter nucleic acid construct described herein, further comprises two or more nucleic acid constructs, each encoding a different CTR factor, respectively. In specific embodiments, the host cell comprising a reporter nucleic acid construct described herein, further comprises recombinant nucleic acid construct(s) encoding 1, 2, 3, 4, 5, 6, 7, 8, 9, 10, 11, 12, 13, 14, 15, 16, 17, 18, 19, 20, or more CTR factors. In specific embodiments, the host cells are selected so that they express one or more of these CTR factors. In particular embodiments, host cells, comprising a reporter nucleic acid construct described herein, recombinantly express one or more CTR factors. In particular embodiments, host cells, comprising a reporter nucleic acid construct described herein, endogenously express one or more CTR factors. In particular embodiments, host cells, comprising a reporter nucleic acid construct described herein, do not endogenously express one or more CTR factors.

In certain embodiments, provided herein is a host cell that comprises a reporter nucleic acid construct, wherein the host cell has been engineered to express one or more CTR factors.

In certain embodiments, the host cell has been engineered to recombinantly express about 10%, 20%, 25%, 30%, 33%, 40%, 50%, 60%, 66%, 70%, 75%, 80%, 90%, 95%, 98%, 99%, or 100% of the CTR factors that are sufficient for the specification or determination or differentiation of the host cell into a particular cell type of interest. In certain embodiments, the host cell has been engineered to recombinantly express about 1, 2, 3, 4, 5, 6, 7, 8, 9, 10, 11, 12, 13, 14, 15, 16, 17, 18, 19, 20, or more of the CTR factors for the specification or determination or differentiation of the host cell into a particular cell type of interest. In particular, the host cell has been engineered to express about 10%, 20%, 25%, 30%, 33%, 40%, 50%, 60%, 66%, 70%, 75%, 80%, 90%, 95%, 98%, 99%, or 100% of the CTR factors that are sufficient to activate the CTR promoter comprised in the reporter nucleic acid construct. In particular, the host cell has been engineered to express about 1, 2, 3, 4, 5, 6, 7, 8, 9, 10, 11, 12, 13, 14, 15, 16, 17, 18, 19, 20, or more of the CTR factors that are sufficient to activate one or more CTR promoters comprised in the reporter nucleic acid construct. A cell can be engineered to express a CTR factor by any technique known to the skilled artisan, such as gene activation (see, e.g., International Patent Application Publication No. WO 94/012650) or transgene technology.

In some embodiments, a CTR factor is involved in stem cell maintenance or proliferation, cell differentiation, cell dedifferentiation, or cell transdifferentiation. In particular embodiments, a combination of CTR factors recombinantly expressed by host cells are involved in stem cell maintenance or proliferation, cell differentiation, cell dedifferentiation, or cell transdifferentiation.

In specific embodiments, the CTR factor may induce or enhance the activity of the CTR promoter in cooperation with other factors or modulators. In certain embodiments, the CTR factor is involved in transcriptional regulation. In one embodiment, the CTR factor is involved in inducing or increasing transcription of a gene. In another embodiment, the CTR factor is involved in inhibiting or decreasing transcription of a gene.

In certain embodiments, the CTR factor may be involved in methylation, acetylation or deacetylation, e.g., histone acetylation or deacetylation. In particular embodiments, the CTR factor may be involved in RNA stability.

In particular embodiments relating to modulators of induced pluripotent stem cells, CTR factors may include, but are not limited to, Oct4, Sox2, Klf4, c-myc, LIN28, and Nanog.

In some embodiments relating to modulators of hair follicle (bulge) stem cell, CTR factors may include, but are not limited to, NFATc1, Sox9, TCF3, and Lhx2.

In some embodiments relating to modulators of epidermal basal cell, CTR factors may include, but are not limited to, c-rel, RelA, Delta1, and Fringe.

In some embodiments relating to modulators of epithelial stem cell, CTR factors may include, but are not limited to Bmi-1, Tcf-4, and β-catenin.

In certain embodiments relating to modulators of skin tissue cells, CTR factors may include, but are not limited to, NFATc1, SOX9, TCF3, LHX2, CD200, K15, ID2, DKK3, WIF1, FZD1, FZD2, PHLDA1, FOLLISTATIN, DIO2, LCE2B, ASPRV1, DEFB4, PI3, RNASE7, K19, ITGB1, REL, RELA, DLL1, BMI1, TCF4, CTNNB1, MC1R, SLC45A2, and SLC24A5.

In some embodiments relating to modulators of Beta cell (pancreas), CTR factors may include, but are not limited to Mnx1, Pdx1, Nkx6-1, Nkx2-2, Math, Mafa, and Slc2a2.

In some embodiments relating to modulators of hepatocytes, CTR factors may include, but are not limited to Prox1, Rex3, WT1, C/EBP alpha and beta, HNF-1, and HNF-4.

In some embodiments relating to modulators of skeletal muscle cells, CTR factors may include, but are not limited to MyoD, Myf5, myogenin, Mrf4, Mef2, and MURC.

In some embodiments relating to modulators of hepatic stellate cells, CTR factors may include, but are not limited to Foxl1, PPARgamma, and Egr-1.

In some embodiments relating to modulators of muscle stem cells, CTR factors may include, but are not limited to, MyoD, Pax7, Runx2, and Myf5.

In some embodiments relating to modulators of heart muscle cells, CTR factors may include, but are not limited to, Nkx2.5, MEF2C, GATA4, ACTN2, ADBR1, AFP, ALK3, ALK6, ANKRD1, ATF2, BMPR2, CKM, CMYA, COL3A1, CSRP3, CVD1, CXCL14, DCN, DES, DNM3, FGB, GATA4, GATA4, HSBP7, ISL1, KCNG2, KCNIP2, KCNJ2, KCNJ5, LDB3, LUM, MEF2C, MGP, MLC2v, MYBPC3, MYH6, MYH7, MYL3, MYL7, MYLK3, MYOCD, MYOM1, MYOZ2, NPPA, NPPB, PLN, RYR2, SLC4A3, SMAD1, SMAD5, SMAD8, SMPX, SYNPO2L, TAK1, TBX5, TBX5, TNNI1, TNNI3K, and TNNT2.

In some embodiments relating to modulators of monocytes, CTR factors may include, but are not limited to, PU.1, C/EBPalpha, AML1, RARalpha, MZF-1, Hox, and STAT.

In some embodiments relating to modulators of retinal pigment epithelial cells, CTR factors may include, but are not limited to, microphthalmia and ELF3.

In certain embodiments relating to modulators of cells from the eye, CTR factors may include, but are not limited to, RPE65, ABCA4, COL11A1, GNAT2, RHO, GNB3, GNAT1, GNGT1, PDE6A, PDE6B, PDE6G, CNGA1, CNGB1, RCVN, SAG, GUCA1A, SLC24A1, NRG4, ABCA4, PRPH2, ROM1, RDH5, TTR, BEST1, CTSD, CST3, HMCN1, RD3, EFEMP1, ALMS1, CNGA3, CNNM4, MERTK, ARR3, PDE6H, CPLX4, OPA1, MPP4, NRL, CLUL1, RDH12, RBP3, PDC, CRX, IMPG1, RAX, RTBDN, RP1, CRABP1, RLBP1, RS1, STRA13, PROM1, LRAT, TULP1, GUCY2D, VSX1, RGS16, NR2E3, GUCY2F, AOC2, RGR, RDH11, FSCN2, POU6F2, SLC1A7, SLC24A1, ZNF385A, SDR16C5, HSD17B14, DHRS7, SLC24A2, PITPNC1, ALDH1A1, ALDH1A2, and ALDH1A3.

In some embodiments relating to modulators of mesenchymal stem cells, CTR factors may include, but are not limited to, ETV1, ETV5, FOXP1, GATA6, HMGA2, SIM2, and SOX11.

In some embodiments relating to modulators of neural stem cells, CTR factors may include, but are not limited to PLZF, PLAGL1, Dach1, Foxg1, and NR2F1.

In some embodiments relating to modulators of dopaminergic neurons, CTR factors may include, but are not limited to, Otx2, Lmx1a, Ngn2, Fox2a, Pitx3, engrailed, and Nurr1.

In some embodiments relating to modulators of hematopoietic stem cells, CTR factors include, but are not limited to, Evi1, GATA-2, EGR1, and Gfi-1.

In some embodiments relating to modulation of eye specific promoters, Lhx2 and Pax6 are CTR factors that bind to the promoter of Six6 (NP_031400) (see, e.g., Tétreault et al., Dev. Biol., 2009, 327(2):541-50).

In some embodiments relating to modulation of skin stem cells (bulge cells), NFATc1 is a CTR factor that represses the CDK4 promoter (NM_000075). In certain embodiments relating to modulation of skin stem cells (bulge cells), Sox9 is a CTR factor that activates the MITF promoter (microphthalmia-associated transcription factor isoform 2, NP_937820). In particular embodiments relating to modulation of skin stem cells (bulge cells), TCF3 is a CTR factor that activates the CDKN1A promoter (NP_000380).

In certain embodiments, host cells are engineered to recombinantly express any combination of such CTR factors, or fragments or derivatives thereof, that will provide the desired cellular context for the methods described herein.

One of skill in the art would be able to determine the right combination of CTR factors for use in the methods described herein. For example, host cells are introduced with one CTR factor or different combinations of CTR factors and are assayed for the desired properties or cellular context, e.g., expression of cell-type specific markers, CTR promoter activity, and/or morphology. In specific embodiments, introduction of one CTR factor, or a combination of two, three, or four CTR factors to the host cells achieves the desired properties or cellular context. In specific embodiments, the methods for screening CTR factors comprise the steps of (i) introducing to a host cell, different combinations of two or more CTR factors, and (ii) determining the presence of one or more desired properties or cellular context.

Techniques for introducing nucleic acids into cells are well-known and readily appreciated by the skilled worker. The methods include but are not limited to transfection, viral delivery, protein or peptide mediated insertion, coprecipitation methods, lipid based delivery reagents (lipofection), cytofection, lipopolyamine delivery, dendrimer delivery reagents, electroporation or mechanical delivery.

Examples of vectors that may be used to introduce nucleic acids encoding one or more CTR factors into host cells include but are not limited to plasmids, and viruses, including retroviruses, lentiviruses, adenoviruses, cosmids, and artificial chromosomes. Non-limiting examples of plasmids are described above. Isolated nucleic acid constructs encoding one or more CTR factors may comprise a nucleic acid sequence encoding a target sequence RNA, which is complementary to a fluorogenic oligonucleotide. Such target sequence can be used for selection of host cells recombinantly expressing the CTR factors.

Host cells and cell lines recombinantly expressing one or more CTR factors described herein may have enhanced properties as compared to cells and cell lines made by conventional methods. For example, the host cells and cell lines described herein have enhanced stability of expression and/or levels of expression of one or more CTR factors (even when maintained in cultures without selective pressure, including, for example, antibiotics and other drugs). In still other embodiments, the host cells and cell lines recombinantly expressing one or more CTR factors described herein are improved in the context of their expression of a physiologically relevant protein activity as compared to more conventionally engineered cells. These properties enhance and improve the ability of the host cells and cell lines recombinantly expressing one or more CTR factors described herein to be used for any use, whether in assays to identify modulators, for cell therapy, for protein production or any other use and improve the functional attributes of the identified modulators.

In various embodiments, the host cells or cell lines described comprise the nucleic acid construct of interest or express a functional CTR factor RNA or protein of interest, i.e., the cells are consistently functional after growth for at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200 days or over 200 days, where consistent expression or consistently functional refers to a level of expression that does not vary by more than: 1%, 2%, 3%, 4%, 5%, 6%, 7%, 8%, 9% or 10% over 2 to 4 days of continuous cell culture; 1%, 2%, 4%, 6%, 8%, 10% or 12% over 5 to 15 days of continuous cell culture; 1%, 2%, 4%, 6%, 8%, 10%, 12%, 14%, 16%, 18% or 20% over 16 to 20 days of continuous cell culture; 1%, 2%, 4%, 6%, 8%, 10%, 12%, 14%, 16%, 18%, 20%, 22%, 24% over 21 to 30 days of continuous cell culture; 1%, 2%, 4%, 6%, 8%, 10%, 12%, 14%, 16%, 18%, 20%, 22%, 24%, 26%, 28% or 30% over 30 to 40 days of continuous cell culture; 1%, 2%, 4%, 6%, 8%, 10%, 12%, 14%, 16%, 18%, 20%, 22%, 24%, 26%, 28% or 30% over 41 to 45 days of continuous cell culture; 1%, 2%, 4%, 6%, 8%, 10%, 12%, 14%, 16%, 18%, 20%, 22%, 24%, 26%, 28% or 30% over 45 to 50 days of continuous cell culture; 1%, 2%, 4%, 6%, 8%, 10%, 12%, 14%, 16%, 18%, 20%, 22%, 24%, 26%, 28%, 30% or 35% over 45 to 50 days of continuous cell culture; 1%, 2%, 4%, 6%, 8%, 10%, 12%, 14%, 16%, 18%, 20%, 22%, 24%, 26%, 28% or 30% or 35% over 50 to 55 days of continuous cell culture; 1%, 2%, 4%, 6%, 8%, 10%, 12%, 14%, 16%, 18%, 20%, 22%, 24%, 26%, 28%, 30% or 35% over 50 to 55 days of continuous cell culture; 1%, 2%, 3%, 4%, 5%, 10%, 15%, 20%, 25%, 30%, 35% or 40% over 55 to 75 days of continuous cell culture; 1%, 2%, 3%, 4%, 5%, 5%, 10%, 15%, 20%, 25%, 30%, 35%, 40% or 45% over 75 to 100 days of continuous cell culture; 1%, 2%, 3%, 4%, 5%, 5%, 10%, 15%, 20%, 25%, 30%, 35%, 40% or 45% over 101 to 125 days of continuous cell culture; 1%, 2%, 3%, 4%, 5%, 5%, 10%, 15%, 20%, 25%, 30%, 35%, 40% or 45% over 126 to 150 days of continuous cell culture; 1%, 2%, 3%, 4%, 5%, 5%, 10%, 15%, 20%, 25%, 30%, 35%, 40% or 45% over 151 to 175 days of continuous cell culture; 1%, 2%, 3%, 4%, 5%, 5%, 10%, 15%, 20%, 25%, 30%, 35%, 40% or 45% over 176 to 200 days of continuous cell culture; 1%, 2%, 3%, 4%, 5%, 5%, 10%, 15%, 20%, 25%, 30%, 35%, 40% or 45% over more than 200 days of continuous cell culture.

4.2.2. Methods for Making Cells

In particular aspects, the invention relates to a method for making cells described herein comprising one or more reporter nucleic acid constructs. In specific embodiments, a method for making a host cell comprises the steps of: (a) introducing into a cell a reporter nucleic acid construct comprising (i) an ORF encoding a reporter wherein the ORF is operably linked to a CTR promoter, and (ii) a nucleic acid sequence encoding one or more TSR; (b) introducing into the cell fluorogenic oligonucleotides that are complementary to the TSR; and (c) selecting cells that transcribe the TSR. In particular embodiments, such method comprises introducing into a cell two or more reporter nucleic acid constructs, wherein each reporter nucleic acid construct comprises a different ORF encoding a different reporter, wherein each ORF is operably linked to a different CTR promoter.

In particular aspects, the invention relates to a method for making a host cell comprising the steps of: (a) introducing into a cell a reporter nucleic acid construct comprising (i) an ORF encoding a reporter wherein the ORF is operably linked to a CTR promoter, and (ii) a nucleic acid sequence encoding TSR1, TSR2, and TSR3, wherein TSR3 is cotranscribed with the reporter; (b) introducing into the cell fluorogenic oligonucleotides that are complementary to TSR1, TSR2, and TSR3; and (c) selecting cells that transcribe TSR1 and TSR2, and that do not transcribe TSR3 above background levels. In specific embodiments, transcription of TSR1 and TSR2 is driven by a constitutive promoter different from the CTR promoter, and flank the reporter ORF and the CTR promoter. Cells that transcribe TSR1 and TSR2 and do not transcribe TSR3 above background levels should contain the reporter nucleic acid construct wherein the CTR promoter is not active above background levels, since TSR3 is cotranscribed with a reporter under the control of the CTR promoter, and TSR1 and TSR2 are transcribed by different promoters. Without being bound by any particular theory, host cells with such characteristics are useful in methods for identifying and/or validating modulators that can activate a CTR promoter or that can modulate the cellular context of the host cells so that the activity of the CTR promoter is induced or increased. Use of cells with a lower basal CTR promoter activity, than cells made by conventional methods, allows for more sensitive assays for identifying and/or validating positive modulators, and for selecting the desired cellular context/condition for identifying and/or validating modulators of cell fate such as maintenance, cell specification, cell determination, induction of stem cell fate, cell differentiation, cell dedifferentiation, and cell trans-differentiation.

In specific embodiments, the CTR promoter of the reporter nucleic acid construct is a stem cell promoter, such as the Oct4 promoter, Sox2 promoter, Klf4 promoter, c-myc promoter, LIN28 promoter, Nanog promoter, SSEA-3 promoter, SSEA-4 promoter, or any stem cell promoter known in the art. Non-limiting examples of CTR promoters such as stem cell promoters are described herein in section 4.1.2. In particular embodiments, the CTR promoter of the reporter nucleic acid construct is a differentiation marker promoter. For example, the host cells may be stem cells or cancer stem cells wherein the differentiation marker promoter is not active above background levels, and the host cells are exposed to conditions and/or compounds that are capable of inducing or increasing the activity of the differentiation marker promoter in the host cells. Such conditions and/or compounds can be modulators of differentiation of stem cells or cancer stem cells.

In certain embodiments, the invention relates to a method for making a host cell comprising the steps of: (a) introducing into a cell a reporter nucleic acid construct comprising (i) an ORF encoding a reporter wherein the ORF is operably linked to a CTR promoter, and (ii) a nucleic acid sequence encoding TSR1, TSR2, and TSR3, wherein TSR3 is cotranscribed with the reporter; (b) introducing into the cell fluorogenic oligonucleotides that are complementary to TSR1, TSR2, and TSR3; and (c) selecting cells that transcribe TSR1, TSR2, and TSR3. In specific embodiments, transcription of TSR1 and TSR2 is driven by a constitutive promoter different from the CTR promoter, which drives transcription of the report and TSR3. Host Cells that transcribes TSR3 have a CTR promoter that is active under such cellular context, which host cells may be useful for identifying and/or validating modulators that inhibit or decrease the CTR promoter activity or modulators of cell fate.

In further embodiments, the method for making host cells described herein further comprises the step of introducing into the host cell recombinant nucleic acids encoding one or more CTR factors, such as those described in section 4.2.1. Without being bound by any particular theory, recombinant expression of one or more CTR factors by host cells may be necessary for a compound to modulate activity of the CTR promoter or to modulate cell fate/cell-type specification. For example, a host cell may lack expression of a CTR factor that is necessary for a compound to modulate activity of the CTR promoter or to modulate cell fate/cell-type specification, and thus, introduction of such CTR factor or nucleic acid constructs encoding such CTR factor into the host cell, allow for detection of the effect of a compound. In certain embodiments, expression of one or more CTR factors in a host cell is achieved via gene activation.

In certain embodiments, the method for making host cells described herein further comprises the step of exposing the host cell to one or more CTR factors which may provide suitable conditions for modulation of CTR promoter activity or cell fate such as maintenance, cell specification, cell determination, induction of stem cell fate, cell differentiation, cell dedifferentiation, and cell trans-differentiation.

Techniques for introducing nucleic acids (e.g., reporter nucleic acid constructs and recombinant nucleic acid constructs encoding CTR factors) into cells are well-known and readily appreciated by the skilled worker. The methods include but are not limited to transfection, viral delivery, protein or peptide mediated insertion, coprecipitation methods, lipid based delivery reagents (lipofection), cytofection, lipopolyamine delivery, dendrimer delivery reagents, electroporation or mechanical delivery. Examples of viral delivery systems include but are not limited to retroviruses, lentiviruses, and adenoviruses. In certain embodiments, gene activation may be used for expression of one or more CTR factors in a host cell.

To make host cells and cell lines described herein, one can use, for example, the technology described in U.S. Pat. No. 6,692,965 and WO/2005/079462. Both of these documents are incorporated herein by reference in their entirety. This technology provides real-time assessment of millions of cells such that any desired number of clones (from hundreds to thousands of clones). Using cell sorting techniques, such as flow cytometric cell sorting (e.g., with a FACS machine) or magnetic cell sorting (e.g., with a MACS machine), one cell per well is automatically deposited with high statistical confidence in a culture vessel (such as a 96 well culture plate). The speed and automation of the technology allows multi-gene recombinant cell lines to be readily isolated.

4.2.3. Cell Culture Conditions

According to the methods described herein, host cells are cultured under a desired set of culture conditions. In particular embodiments, the cell culture conditions are suitable for the CTR promoter in host cells to be active. In other embodiments, the cell culture conditions are suitable for the CTR promoter in host cells to be inactive. In some embodiments, the cell culture conditions are suitable for modulating (e.g., inducing/increasing or inhibiting/decreasing) the activity of the CTR promoter in host cells.

In specific embodiments, host cells such as stem cells are exposed to stem cell maintenance cell culture conditions. In some embodiments, host cells are exposed to cell differentiation cell culture conditions, such as myocyte differentiation cell culture conditions. In particular embodiments, host cells are exposed to cell dedifferentiation culture conditions. In certain embodiments, host cells such as fibroblasts are exposed to cell culture conditions suitable for inducing pluripotent stem cells. In other embodiments, host cells are exposed to cell transdifferentiation culture conditions.

The conditions can be any desired conditions. Those of skill in the art will understand what parameters are comprised within a set of culture conditions. For example, culture conditions include but are not limited to: the media (Base media (DMEM, MEM, RPMI, serum-free, with serum, fully chemically defined, without animal-derived components), mono and divalent ion (sodium, potassium, calcium, magnesium) concentration, additional components added (amino acids, antibiotics, glutamine, glucose or other carbon source, HEPES, channel blockers, modulators of other targets, vitamins, trace elements, heavy metals, co-factors, growth factors, anti-apoptosis reagents), fresh or conditioned media, with HEPES, pH, depleted of certain nutrients or limiting (amino acid, carbon source)), level of confluency at which cells are allowed to attain before split/passage, feeder layers of cells, or gamma-irradiated cells, $CO_2$, a three gas system (oxygen, nitrogen, carbon dioxide), humidity, temperature, still or on a shaker, and the like, which will be well known to those of skill in the art.

The cell culture conditions may be chosen for convenience or for a particular desired use of the cells. Advantageously, the invention provides host cells and cell lines that are optimally suited for a particular desired use. That is, in embodiments of the invention in which host cells are cultured under conditions for a particular desired use, host cells are selected that have desired characteristics under the condition for the desired use.

A further advantageous property of the host cells and cell lines described herein is that the cells or cell lines comprising the reporter nucleic acid constructs can be selected and/or established in the absence of drug or other selective pressure. Thus, in preferred embodiments, the host cells and cell lines described herein are maintained in culture without any selective pressure. In further embodiments, host cells and cell lines described herein are maintained without any drugs or antibiotics.

Drug-free and selective pressure-free cell maintenance of the host cells and cell lines described herein provides a number of advantages. For example, selective drugs and other selective pressure factors can be mutagenic or otherwise can interfere with the physiology of the cells, leading to skewed results in cell-based assays. For example, selective drugs may decrease susceptibility to apoptosis (Robinson et al., *Biochemistry*, 36(37):11169-11178 (1997)), increase DNA repair and drug metabolism (Deffie et al., *Cancer Res.* 48(13): 3595-3602 (1988)), increase cellular pH (Thiebaut et al., *J Histochem Cytochem.* 38(5):685-690 (1990); Roepe et al., *Biochemistry*, 32(41):11042-11056 (1993); Simon et al., *Proc Natl Acad. Sci. USA*. 91(3):1128-1132 (1994)), decrease lysosomal and endosomal pH (Schindler et al., *Biochemistry* 35(9):2811-2817 (1996); Altan et al., *J. Exp. Med.* 187(10): 1583-1598 (1998)), decrease plasma membrane potential (Roepe et al., *Biochemistry*, 32(41): 11042-11056 (1993)), increase plasma membrane conductance to chloride (Gill et al., *Cell* 71(1):23-32 (1992)) and ATP (Abraham et al., *Proc. Natl. Acad. Sci. USA*, 90(1):312-316 (1993)), and increase rates of vesicle transport (Altan et al., *Proc. Natl. Acad. Sci. USA*, 96(8):4432-4437 (1999)). Thus, in certain embodiments, host cells and cell lines described herein allow screening assays that are free from the artifacts caused by selective pressure. In some embodiments, host cells and cell lines described herein are not cultured with selective pressure factors, such as antibiotics, before or after cell sorting, so that host cells and cell lines with desired properties are isolated by sorting, even when not beginning with an enriched cell population. In specific embodiments, host cells or cell lines are purified or isolated.

Isolated host cells and cell lines may be further characterized, such as by PCR, RT-PCR, qRT-PCR and single endpoint RT-PCR to determine the absolute amounts and relative amounts (in the case of multiple CTR factors) being expressed (RNA).

4.2.4. Fluorogenic Oliogonucleotides

Any fluorogenic oligonucleotides useful in the methods described herein can be used. Fluorogenic oligonucleotides can be useful for selection of host cells with the desired features (e.g., host cells comprising one or more reporter nucleic acid constructs). Fluorogenic oligonucleotides can be oligonucleotides comprising a sequence complementary to a target sequence (e.g., a sequence of the coding region RNA transcript, a sequence in the 5' or 3' UTR of an RNA transcript) and a signal emitting system so arranged that a fluorescent signal is quenched in the absence of target sequence, and the fluorescent signal is no longer quenched or quenched to a less degree in the presence of target sequence. By way of a non-limiting illustration, a fluorogenic oligonucleotide may comprise a fluorophore and a quencher positioned in the fluorogenic oligonucleotide so that the quencher and fluorophore are brought together in the absence of target sequence. For example, the fluorophore may be positioned at the terminus of an oligonucleotide and the quencher may be positioned at the other terminus of the oligonucleotide, wherein the oligonucleotide adopts one conformation or secondary structure, such as a stem-loop or hairpin loop, when not bound or hybridized to a target sequence, and adopts a different conformation or secondary structure when bound or hybridized to a target sequence. For example, upon binding between the fluorogenic nucleotide and the target sequence, the quencher and fluorophore separate, resulting in dequenching of the fluorescent signal. International PCT Patent Application Publication WO 2005/079462, for example, describes a number of signaling probes that may be, and are preferably, used in the production of the cells and cell lines described. The distance required for currently known fluorophore and quencher to interact is about 20-100 A. In specific embodiments, the distance between a fluorophore and a quencher of a fluorogenic oligonucleotide is about 10, 15, 20, 30, 40, 50, 60, 70, 80, 90, 100, 110, 105, 110, 115, or 120 A, or any value in between.

A fluorogenic oligonucleotide can comprise more than one interacting pair of fluorophore and quencher. For example, a wavelength-shifting fluorogenic oligonucleotide has a first fluorophore and a second fluorophore that both interact with the quencher, and the two fluorophores are FRET donor and acceptor pairs. The moieties of the interacting pair of fluorophore and quencher may be attached to the termini of the fluorogenic oligonucleotide or may be attached within the nucleic acid sequence. Examples of moieties that may be incorporated internally into the sequence of the fluorogenic oligonucleotide include the quenchers: dabcyl dT, BHQ2 dT, and BHQ1 dT, and the fluorophores: fluorescein dT, Alexa dT, and Tamra dT. Multiple quenchers can be used to decrease or eliminate signal in the absence of target sequence. Examples of quenchers include but are not limited to DABCYL, EDAC, Cesium, p-xylene-bis-pyridinium bromide, Thallium and Gold nanoparticles.

Fluorogenic oligonucleotides may be DNA or RNA oligonucleotides. Fluorogenic oligonucleotides may be chemically synthesized using techniques known in the art. Chemical modifications of fluorogenic oligonucleotides have been described in the art, e.g., see U.S. Pat. No. 6,692,965 and International PCT Patent Application Publication No. WO 2005/079462. Both of these documents are incorporated herein by reference in their entirety.

A target sequence and fluorogenic oligonucleotide may be designed to be fully complementary or comprise complementary regions and non-complementary regions. In one embodiment, the two separate target sequence and probe are designed to be fully complementary to each other. In one embodiment, a target sequence and fluorogenic oligonucleotide form a mutually complementary region of 4 to 9, 5 to 6, 2 to 10, 10 to 40, or 40 to 400 continuous bps at each end. A target sequence and fluorogenic oligonucleotide may each contain 5-7, 8-10, 11-15, 16-22, more than 30, 3-10, 11-80, 81-200, or more than 200 nucleotides or modified nucleotides. target sequence and fluorogenic oligonucleotide may have the same or a different number of nucleotides. In one embodiment, the 5' end of one strand (e.g., target sequence and fluorogenic oligonucleotide) is offset from the other strand, or the 3' end of that strand is offset from the other strand, or both, wherein the offset is up to 5, up to 10, up to 20, or up to 30 nucleotides or modified nucleotides.

The region that hybridizes to the target sequence may be in the complementary regions, non-complementary regions of one or both strands or a combination thereof. More than one target nucleic acid sequence may be targeted by the same fluorogenic oligonucleotide. The one or more target sequences may be on the same or different sequences, and they may be exactly complementary to the portion of the probe designed to bind target or at least complementary enough. In one embodiment, the two strands form a mutually complementary region at each end and the target complement sequence resides in the regions other than the mutually complementary regions at the ends.

In a specific embodiment, a target sequence or fluorogenic oligonucleotide is about 5 to 1,000 nucleotides, about 5 to 750 nucleotides, about 5 to 500 nucleotides, about 5 to 250 nucleotides, about 5 to 200 nucleotides, about 5 to 150 nucleotides, about 5 to 100 nucleotides, about 5 to 100 nucleotides, about 5 to 75 nucleotides, about 5 to 500 nucleotides, about 10 to 100 nucleotides, about 10 to 75 nucleotides, about 10 to 50 nucleotides, about 20 to 100 nucleotides, about 20 to 75 nucleotides, or about 30 to 100 nucleotides, in length, or any length in between. In a specific embodiment, a target sequence or fluorogenic oligonucleotide is about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In certain embodiments, a fluorogenic oligonucleotide is at most 10 nucleotides, 15 nucleotides, 20 nucleotides, 25 nucleotides, 30 nucleotides, 35 nucleotides, 40 nucleotides, 45 nucleotides, 50 nucleotides, 55 nucleotides, 60 nucleotides, 65 nucleotides, 70 nucleotides, 75 nucleotides, 80 nucleotides, 85 nucleotides, 90 nucleotides, 95 nucleotides, or 100 nucleotides in length. In a specific embodiment, a fluorogenic oligonucleotide is less than 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length.

In one embodiment, the fluorogenic oligonucleotide with at least two separate strands is a fluorogenic oligonucleotide. In one embodiment, one strand has at least a quencher moiety on one terminus, and a fluorophore on an adjacent terminus of the other strand. In one embodiment, each of the 5' and 3' terminus of one strand has the same or a different fluorophore, and each of the 5' and 3' terminus of the other strand has the same or a different quencher moiety. In one embodiment, the 5' terminus of one strand has a fluorophore and the 3' terminus has a quencher moiety, and the 3' terminus of the other strand has the same or a different quencher moiety and the 5' terminus has the same or a different fluorophore.

Where target sequences are used, each vector (where multiple vectors are used) can comprise the same or a different target sequence. Whether the target sequences are the same or different, the fluorogenic oligonucleotides may comprise different signal emitters, such as different colored fluorophores and the like so that expression of each subunit may be separately detected. By way of illustration, the fluorogenic nucleotide that specifically detects a first mRNA of interest can comprise a red fluorophore, the probe that detects a second mRNA of interest can comprise a green fluorophore, and the probe that detects a third mRNA of interest can comprise a blue fluorophore. Those of skill in the art will be aware of other means for differentially detecting the expression of the three subunits with a fluorogenic oligonucleotide in a triply transfected cell.

In one embodiment, the fluorogenic oligonucleotides are designed to be complementary to either a portion of the RNA encoding the protein of interest, e.g., the reporter, or to portions of the 5' or 3' UTRs. Even if the fluorogenic oligonucleotide designed to recognize a messenger RNA of interest is able to detect spuriously endogenously expressed target sequences, the proportion of these in comparison to the proportion of the sequence of interest produced by transfected cells is such that the sorter is able to discriminate the two cell types.

The activity or expression level of a protein of interest (e.g., reporter or CTR factor) may vary from cell to cell or cell line to cell line. The activity or expression level in a cell or cell line may also increase or decrease over time due to epigenetic events such as DNA methylation and gene silencing and loss of transgene copies. These variations can be attributed to a variety of factors, for example, the copy number of the transgene taken up by the cell, the site of genomic integration of the transgene, and the integrity of the transgene following genomic integration. One may use FACS or other cell sorting methods (i.e., MACS) to evaluate expression levels. Additional rounds of introducing signaling probes may be used, for example, to determine if and to what extent the cells remain positive over time for anyone or more of the RNAs for which they were originally isolated.

As will be appreciated by those of skill in the art, any reagent that is suitable for use with a chosen host cell may be used to introduce a nucleic acid, e.g. plasmid, oligonucleotide, labeled oligonucleotide, into a host cell with proper optimization. Examples of reagents that may be used to introduce nucleic acids, such as fluorogenic oligonucleotides, into host cells include but are not limited to: LIPOFECTAMINE™ transfection reagent, LIPOFECTAMINE™ 2000 transfection reagent, OLIGOFECTAMINE™ transfection reagent, TFX™ transfection reagents, FUGENE® 6 transfection reagent, DOTAP/DOPE, METAFECTENE® transfection reagent, or Fecturi. Cells are harvested and transfected with fluorogenic oligonucleotides.

4.3 Compounds

The methods described herein allow for identification and validation of compounds as modulators of cell fate/cell-type specification. Any compound may be used in the methods described herein. In certain aspects, the methods described herein allow for screening of compound libraries in high throughput assays.

As used herein, a compound may refer to any agent that is being tested for its ability to modulate cell fate, such as maintenance, cell specification, cell determination, induction of stem cell fate, cell differentiation, dedifferentiation, and/or trans-differentiation. In other aspects, a compound may refer to any agent that is being tested for its ability to modulate transcription, e.g., to modulate activity of a promoter, such as a CTR promoter. Compounds include, but are not limited to, proteinaceous molecules, including, but not limited to, peptides (including dimers and multimers of such peptides), polypeptides, proteins, including post-translationally modified proteins, conjugates, antibodies, antibody fragments etc.; small molecules, including inorganic or organic compounds; nucleic acid molecules (e.g., DNA or RNA) or polynucleotides including, but not limited to, double-stranded or single-stranded DNA, or double-stranded or single-stranded RNA, antisense RNA, RNAi molecules (e.g., siRNA, miRNA, short hairpin RNA (shRNA), etc.), intron sequences, triple helix nucleic acid molecules and aptamers; carbohydrates; and lipids. In specific embodiments, compounds may be hybrids or derivatives. In one embodiment, a Compound is purified.

In specific embodiments, compounds may be obtained or purified from natural sources, such as natural extracts. In some embodiments, compounds are synthesized. In specific embodiments, a purified compound is 60%, 65%, 70%, 75%, 80%, 85%, 90%, 95% or 99% free of other, different compounds or agents.

Any suitable library of compounds may be used in the methods described herein to screen for modulators of cell fate/cell-type specification. Non-limiting examples of small molecule libraries include LOPAC, TimTec, ChemDiv, Asinex and Ryan Scientific. Some compounds can be purchased through commercial sources, for example, Chembridge's Hit2Lead Chemical Store (San Diego, Calif.). Other compound libraries, such as siRNAs and miRNAs libraries, are also commercially available. In certain embodiments, compounds that are small molecules include solvates, hydrates, prodrugs, stereoisomers and/or pharmaceutically acceptable salts thereof.

In certain embodiments, compounds described herein are RNAs such as messenger RNAs that encode proteins (e.g., transcription factors, cytokines, receptors, intracellular signaling molecules); antisense RNA; small interfering RNA (siRNA); miRNAs; structural RNAs; cellular RNAs (e.g., ribosomal RNAs, tRNAs, hnRNA, and snRNA); random RNAs; RNAs corresponding to cDNAs or ESTs; RNAs that may be incorporated into various macromolecular complexes; RNAs that are ribozymes or catalytic RNAs; RNAs corresponding to viral or foreign RNAs, linker RNA, or sequence that links one or more RNAs; or RNAs that do not have the aforementioned function or activity but which may be expressed by cells nevertheless. In certain embodiments, a library of compounds that are RNAs may be used in the methods described herein. In specific embodiments, compounds are DNA encoding such RNAs. In some embodiments, compounds include siRNAs or miRNAs that can inhibit or reduce expression of a protein, such as a CTR factor.

In particular embodiments, compounds for use in the methods described herein are HDAC inhibitors, kinase inhibitors (e.g., tyrosine kinase inhibitors), retinoids (e.g., all-trans retinoid acid), hormones, antibodies, soluble receptors, or receptor ligands.

In specific embodiments, compounds described herein that are polypeptides can be soluble (e.g., secreted), cell membrane bound, or intracellular polypeptides. In certain aspects, compounds for use in the methods described herein are transcription factors or CTR factors.

In specific embodiments, compounds described herein are used to screen an expression library. For example, an expression library of different cell types engineered to comprise one or more reporter constructs described herein, are contacted with, exposed to, or introduced to, one or more compounds, and the activity or expression levels of a reporter are determined, as an indication of the CTR promoter activity in the cells, which may also serve as a marker of cell fate. In certain embodiments, cells that have expression or activity of a reporter over background are selected from the expression library. In other embodiments, cells with low or no expression or activity of a reporter over background are selected from the expression library.

In particular aspects, compounds for use in the methods described herein are nucleic acid constructs (e.g., DNA or RNA) that encode one or more transcription factors or CTR factors described herein (e.g., in section 4.2.1). For example, in some embodiments relating to modulation of eye specific promoters, Lhx2 and Pax6, or DNA or RNA encoding Lhx2 and Pax6, are compounds that can modulate activity of the promoter of Six6 (NP_031400). In some embodiments relating to modulation of skin stem cells (bulge cells), NFATc1, or DNA or RNA encoding the same, is a compound that represses the CDK4 promoter (NM_000075), and Sox9, or DNA or RNA encoding the same, is a compound that can activate the MITF promoter. In particular embodiments relating to modulation of skin stem cells (bulge cells), TCF3, or DNA or RNA encoding the same, is a compound that activates the CDKN1A promoter (NP_000380). In other embodiments, Sox2 and Oct4, or DNA or RNA encoding the same, are compounds that can activate the Nanog promoter. In specific embodiments, compounds for use in the methods described herein are nucleic acid constructs (e.g., DNA or RNA) encoding such transcription factors. In some embodiments, compounds for use in the methods described herein are polypeptides of such transcription factors, or polypeptide fragments thereof.

In particular embodiments, compounds for use in the methods described herein are cytokines or growth factors, or DNA or RNA encoding the same. In various embodiments, the cytokine is selected from the group consisting of LIF (leukemia inhibitory factor), SCF (stem cell factor), c-Kit, flt-3/flk-2 Ligand, IL-1α, IL-1β, IL-2, IL-3, IL-4, IL-5, IL-6, IL-7, IL-8, IL-9, IL-10, IL-11, IL-12, IFNα, IFNβ3, IFNγ, TNFα, TNFβ, G-CSF, GM-CSF, TGF-β, IL-15, IL-18, GM-CSF, INF-γ, INF-α, SLC, endothelial monocyte activating protein-2 (EMAP2), MIP-3α, MIP-3β, or an MHC gene, such as HLA-B7. Additionally, other exemplary cytokines include other members of the TNF family, including but not limited to TNF-α-related apoptosis-inducing ligand (TRAIL), TNF-α-related activation-induced cytokine (TRANCE), TNF-α-related weak inducer of apoptosis (TWEAK), CD40 ligand (CD40L), LT-α, LT-β, OX4OL, CD4OL, FasL, CD27L, CD30L, 4-1BBL, APRIL, LIGHT, TL1, TNFSF16, TNFSF17, and AITR-L, or a functional portion thereof. See, e.g., Kwon et al., 1999, *Curr. Opin. Immunol.* 11:340-345 for a general review of the TNF family).

In specific embodiments, compounds for use in the methods described herein are antibodies or antigen-binding fragments thereof. As used herein, the terms "antibody" and "antibodies" (immunoglobulins) refer to monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, F(ab')$_2$ fragments, antibody fragments that exhibit the desired biological activity, disulfide-linked Fvs (sdFv), and anti-idiotypic (anti-Id) antibodies (including, e.g., anti-Id antibodies to antibodies of the invention), intrabodies, and epitope-binding fragments of any of the above. Antibodies may belong to one of the following classes: IgA, IgG, IgM, IgE, and IgD. In particular embodiments, compounds for use herein are anti-Notch antibodies, or fragments thereof.

Compounds identified and/or validated using the methods described herein can be positive modulators or a negative modulators of cell fate/cell-type specification. Modulators may be involved in transcriptional regulation. Modulator may induce or enhance transcription of a cell-type specific gene. In another embodiment, the modulator may inhibit or decrease transcription of a cell-type specific gene. In specific embodiments, modulators increase the activity of a CTR promoter of a reporter nucleic acid construct in host cells described herein.

In specific aspects, the modulator induces differentiated cells to acquire characteristics of pluripotent stem cells or multipotent stem cells. In some embodiments, the modulator modulates stem cell maintenance and/or proliferation. In other embodiments, the modulator induces cell differentiation. In certain embodiments, the modulator induces cell transdifferentiation. In particular embodiments, the modulator induces cell dedifferentiation.

Compounds known in the art to be modulators of cell fate/cell type specification may be used as positive and negative controls in the methods described herein. For example, retinoic acid may be used as an inducer of differentiation of cells of the neural lineage.

4.4 Methods for Identifying Modulators

The invention provides for methods for identifying and validating modulators of cell fate and methods for identifying and validating modulators of CTR promoter activity. In a certain aspect, the invention relates to methods for identifying and validating modulators of stem cell maintenance (e.g., self-renewal, growth and/or proliferation), cell specification, cell determination, induction of stem cell fate, or cell differentiation, dedifferentiation, or trans-differentiation. Methods for identifying and validating modulators of induced pluripotent stem cells, methods for identifying and validating modulators of cancer stem cells, and methods for identifying a positive modulator of myocyte differentiation are also provided. In particular embodiments, the methods described herein are for screening a library of compounds in a high throughput platform. In some embodiments, the methods described herein are for screening an expression library.

In other aspects, the invention relates to a method for identifying and/or validating a modulator of CTR promoter activity, comprising the steps of: (a) contacting, exposing, or introducing a host cell containing a reporter nucleic acid construct described herein with a compound; and (b) determining the activity or expression level of the reporter; wherein the compound is a modulator of CTR promoter activity, if the activity or expression level of the reporter is increased or decreased in the presence of the compound relative to the activity or expression level of the report in the absence of the compound. In specific embodiments of such methods, the step of determining the activity or expression level of the reporter (i.e., step (b)) is carried out approximately between 12 hours and 96 hours, or between 1 day and 35 days after step (a). In specific embodiments of such methods, the step of determining the activity or expression level of the reporter (i.e., step (b)) is carried out approximately 1 week, 2 weeks, 3 weeks, 4 weeks, or 5 weeks after step (a).

In certain aspects, the methods described herein are for identifying and validating modulators that can induce or increase the activity of a CTR promoter, such as a stem cell promoter. In other aspects, the methods described herein are for identifying and validating modulators that can inhibit or decrease the activity of a CTR promoter. Such methods involve contacting, exposing, or introducing host cells comprising one or more reporter nucleic acid constructs comprising an ORF encoding a reporter wherein the ORF is operably linked to a CTR promoter with a compound, and determining the activity or expression level of the reporter in the presence and absence of the compound as an indicator of the activity of the CTR promoter. The compound is a positive modulator if the activity or level of expression of the reporter is higher in the host cells in the presence of the compound than in the host cells in the absence of the compound. The compound is a negative modulator if the activity or level of expression of the reporter is lower in the host cells in the presence of the compound than in the host cells in the absence of the compound. In certain embodiments, a positive modulator of a CTR promoter is predicted to be an inducer of the cell type with which the CTR promoter or CTR gene is associated. In certain embodiments, a negative modulator of a CTR promoter is predicted to be a repressor or inhibitor of the cell type with which the CTR promoter or CTR gene is associated. In specific embodiments, the activity of the CTR promoter or the activity or expression level of a reporter serves as a cell-type marker.

In other aspects, the invention relates to a method for identifying and/or validating a modulator of cell fate comprising the steps of: (a) contacting, exposing, or introducing a host cell containing a reporter nucleic acid construct described herein with a compound; and (b) determining the activity or expression level of the reporter; wherein the compound is a modulator of cell fate if the activity or expression level of the reporter is increased or decreased in the presence of the compound relative to the activity or expression level of the reporter in the absence of the compound. In specific embodiments, the host cell is a stem cell, and the CTR promoter is a stem cell promoter or a differentiation marker promoter. In certain embodiments, the host cell is a differentiated cell, and the CTR promoter is a stem cell promoter or a differentiation marker promoter. In particular embodiments, the host cell is a cell of a first cell type, and the CTR promoter is a cell-type marker promoter of the first cell type or a cell-type marker promoter of a second cell type. In specific embodiments of such methods, the step of determining the activity or expression level of the reporter (i.e., step (b)) is carried out approximately between 12 hours and 72 hours, or between 1 day and 35 days after step (a). In specific embodiments of such methods, the step of determining the activity or expression level of the reporter (i.e., step (b)) is carried out approximately 1 week, 2 weeks, 3 weeks, 4 weeks, or 5 weeks after step (a).

In certain aspects, the invention relates to a method for identifying a positive modulator of cell fate comprising the steps of: (a) contacting (or exposing or introducing) a host cell containing a reporter nucleic acid construct described herein with a compound; and (b) determining the activity or expression level of the reporter; wherein the compound is a positive modulator of cell fate if the activity or expression level of the reporter is increased in the presence of the compound relative to the activity or expression level of the reporter in the absence of the compound.

In other aspects, the invention relates to a method for identifying and/or validating a modulator of stem cell maintenance, or of cell differentiation, dedifferentiation or transdifferentiation, comprising the steps of: (a) contact (or exposing or introducing) a host cell containing a reporter nucleic acid construct described herein with a compound; and (b) determining the activity or expression level of the reporter; wherein the compound is a modulator of stem cell maintenance, or of cell differentiation, dedifferentiation or transdifferentiation, respectively, if the activity or expression level of the reporter is increased or decreased in the presence of the compound relative to the activity or expression level of the reporter in the absence of the compound.

In certain aspects, the invention relates to a method for identifying a modulator of iPS cells comprising the steps of: (a) contacting (or exposing or introducing) a host cell containing a reporter nucleic acid construct described herein with a compound; and (b) determining the activity or expression level of the reporter; wherein the compound is a modulator of iPS cells if the activity or expression level of the reporter is increased in the presence of the compound relative to the activity or expression level of the reporter in the absence of the compound. In specific embodiments, a compound that is a modulator of iPS cells is capable of inducing or reprogramming a somatic cell, such as a fibroblast cell, to become an iPS cell. In some embodiments, a combination of compounds are modulators of iPS cells and are capable of inducing or reprogramming a somatic cell, such as a fibroblast cell, to become an iPS cell. In specific embodiments, a compound that is a modulator of iPS cells is capable of inducing or reprogramming a iPS cell to become a more differentiated cell or cell type. In some embodiments, a combination of compounds are modulators of iPS cells and are capable of inducing or reprogramming a iPS cell to become a more differentiated cell or cell type. In specific embodiments, a compound that is a modulator of iPS cells is capable of inducing or reprogramming an iPS cell to become a progenitor cell or a differentiated cell or cell type. In some embodiments, a combination of compounds are modulators of iPS cells and are capable of inducing or reprogramming an iPS cell to become a more differentiated cell (e.g., progenitor cell or differentiated/specialized cell) or cell type. In specific embodiments, a compound that is a modulator of iPS cells is involved in inducing or reprogramming an iPS cell to generate a whole non-human organism. In some embodiments, a combination of compounds are modulators of iPS cells and are involved in inducing or reprogramming an iPS cell to generate a whole non-human organism. Any engineered cells may be used to generate iPS cells. In specific embodiments of such methods, the step of determining the activity or expression level of the reporter (i.e., step (b)) is carried out approximately between 12 hours and 72 hours, or between 1 day and 35 days after step (a). In specific embodiments of such methods, the step of determining the activity or expression level of the reporter (i.e., step (b)) is carried out approximately 1 week, 2 weeks, 3 weeks, 4 weeks, or 5 weeks after step (a).

In specific embodiments, the invention relates to methods for generating new tissue, a new organ, or a whole non-human organism from iPS cells described herein. The invention also relates to methods for identifying compounds that can modulate or are involved in generating new tissue, a new organ, or a whole non-human organism or non-human animals from iPS cells described herein. Methods for generating new tissue, a new organ, or a whole non-human organism from iPS cells described herein may comprise (i) obtaining iPS cells; (ii) exposing iPS cells to conditions suitable for generating new tissue, a new organ, or a whole non-human organism. Methods for identifying compounds that modulate or are involved in generating new tissue, a new organ, or a whole non-human organism from iPS cells described herein may comprise (i) exposing iPS cells to conditions suitable for generating new tissue, a new organ, or a whole non-human organism or non-human animal in the presence or absence of a compound; and (ii) determining whether the iPS cells can generate a new tissue, a new organ, or a whole non-human organism. In certain embodiments a whole non-human organism or animal generated from iPS cells may be, but are not limited to, a mouse, rat, monkey, dog, cat, pig, sheep, goat, horse, chicken, donkey, frog, worm, insect (e.g., fly), or cow. In other embodiments, new tissue or organ generated from iPS cells may be, but are not limited to, new tissue or organ of a human mouse, rat, monkey, dog, cat, pig, sheep, goat, horse, chicken, donkey, frog, worm, insect (e.g., fly), or cow. In certain embodiments, the organ may be but is not limited to breast, colon, stomach, heart, brain, spinal cord, lung, liver, pancreas, kidney, eye, bladder, or skin. In certain embodiments, the new tissue may be but is not limited to tissue of the breast, colon, stomach, heart, brain, spinal cord, lung, liver, pancreas, kidney, eye, bladder, or skin.

In particular embodiments, host cells are engineered to express one or more CTR factors, which may provide the cellular context in the host cells for stem cell maintenance (e.g., self-renewal, growth and/or proliferation), cell specification, cell determination, induction of stem cell fate, cell differentiation, cell dedifferentiation, or cell transdifferentiation. In other embodiments, host cells are engineered to express one or more CTR factors, which may provide the cellular context in the host cells for inducing pluripotent stem cells.

The invention also provides for methods of screening for compounds and CTR factors and combinations of CTR factors for use in the methods described herein. For example, such methods comprise the steps of introducing to host cells a plurality of different combinations of one or more compounds or CTR factors, and determining the presence of one or more desired properties or cellular context, e.g., expression of cell-type specific markers, CTR promoter activity, enzymatic activity, gene expression profile, and/or morphology. In specific embodiments, introduction of one compound or CTR factor, or a combination of two, three, or four compounds or CTR factors to the host cells achieves the desired properties or cellular context. In specific embodiments, the methods provide for screening compounds or CTR factors that are polynucleotides such as DNA or RNA (e.g., mRNA, siRNA, or miRNA). In particular embodiments, one or more test RNAs may be introduced to the host cells to test the RNAs' effects on the activity of the CTR promoter of the reporter nucleic acid construct, or to test the RNAs' effects on cell fate/cell-type specification. In certain embodiments, the test RNAs are encoded by a reporter nucleic acid construct described herein. In other embodiments, the methods provide for screening compounds or CTR factors that are polypeptides, small molecules, or antibodies. In certain embodiments, the methods provide for screening a library of compounds or CTR factors that may be any combination of agents or compounds described herein. In particular aspects, the methods provide for high throughput screening. In specific embodiments, the methods provide for screening live cells in real time.

In specific aspects, the invention provides for an expression library, wherein a panal of different cells are engineered to comprise one or more of the reporter nucleic acid constructs described herein. For example, an expression library of different cell types engineered to comprise one or more reporter constructs described herein, are contacted with (or exposed to or introduced to) one or more compounds, and the activity or expression levels of a reporter are determined, as a correlation with the CTR promoter activity in the cells or the cellular context of the cells. Such expression library may be useful for identifying or selecting host cells wherein a CTR promoter is active or inactive relative to background levels. In particular embodiments, an expression library comprises more than 100 different cell types which comprise one or more reporter nucleic acid constructs described herein. In certain embodiments, an expression library comprises at least 5, 10, 15, 20, 50, 75, 125, 150, 175, 200, 300, 400, 500, 600, 700, 800, 900, or 1,000 different cell types which comprise one or more reporter nucleic acid constructs described herein. In certain embodiments, host cells in the expression library contain or recombinantly express one or more CTR factors.

Maintenance of Pluripotency

In particular aspects, the methods described herein are for identifying and validating modulators that are capable of maintaining stem cell pluripotency. In such methods, host cells comprising a reporter nucleic acid construct comprising an ORF encoding a reporter wherein the ORF is operably linked to a CTR promoter, are contacted with (or exposed to or introduced to) a compound, and the activity or expression level of the reporter in the presence and absence of the compound is determined. The CTR promoter may be a promoter of a gene that is a stem cell marker (e.g., a gene that is predominantly, or in some cases exclusively, expressed in stem cells and not in other cell types, or that is expressed at higher levels in stem cells than in other cells). The host cell may be a stem cell (e.g., ESC, HSC, neural stem cell, muscle stem cell, etc.). The expression level of the reporter is an indicator of the activity of the CTR promoter, which serves as an indicator of the cellular context. For example, if the CTR promoter is a promoter of a stem cell marker gene, then the CTR promoter would be active (above background) in stem cells, and the activity of the CTR promoter would decrease or become inactive in cells that have lost there stem cell phenotypes and/or have become more differentiated. ESC and iPS cells can be maintained in the pluripotent state by the addition of defined growth factors and/or by co-culturing the cells with irradiated fibroblasts (see, e.g., Amit et al., *Semin. Reprod. Med.*, 2006, 24(5):298-303). Adult stem cell populations are more difficult to maintain in vitro. For example, expansion of HSCs in vitro is difficult. Other adult stem cells can be maintained in vitro, such as neural stem cells.

In some embodiments relating to stem cell maintenance, host cells are stem cells (e.g., ESCs) comprising a reporter nucleic acid construct described herein, and the CTR promoter of the nucleic acid construct comprises a region of the promoter of Oct4, Sox2, Klf4, c-myc, LIN28, Nanog, SSEA-3, or SSEA-4, wherein the region is a functional regulatory region of transcription.

Differentiation

The process of differentiation, or the production of mature progeny from a stem cell, usually requires the presence of defined growth factors. Differentiation proceeds through multiple steps usually with differential requirements for different stages. This process mimics the environment a cell would see in vivo as it matures. One challenge in the field of regenerative medicine is the discovery of conditions that can support the production of a defined cell type from an ESC or iPS cell. Another challenge is discovery of conditions that can regulate gene expression that results in the production of a defined cell type from an ESC or iPS cell.

In some aspects, the methods described herein are for identifying and validating modulators that are capable of inducing or inhibiting cell differentiation. In such methods, host cells comprising a reporter nucleic acid construct comprising an ORF encoding a reporter, wherein the ORF is operably linked to a CTR promoter, are contacted with (or exposed to or introduced to) a compound, and the activity or expression level of the reporter in the presence and absence of the compound is determined. The CTR promoter may be a promoter of a gene that is a differentiation marker (e.g., a gene that is predominantly, or in some cases exclusively, expressed in a particular differentiated cell, such as skin cell and muscle cell, and not in other cell types, or that is expressed at a higher level in a particular differentiated cell type than in other cell types). The host cell may be a stem cell (e.g., ESC, HSC, neural stem cell, muscle stem cell, iPS cell, etc.). The activity or expression level of the reporter is an indicator of the activity of the CTR promoter, which serves as an indicator of the cellular context. For example, if the CTR promoter is a promoter of a differentiation marker gene, then the CTR promoter would be active (relative to background) in more differentiated cells, and the activity of the CTR promoter would decrease or become inactive in cells that do not have differentiated phenotypes and/or have become less differentiated. For example, where host cells are stem cells and the CTR promoter is a promoter of a differentiation marker, the basal expression level of the reporter is low or not detectable, and positive modulators of differentiation will be able to increase or induce activity or expression of the reporter relative to activity or expression, respectively, in the host cells in the absence of the positive modulators. In specific embodiments, methods described herein relate to differentiation of stem cell into a progenitor cell. In certain embodiments, methods described herein relate to differentiation of a stem cell or progenitor cell into a differentiated or specialized cell.

In some aspects, the invention relates to a method for identifying a modulator of myocyte differentiation comprising the steps of: (a) contacting (or introducing or exposing) a host cell comprising a reporter nucleic acid construct described herein with (or to) a compound; and (b) determining the activity or expression level of the reporter; wherein the compound is a modulator of myocyte differentiation if the activity or expression level of the reporter is increased or decreased in the presence of the compound relative to the activity or expression level, respectively, of the reporter in the absence of the compound.

In certain aspects, the invention relates to a method for identifying a positive modulator of myocyte differentiation comprising the steps of: (a) contacting (or introducing or exposing) a host cell comprising a reporter nucleic acid construct described herein with (or to) a compound; and (b) determining the activity or expression level of the reporter; wherein the compound is a positive modulator of myocyte differentiation if the activity or expression level of the reporter is increased in the presence of the compound relative to the activity or expression level, respectively, of the reporter in the absence of the compound. In specific embodiments, the host cell is a stem cell, and the CTR promoter is a myocyte promoter.

In some aspects, the invention relates to a method for identifying a modulator of retina cell, skin cell, or heart muscle cell differentiation comprising the steps of: (a) contacting (or introducing or exposing) a host cell comprising a reporter nucleic acid construct described herein with (or to) a compound; and (b) determining the activity or expression level of the reporter; wherein the compound is a modulator of retina cell, skin cell, or heart muscle cell differentiation if the activity or expression level of the reporter is increased or decreased in the presence of the compound relative to the activity or expression level, respectively, of the reporter in the absence of the compound.

In some aspects, the invention relates to a method for identifying a modulator of iPS cell differentiation comprising the steps of: (a) contacting (or introducing or exposing) a host cell comprising a reporter nucleic acid construct described herein with (or to) a compound; and (b) determining the activity or expression level of the reporter; wherein the compound is a modulator of iPS cell differentiation if the activity or expression level of the reporter is increased or decreased in the presence of the compound relative to the activity or expression level, respectively, of the reporter in the absence of the compound.

Dedifferentiation and Transdifferentiation

Under certain conditions, more mature cells, or differentiated cells, can be manipulated to revert to a less differentiated state; this process is termed "dedifferentiation". The production of iPS cell from mature fibroblast is one example of this phenomenon. Dedifferentation is also a hall mark of cancerous cells. While, trans-differentiation is the process by which a mature cell becomes committed to a different lineage. For example, a fibroblast cell may trans-differentiate into a neuron cell. There have been reports of bone marrow stem cells differentiating into mature non-blood derived cell types such as liver or neurons (see, e.g., Kuçi et al., *Curr. Stem Cell Res. Ther.*, 2009, 4(2):107-17).

In some aspects, the methods described herein are for identifying and validating modulators that are capable of or involved in inducing or inhibiting cell dedifferentiation. In such methods, host cells comprising a reporter nucleic acid construct comprising an ORF encoding a reporter wherein the ORF is operably linked to a CTR promoter are contacted with (or exposed to or introduced to) a compound, and the activity or expression level of the reporter in the presence and absence of the compound is determined. The CTR promoter may be a promoter of a gene that is a differentiation marker (e.g., a gene that is predominantly, or in some cases exclusively, expressed in a particular differentiated cell, such as skin cell and muscle cell, and not in other cell types, or that is expressed in higher amounts in a particular differentiated cell type than in other cell types), stem cell marker, or progenitor cell marker. The activity or expression level of the reporter is an indicator of the activity of the CTR promoter, which serves as an indicator of the cellular context or cell type marker. For example, if the CTR promoter is a promoter of a differentiation marker gene, then the CTR promoter would be active (relative to background) in more differentiated cells, and the activity of the CTR promoter would be less active or inactive in stem cells or progenitor cells. For example, where the host cells are differentiated cells and the CTR promoter is a promoter of a differentiation marker, the basal activity or expression level of the reporter is high, and positive modulators of dedifferentiation will be able to decrease or inhibit activity or expression of the reporter relative to the activity or expression, respectively, in the host cells in the absence of the positive modulators of dedifferentiation. Where the host cells are differentiated cells and the CTR promoter is a promoter of a stem cell marker, the basal activity or expression level of the reporter is low or non-detectable in such differentiated cells, and positive modulators of dedifferentiation will be able to increase or enhance activity or expression of the reporter relative to the activity or expression in the host cells in the absence of the positive modulators of dedifferentiation.

In particular embodiments relating to cell dedifferentiation, the host cells are differentiated cells comprising a reporter nucleic acid construct described herein, and the CTR promoter is a promoter of a stem cell or stem cell marker. In specific embodiments, methods described herein relate to dedifferentiation of a progenitor cell into a stem cell. In certain embodiments, methods described herein relate to dedifferentiation of a differentiated or specialized cell into a progenitor cell or stem cell.

In certain aspects, the methods described herein are for identifying and validating modulators that are capable of, or are involved in, inducing or inhibiting cell transdifferentiation. In such methods, host cells comprising a reporter nucleic acid construct comprising an ORF encoding a reporter wherein the ORF is operably linked to a CTR promoter are contacted with (exposed to or introduced to) a compound, and the activity or expression level of the reporter in the presence and absence of the compound is determined. The CTR promoter may be a promoter of a gene that is a differentiation marker of a specific cell type, e.g., skin cell, myocyte, fibroblast, or pancreatic Beta cells. The activity or expression level of the reporter is an indicator of the activity of the CTR promoter, which serves as an indicator of the cellular context or cell type. For example, if the CTR promoter is a promoter of a differentiation marker gene for skin cells, then the CTR promoter would be active in differentiated skin cells, and the activity of the CTR promoter would be less active or inactive in other types of cells such as pancreatic Beta cells or neurons. In this respect, where the host cells are differentiated skin cells and the CTR promoter is a promoter of a differentiation marker of neurons, the basal activity or expression level of the reporter is low in the host differentiated skin cells, and positive modulators of transdifferentiation into neurons will be able to increase or induce activity or expression of the reporter relative to expression in the host cells in the absence of the positive modulators of transdifferentiation.

In certain aspects relating to cell transdifferentiation from a first cell type to a second cell type, host cells are differentiated cells of a first cell type comprising a reporter nucleic acid construct described herein, and the CTR promoter of the reporter nucleic acid construct comprises a region of a promoter of a gene that is a differentiation marker of a specific second cell type, e.g., skin cell, myocyte, fibroblast, or pancreatic Beta cells. For example, where the host cells are differentiated skin cells and the CTR promoter is a promoter of a differentiation marker of neurons, the basal activity or expression level of the reporter is low in the host differentiated skin cells, and positive modulators of transdifferentiation into neurons will be able to increase or induce activity or expression of the reporter relative to activity or expression in the host cells in the absence of the positive modulators of transdifferentiation.

In other aspects, the invention relates to a method for identifying and/or validating a modulator of iPS cells, comprising the steps of: (a) contacting (or exposing or introducing) a host cell containing a reporter nucleic acid construct described herein with (or to) a compound; and (b) determining the activity or expression level of the reporter; wherein the compound is a modulator of iPS cells, if the activity or expression level of the reporter is increased or decreased in the presence of the compound relative to the activity or expression level of the reporter in the absence of the compound. In specific embodiments, a host cell is a fibroblast cell comprising a reporter nucleic acid construct described herein, e.g., reporter nucleic acid construct comprising (i) an ORF encoding a reporter, which ORF is operably linked to a CTR promoter, and (ii) a nucleic acid sequence encoding one or more target sequence, and the CTR promoter comprises a region of the promoter of Oct4, Sox2, Klf4, c-myc, LIN28, Nanog, SSEA-3, or SSEA-4. In specific embodiments of such methods, the host cell is a differentiated cell such as a fibroblast, and the CTR promoter is a stem cell promoter, such as the Nanog promoter or a portion thereof.

In other aspects, the invention relates to a method for identifying and/or validating a modulator of cancer stem cells, comprising the steps of: (a) contacting (or exposing or introducing) a host cell containing a reporter nucleic acid construct described herein with (or to) a compound; and (b) determining the activity or expression level of the reporter; wherein the compound is a modulator of cancer stem cells, if the activity or expression level of the reporter is increased or decreased in the presence of the compound relative to the activity or expression level of the report in the absence of the compound. In specific embodiments of such methods, the host cell is a cancer stem cell, and the CTR promoter is a differentiation marker promoter or a portion thereof. In specific embodiments, the host cell is a cancer stem cell and the CTR promoter is a cancer stem cell marker promoter or a portion thereof, e.g., a promoter of CD133, CD44, or CD29, or a portion thereof.

Non-limiting examples of CTR promoters, such as stem cell promoters, which may be used in the methods described herein are described in section 4.1.2. One of skill in the art would be able to select the appropriate CTR promoter for the desired activity and goal.

In specific embodiments, the host cells for use in the method described herein further recombinantly expresses one or more CTR factors. In some embodiments, the methods for identifying and/or validating a modulator of cell type described herein further comprise exposing or introducing the host cells to one or more CTR factors, which may provide suitable conditions for modulation of CTR promoter activity or cell fate.

A wide range of techniques are known in the art for screening compounds of libraries for modulators of CTR promoter activity or cell fate. Such techniques are generally adaptable for rapid screening of compound libraries employing a high throughput platform. The most widely used techniques for screening large gene libraries typically involve plating host cells on multiwell plates (e.g., 96-well plates or 384-well plates) and exposing them to different culture conditions and/or contacting them with test compounds from a library, and detecting a feature, such as activity or expression level of the reporter or activity of the CTR promoter. Similar high throughput screening assays may be performed to identify specific combinations of CTR factors or test RNAs that provide the desired cellular properties or context for the methods described herein.

One of skill in the art would be able to employ an appropriate assay depending on the reporter used. For example, when the reporter is Luciferase, a bioluminescence assay can be employed to detect the activity of Luciferase. Lysate are exposed to a bioluminescent substrate, such as luciferin, and luminescence is measured using a plate reader (Tecan). In luminescent reactions, light is produced by the oxidation of a luciferin. Such assays have been described in the art.

Expression level of the reporter may be determined by RT-PCR or real time RT-PCR, which enables both detection and quantification of reporter mRNA transcripts. Primers specific for the reporter may be used. The RNA sequences corresponding to the reporter may itself be detected (e.g., using fluorogenic oligonucleotides).

In embodiments where the reporter is a fluorescent protein such as GFP, YFP, or RFP, detection of activity or expression of the reporter may be carried out using microscopy. In addition, other in vitro and cell-based assays known in the art, or described herein, may be used in the methods described here.

4.4.1. Assays

Modulators identified and/or validated using the methods described herein can be further validated in functional assays, which are known in the art. For example, in vitro transcription assays, cell-based assays, as well as in vivo animal models may be used to confirm the biological activities of the modulators described herein.

In Vitro Assays

A non-limiting example of a cell-free transcription assay involves use of HeLa cell nuclei extracts. HeLa nuclear extracts can support accurate transcription initiation by RNA polymerase II and exhibit both basal and regulated patterns of RNA polymerase transcription. The nuclear extract is also a source for a variety of transcription factors, DNA-binding proteins and the enzymatic machinery involved in RNA processing. Protocols for the HeLa cell nuclear extract transcription assay have been described in the art, see, e.g., Dignam et al. (1983) *Nucl. Acids Res.*, 11, 1475-89. Kits for these assays are also commercially available, e.g., the HELASCRIBE® Nuclear Extract in vitro Transcription System (Promega). A positive control template (CMV immediate early promoter DNA) may be used. A nucleic acid construct comprising the ORF of a reporter operably linked to a CTR promoter may be assayed using the HeLa cell nuclear extract in vitro transcription assay, in the presence and absence of various modulators.

Cell-Based Assays

Any cell-based assays known in the art may be employed to confirm the biological activity of modulators identified using the methods described herein. The cell-based assays may be used to confirm the effect of a compound on biological functions such as transcription, stem cell maintenance, stem cell proliferation, differentiation assays.

A non-limiting example of a cell-based assay to confirm the effect of a compound on transcription involves introducing in cells a reporter nucleic acid construct comprising the ORF of luciferase operably linked to a CTR promoter, culturing the cells in the presence and absence of the compound, and determining the level of expression of luciferase using method well known in the art, such as bioluminescence assays.

A non-limiting example of a cell-based assay to confirm the effect of a compound on stem cell maintenance and/or proliferation involves culturing stem cells in the presence and absence of the compound, and determining the rate of proliferation of the stem cells as well as the percentage of the population of cell that has maintained stem cell markers, such as SSEA-3 and SSEA-4, by methods well known in the art, e.g., flow cytometry. Non-limiting examples of proliferation assays include BrdU-incorporation assay, trypan-blue exclusion assay, and carboxyfluorescein succinimidyl ester (CFSE) assay.

A non-limiting example of a cell-based assay to confirm the effect of a compound on cell differentiation involves culturing cells such as stem cells in the presence and absence of the compound, and determining the percentage of the population of cell that has maintained stem cell markers, such as SSEA-3 and SSEA-4, and the percentage of cells that have acquired cell markers of a more differentiated cell. The percentage of cells that have loss the stem cell markers may also be determined. For example, stem cells may be cultured in the presence and absence of retinoic acid for a period of time; and cells that are positive for nestin, a marker of differentiated neuronal cells, are indicative of differentiated cells.

A non-limiting example of a cell-based assay to confirm the effect of a compound on cell dedifferentiation involves culturing differentiated cells, such as fibroblasts, in the presence and absence of the compound, and determining the percentage of cell that has maintained markers specific for the differentiated cells, and the percentage of cells that have acquired cell markers of a stem cell. The percentage of cells that have loss the differentiation markers may also be determined.

A non-limiting example of a cell-based assay to confirm the effect of a compound on cell transdifferentiation involves culturing cells of a cell type in the presence and absence of the compound, and determining the percentage of cells that has lost expression of markers specific for the first cell type and that has acquired expression of one or more markers specific for the second cell type.

Moreover, cell morphology may also be determined as an indication of cell type physical characteristics. The shape, size, or granularity of a desired cell type may be observed. For example, differentiated neuronal cells have longer and more extensions than less differentiated neuronal cells. As another example, heart muscle cells can contract or pulse, and this activity can be observed.

The staining of a cell using stains that label, e.g., lipids, proteins (e.g. immunofluorescence), RNAs (e.g. FISH) or other markers of specific or desired cell types could be used. For some cell types the activity of the cells could be measured (e.g. antibody production, the secretion of proteins known to be secreted by the cell type, or the beating or contraction of muscle cell types).

Certain characteristics of stem cells may also be determined in cell-based assays. A non-limiting example of a stem cell assay includes a tetraploid complementation assay involving the creation of a four-cell blastocysts. These four cell blastocysts can only contribute to extraembryonic tissues such as placenta and thus fail to develop, but injected stem cells can develop into an organism if the stem cells are pluripotent. For example, somatic cells comprising one or more reporter nucleic acid constructs described herein may be used to screen for compounds that can reprogram the somatic cells into iPS cells, and such iPS cells may be used in the tetraploid complementation assay to determine the pluripotency of the reprogrammed cells.

Animal Models

Xenograft animal models may be useful for confirming the biological activities of the modulators/compounds described herein as modulators of cell fate/cell type specification. Grafting human cells into animal models such as mice have the advantage in that the human grafted cells can be distinguished from the host cells due to the presence of human-specific markers.

For example, to confirm the activity of a modulator in transdifferentiation, human cells of a specific lineage, such as fibroblasts, may be transplanted into an animal such as SCID mice. The human cells may be pre-treated with a compound described herein prior to transplantation, and the mice have been suffering from a disease or condition, such as spinal cord injury or heart muscle damage. Alternatively, after transplantation, the mice may be administered the compound described herein. Subsequently, the mice are observed for improvement in one or more symptoms associated with the disease or condition. Additionally, tissue samples from the mice can be assayed (e.g., by immunohistochemistry) for human-specific and cell-type specific markers to determine if the transplanted human cells have transdifferentiated from one cell type. For ease of detection, the transplanted human cells can also be engineered to express a detectable signal, e.g., a reporter, such as luciferase or GFP, so that the cells can be detected in vivo. In a further aspect, the cells can be engineered to contain a recombinant nucleic acid construct comprising an ORF of a reporter, such as luciferase or GFP, operably linked to a CTR promoter, and the engineered cells can be transplanted into an animal. The animal is administered a compound. In one aspect, the reporter is expressed in vivo when the cell type of the cell has changed (e.g., the CTR promoter is initially inactive so that the reporter is not expressed, and the CTR promoter becomes active and drives expression of the reporter after administration of the compound to the animal).

Animal models can also be used to test the activity of a modulator of cancer stem cells in treating cancer, reducing the number of cancer cells, reducing the size of a tumor, or preventing recurrence of cancer. The modulator of cancer stem cells may be effective in differentiating cancer stem cells. For instance certain cancers are resistant to certain therapeutics where this resistance could be due to the resistance of cancer stem cells to the treatment. These cancer stem cells could result in re-emergence of new cancer cells. A compound that is found to differentiate cancer stem cells could be tested for such an effect by injecting animals with cancer stem cells and treating the animal with (i) the treatments that do not normally result in eradication of the cancer from the animal, (ii) the compound alone, and or (iii) combination of (i) and (ii). The animal can then be treated with the compounds identified by the methods described herein to confirm if a compound eliminates cancer stem cells, for instance by causing them to differentiate.

These and other embodiments of the invention may be further illustrated in the following non-limiting Examples.

5. EXAMPLES

Transfection

HEK293T (ATCC CRL-11268) are transfected with a plasmid encoding a promoter derived from the 5' UTR of NANOG gene (GenBank: AC006517) driving the expression of luciferase followed by an untranslated sequence encoding a tag for detection by a signaling probe target sequence. This cassette is flanked by two additional untranslated target sequences under the control of the CMV and elongation factor 1-alpha (EF) promoters, respectively. A sequence encoding a drug resistance marker is also present. The nucleic acid is introduced into the host cells using Lipofectamine. Examples of other reagents that may be used to introduce nucleic acids into host cells include but are not limited to LIPOFECTAMINE™ transfection reagent, LIPOFECTAMINE™ 2000 transfection reagent, OLIGOFECTAMINE™ transfection reagent, TFX™ transfection reagents, FUGENE® 6 transfection reagent, DOTAP/DOPE, METAFECTENE® transfection reagent, or Fecturin.

Although drug selection is optional in the methods of this invention, we include one drug resistance marker per plasmid. The cells are selected in media containing the drug for 10-14 days.

Exposure of Cells to Fluorogenic Oligonucleotides

Fluorogenic oligonucleotides are introduced into the host cells using Lipofectamine. Examples of reagents that may be used to introduce nucleic acids, such as fluorogenic oligonucleotides, into host cells include but are not limited to: LIPOFECTAMINE™ transfection reagent, LIPOFECTAMINE™ 2000 transfection reagent, OLIGOFECTAMINE™ transfection reagent, TFX™ transfection reagents, FUGENE® 6 transfection reagent, DOTAP/DOPE, METAFECTENE® transfection reagent, or Fecturi. Cells are harvested and transfected with fluorogenic oligonucleotides. The cells are then dissociated and collected for analysis and are sorted using a flow cytometric cell sorter.

Isolation of Positive Cells

Standard analytical methods are used to gate cells fluorescing above background or at very low levels and to isolate cells falling within those defined gate directly into 96-well plates. Cell sorting is operated such that a single cell is deposited per well. After selection, the cells are expanded in media lacking drug.

Confirmation of Inducibility.

Resulting cells are transfected with plasmids encoding Oct4 and Sox2 using standard reagents. After 48, 72, or 96 hours, the cells are harvested, lysed and the supernatants collected. Lysate are exposed to a bioluminescent substrate and luminescence is measured using a plate reader (Tecan).

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed:

1. An in vitro method for making a recombinant cell comprising the steps of:
   (a) introducing into a cell a recombinant nucleic acid construct comprising:
      i) an open reading frame (ORF) encoding a reporter wherein the ORF is operably linked to a cell type related (CTR) promoter, and wherein the CTR promoter is not active above background levels in the cell; and
      ii) a nucleic acid sequence encoding a first target sequence RNA1 (TSR1), a nucleic acid sequence encoding a second target sequence RNA2 (TSR2), and a nucleic acid sequence encoding a third target sequence RNA3 (TSR3), wherein the TSR3 is cotranscribed with the reporter, and wherein the TSR1 and TSR2 flank the reporter ORF and the CTR promoter, and wherein the transcription of TSR1 and TSR2 are each driven by a constitutively active promoter that is different from the CTR promoter;
   (b) introducing into the cell fluorogenic oligonucleotides that are complementary to TSR1, TSR2, and TSR3; and
   (c) selecting cells that transcribe both TSR1 and TSR2, and do not transcribe TSR3 above background levels.

2. An in vitro method for identifying a positive or negative modulator of cell type comprising the steps of:
   (a) contacting the recombinant cell made by the method of claim 1 with a compound; and
   (b) determining the activity or expression level of the reporter;
   wherein the compound is a modulator of cell type if the activity or expression level of the reporter is increased in the presence of the compound relative to the activity or expression level, respectively, of the reporter in the absence of the compound.

3. The method of claim 2, wherein the CTR promoter is a stem cell promoter.

4. The method of claim 2 further comprising the step of introducing into the cell a CTR factor or a recombinant nucleic acid encoding a CTR factor.

5. The method of claim 3 further comprising the step of introducing into the cell a CTR factor or a recombinant nucleic acid encoding a CTR factor.

6. The method of claim 1, wherein the CTR promoter is a myocyte specific promoter.

7. The method of claim 6 further comprising the step of introducing into the cell a CTR factor or a recombinant nucleic acid encoding a CTR factor.

8. An in vitro method for identifying a positive or negative modulator of myocyte differentiation comprising the steps of:
   (a) contacting the recombinant cell made by the method of claim 1 with a compound, wherein the recombinant cell is a myocyte; and
   (b) determining the activity or expression level of the reporter;
   wherein the compound is a modulator of myocyte differentiation if the activity or expression level of the reporter is increased in the presence of the compound relative to the activity or expression level, respectively, of the reporter in the absence of the compound.

9. The method of claim 1, wherein the CTR promoter is a promoter of a marker gene selected from the group consisting of the genes listed in Table 1.

10. The method of claim 1, wherein a first promoter drives transcription of TSR1 and a second promoter drives transcription of TSR2.

11. The method of claim 10, wherein the second promoter that drives transcription of TSR2 is different from the first promoter that drives transcription of TSR1.

12. The method of claim 1, wherein TSR1 and TSR2 are in the same or in the opposite orientation relative to the orientation of the CTR promoter and reporter.

13. The method of claim 1, wherein TSR1 and TSR2 are driven by an RNA polymerase III promoter, an RNA polymerase II promoter, a heterologous promoter, cytomegalovirus (CMV) promoter, nuclear T7 promoter, SV40 early promoter region, a promoter contained in the 3' long terminal repeat of Rous sarcoma virus, a herpes thymidine kinase promoter, or regulatory sequences of the metallothionein gene.

14. The method of claim 1, wherein TSR3 is a marker for selection of cells wherein the CTR promoter is not active above background levels.

15. The method of claim 1, wherein the recombinant nucleic acid construct or the cell comprising the recombinant nucleic acid construct does not comprise a drug resistance gene.

16. The method of claim 1, wherein the cell is a eukaryotic cell.

17. The method of claim 1, wherein the cell is obtained from a mouse, rat, monkey, dog, cat, pig, sheep, goat, horse, chicken, frog, worm, insect, or a cow.

18. The method of claim 16, wherein the cell is a mammalian cell.

19. The method of claim 18, wherein the mammalian cell is a human cell.

* * * * *

SEQUENCE LISTING

```
<160> NUMBER OF SEQ ID NOS: 109

<210> SEQ ID NO 1
<211> LENGTH: 33
<212> TYPE: DNA
<213> ORGANISM: Artificial Sequence
<220> FEATURE:
<223> OTHER INFORMATION: consensus DNA binding element 1 of
      transcription factor p53
<220> FEATURE:
<221> NAME/KEY: misc_feature
<222> LOCATION: (11)...(23)
<223> OTHER INFORMATION: n = y or absent

<400> SEQUENCE: 1
rrrcwwgyyy nnnnnnnnnn nnnrrrcwwg yyy                                  33

<210> SEQ ID NO 2
<211> LENGTH: 20
<212> TYPE: DNA
<213> ORGANISM: Artificial Sequence
<220> FEATURE:
<223> OTHER INFORMATION: consensus DNA binding element 2 of
      transcription factor p53

<400> SEQUENCE: 2
ggacatgccc gggcatgtcc                                                 20

<210> SEQ ID NO 3
<211> LENGTH: 20
<212> TYPE: DNA
<213> ORGANISM: Artificial Sequence
```

```
<220> FEATURE:
<223> OTHER INFORMATION: an example of consensus DNA binding element of
      transcription factor ERE
<220> FEATURE:
<221> NAME/KEY: misc_feature
<222> LOCATION: (6)...(15)
<223> OTHER INFORMATION: n = A,T,C or G

<400> SEQUENCE: 3
ggtcannnnn nnnnntgacc                                               20

<210> SEQ ID NO 4
<211> LENGTH: 18
<212> TYPE: DNA
<213> ORGANISM: Artificial Sequence
<220> FEATURE:
<223> OTHER INFORMATION: an example of consensus DNA binding element of
      transcription factor Sox2-Oct4
<220> FEATURE:
<221> NAME/KEY: misc_feature
<222> LOCATION: 8
<223> OTHER INFORMATION: n = A,T,C or G
<220> FEATURE:
<221> NAME/KEY: misc_feature
<222> LOCATION: 9, 10
<223> OTHER INFORMATION: n = A,T,C, G or absent

<400> SEQUENCE: 4
cwttgtdnnn atgmwwry                                                 18

<210> SEQ ID NO 5
<211> LENGTH: 10
<212> TYPE: DNA
<213> ORGANISM: Artificial Sequence
<220> FEATURE:
<223> OTHER INFORMATION: consensus DNA binding element of transcription
      factor GR

<400> SEQUENCE: 5
agaacagatg                                                          10

<210> SEQ ID NO 6
<211> LENGTH: 13
<212> TYPE: DNA
<213> ORGANISM: Artificial Sequence
<220> FEATURE:
<223> OTHER INFORMATION: consensus DNA binding element of transcription
      factor NF-I

<400> SEQUENCE: 6
tgaatatggg cca                                                      13

<210> SEQ ID NO 7
<211> LENGTH: 20
<212> TYPE: DNA
<213> ORGANISM: Artificial Sequence
<220> FEATURE:
<223> OTHER INFORMATION: consensus DNA binding element of transcription
      factor SRF

<400> SEQUENCE: 7
aagatgcgga tattggcgat                                               20

<210> SEQ ID NO 8
<211> LENGTH: 17
<212> TYPE: DNA
<213> ORGANISM: Artificial Sequence
<220> FEATURE:
<223> OTHER INFORMATION: consensus DNA binding element of transcription
``` factor c-Fos

<400> SEQUENCE: 8
aacatgactc agaggaa					17

<210> SEQ ID NO 9
<211> LENGTH: 15
<212> TYPE: DNA
<213> ORGANISM: Artificial Sequence
<220> FEATURE:
<223> OTHER INFORMATION: consensus DNA binding element of transcription
      factor 60k-protein

<400> SEQUENCE: 9
attaaatttt aaatt					15

<210> SEQ ID NO 10
<211> LENGTH: 29
<212> TYPE: DNA
<213> ORGANISM: Artificial Sequence
<220> FEATURE:
<223> OTHER INFORMATION: an example of consensus DNA binding element of
      transcription factor ABF1
<220> FEATURE:
<221> NAME/KEY: misc_feature
<222> LOCATION: 4, 15
<223> OTHER INFORMATION: n = A,T,C or G
<220> FEATURE:
<221> NAME/KEY: misc_feature
<222> LOCATION: (5)...(13), (16)...(24)
<223> OTHER INFORMATION: n = A,T,C,G or absent

<400> SEQUENCE: 10
wdcnnnnnnn nnnynnnnnn nnnnacgad					29

<210> SEQ ID NO 11
<211> LENGTH: 21
<212> TYPE: DNA
<213> ORGANISM: Artificial Sequence
<220> FEATURE:
<223> OTHER INFORMATION: consensus DNA binding element of transcription
      factor ACE1

<400> SEQUENCE: 11 tttttttgctg gaacggttca g					21

<210> SEQ ID NO 12
<211> LENGTH: 12
<212> TYPE: DNA
<213> ORGANISM: Artificial Sequence
<220> FEATURE:
<223> OTHER INFORMATION: consensus DNA binding element of transcription
      factor ADR1

<400> SEQUENCE: 12
taagttggag aa					12

<210> SEQ ID NO 13
<211> LENGTH: 13
<212> TYPE: DNA
<213> ORGANISM: Artificial Sequence
<220> FEATURE:
<223> OTHER INFORMATION: consensus DNA binding element of transcription
      factor AP-1

<400> SEQUENCE: 13
actcagagga aaa					13

<210> SEQ ID NO 14
<211> LENGTH: 23
<212> TYPE: DNA
<213> ORGANISM: Artificial Sequence
<220> FEATURE:
<223> OTHER INFORMATION: consensus DNA binding element of transcription
      factor AP-2

<400> SEQUENCE: 14
aaagggccgg tgggcgggag att                                              23

<210> SEQ ID NO 15
<211> LENGTH: 12
<212> TYPE: DNA
<213> ORGANISM: Artificial Sequence
<220> FEATURE:
<223> OTHER INFORMATION: consensus DNA binding element of transcription
      factor AP-3

<400> SEQUENCE: 15
actttccaca cc                                                          12

<210> SEQ ID NO 16
<211> LENGTH: 10
<212> TYPE: DNA
<213> ORGANISM: Artificial Sequence
<220> FEATURE:
<223> OTHER INFORMATION: consensus DNA binding element of transcription
      factor AP-4

<400> SEQUENCE: 16 ycagctgygg                                                             10

<210> SEQ ID NO 17
<211> LENGTH: 10
<212> TYPE: DNA
<213> ORGANISM: Artificial Sequence
<220> FEATURE:
<223> OTHER INFORMATION: consensus DNA binding element of transcription
      factor AP-5

<400> SEQUENCE: 17
ctgtggaatg                                                             10

<210> SEQ ID NO 18
<211> LENGTH: 17
<212> TYPE: DNA
<213> ORGANISM: Artificial Sequence
<220> FEATURE:
<223> OTHER INFORMATION: consensus DNA binding element of transcription
      factor APF

<400> SEQUENCE: 18
aggttaataa ttttcca                                                     17

<210> SEQ ID NO 19
<211> LENGTH: 18
<212> TYPE: DNA
<213> ORGANISM: Artificial Sequence
<220> FEATURE:
<223> OTHER INFORMATION: consensus DNA binding element of transcription
      factor APF/HNF1

<400> SEQUENCE: 19
tggttaatga tctacagt                                                    18

```
<210> SEQ ID NO 20
<211> LENGTH: 18
<212> TYPE: DNA
<213> ORGANISM: Artificial Sequence
<220> FEATURE:
<223> OTHER INFORMATION: consensus DNA binding element of transcription
      factor ATF/CREB

<400> SEQUENCE: 20
aaattgacgt catggtaa                                                       18

<210> SEQ ID NO 21
<211> LENGTH: 22
<212> TYPE: DNA
<213> ORGANISM: Artificial Sequence
<220> FEATURE:
<223> OTHER INFORMATION: consensus DNA binding element of transcription
      factor Adf-1

<400> SEQUENCE: 21
gagatcgcgt aacggtagat aa                                                  22

<210> SEQ ID NO 22
<211> LENGTH: 11
<212> TYPE: DNA
<213> ORGANISM: Artificial Sequence
<220> FEATURE:
<223> OTHER INFORMATION: consensus DNA binding element of transcription
      factor B1

<400> SEQUENCE: 22
aarrggaary g                                                              11

<210> SEQ ID NO 23
<211> LENGTH: 30
<212> TYPE: DNA
<213> ORGANISM: Artificial Sequence
<220> FEATURE:
<223> OTHER INFORMATION: consensus DNA binding element of transcription
      factor BGP1

<400> SEQUENCE: 23
aattgcagag ctgggaatcg ggggggggggg                                         30

<210> SEQ ID NO 24
<211> LENGTH: 24
<212> TYPE: DNA
<213> ORGANISM: Artificial Sequence
<220> FEATURE:
<223> OTHER INFORMATION: consensus DNA binding element of transcription
      factor C/EBP

<400> SEQUENCE: 24
acaggatatc tgtggtaagc agtt                                                24

<210> SEQ ID NO 25
<211> LENGTH: 24
<212> TYPE: DNA
<213> ORGANISM: Artificial Sequence
<220> FEATURE:
<223> OTHER INFORMATION: consensus DNA binding element of transcription
      factor COUP

<400> SEQUENCE: 25 ccagggtca ggggggggt gctt                                                  24

<210> SEQ ID NO 26
```

```
<211> LENGTH: 25
<212> TYPE: DNA
<213> ORGANISM: Artificial Sequence
<220> FEATURE:
<223> OTHER INFORMATION: consensus DNA binding element of transcription
      factor CREB

<400> SEQUENCE: 26
cccatggccg tcatactgtg acgtc                                               25

<210> SEQ ID NO 27
<211> LENGTH: 18
<212> TYPE: DNA
<213> ORGANISM: Artificial Sequence
<220> FEATURE:
<223> OTHER INFORMATION: consensus DNA binding element of transcription
      factor CREB/ATF

<400> SEQUENCE: 27
ggctttcgtc acagggtg                                                       18

<210> SEQ ID NO 28
<211> LENGTH: 10
<212> TYPE: DNA
<213> ORGANISM: Artificial Sequence
<220> FEATURE:
<223> OTHER INFORMATION: consensus DNA binding element of transcription
      factor CTF

<400> SEQUENCE: 28
accccgccca                                                                10

<210> SEQ ID NO 29
<211> LENGTH: 15
<212> TYPE: DNA
<213> ORGANISM: Artificial Sequence
<220> FEATURE:
<223> OTHER INFORMATION: consensus DNA binding element of transcription
      factor CTF/CP1

<400> SEQUENCE: 29
gccaatgaca agacg                                                          15

<210> SEQ ID NO 30
<211> LENGTH: 17
<212> TYPE: DNA
<213> ORGANISM: Artificial Sequence
<220> FEATURE:
<223> OTHER INFORMATION: consensus DNA binding element of transcription
      factor CTF/NF-1

<400> SEQUENCE: 30
actggccagc agccaac                                                        17

<210> SEQ ID NO 31
<211> LENGTH: 22
<212> TYPE: DNA
<213> ORGANISM: Artificial Sequence
<220> FEATURE:
<223> OTHER INFORMATION: consensus DNA binding element of transcription
      factor CYP1

<400> SEQUENCE: 31
ctaatagcga taatagcgag gg                                                  22

<210> SEQ ID NO 32
<211> LENGTH: 15
```

```
<212> TYPE: DNA
<213> ORGANISM: Artificial Sequence
<220> FEATURE:
<223> OTHER INFORMATION: consensus DNA binding element of transcription
      factor DTF

<400> SEQUENCE: 32
aaaagaacat ctttt                                                          15

<210> SEQ ID NO 33
<211> LENGTH: 14
<212> TYPE: DNA
<213> ORGANISM: Artificial Sequence
<220> FEATURE:
<223> OTHER INFORMATION: consensus DNA binding element of transcription
      factor E2F

<400> SEQUENCE: 33
caattttcgc gcgg                                                           14

<210> SEQ ID NO 34
<211> LENGTH: 12
<212> TYPE: DNA
<213> ORGANISM: Artificial Sequence
<220> FEATURE:
<223> OTHER INFORMATION: consensus DNA binding element of transcription
      factor EBNA1

<400> SEQUENCE: 34
tagcatatgc ta                                                             12

<210> SEQ ID NO 35
<211> LENGTH: 10
<212> TYPE: DNA
<213> ORGANISM: Artificial Sequence
<220> FEATURE:
<223> OTHER INFORMATION: consensus DNA binding element of transcription
      factor EBP1

<400> SEQUENCE: 35
gggactttcc                                                                10

<210> SEQ ID NO 36
<211> LENGTH: 14
<212> TYPE: DNA
<213> ORGANISM: Artificial Sequence
<220> FEATURE:
<223> OTHER INFORMATION: consensus DNA binding element of transcription
      factor EF-1

<400> SEQUENCE: 36
caactgataa ggat                                                           14

<210> SEQ ID NO 37
<211> LENGTH: 26
<212> TYPE: DNA
<213> ORGANISM: Artificial Sequence
<220> FEATURE:
<223> OTHER INFORMATION: consensus DNA binding element of transcription
      factor EF-C

<400> SEQUENCE: 37
aagtgtttgc tgacgcaacc cccact                                              26

<210> SEQ ID NO 38
<211> LENGTH: 30
<212> TYPE: DNA
```

<213> ORGANISM: Artificial Sequence
<220> FEATURE:
<223> OTHER INFORMATION: consensus DNA binding element of transcription
      factor EFI

<400> SEQUENCE: 38
aagcaccgtg catgccgatt ggtggaagta                                    30

<210> SEQ ID NO 39
<211> LENGTH: 15
<212> TYPE: DNA
<213> ORGANISM: Artificial Sequence
<220> FEATURE:
<223> OTHER INFORMATION: consensus DNA binding element of transcription
      factor ETF

<400> SEQUENCE: 39
cagcccccgg cgcag                                                    15

<210> SEQ ID NO 40
<211> LENGTH: 10
<212> TYPE: DNA
<213> ORGANISM: Artificial Sequence
<220> FEATURE:
<223> OTHER INFORMATION: consensus DNA binding element of transcription
      factor ETFA

<400> SEQUENCE: 40
aactacgtca                                                          10

<210> SEQ ID NO 41
<211> LENGTH: 10
<212> TYPE: DNA
<213> ORGANISM: Artificial Sequence
<220> FEATURE:
<223> OTHER INFORMATION: consensus DNA binding element of transcription
      factor GATA-1

<400> SEQUENCE: 41
aagtatcact                                                          10

<210> SEQ ID NO 42
<211> LENGTH: 29
<212> TYPE: DNA
<213> ORGANISM: Artificial Sequence
<220> FEATURE:
<223> OTHER INFORMATION: consensus DNA binding element of transcription
      factor GC2

<400> SEQUENCE: 42
gagcttctaa attatccatc agcacaagc                                     29

<210> SEQ ID NO 43
<211> LENGTH: 30
<212> TYPE: DNA
<213> ORGANISM: Artificial Sequence
<220> FEATURE:
<223> OTHER INFORMATION: consensus DNA binding element of transcription
      factor GHF-1

<400> SEQUENCE: 43
cagtggcccc atgcataaat gtacacagaa                                    30

<210> SEQ ID NO 44
<211> LENGTH: 28
<212> TYPE: DNA
<213> ORGANISM: Artificial Sequence

```
<220> FEATURE:
<223> OTHER INFORMATION: consensus DNA binding element of transcription
      factor Gin

<400> SEQUENCE: 44
ttatccaaaa cctcggttta caggaaac                                              28

<210> SEQ ID NO 45
<211> LENGTH: 13
<212> TYPE: DNA
<213> ORGANISM: Artificial Sequence
<220> FEATURE:
<223> OTHER INFORMATION: consensus DNA binding element of transcription
      factor H2TFI

<400> SEQUENCE: 45
tggggattcc cca                                                              13

<210> SEQ ID NO 46
<211> LENGTH: 15
<212> TYPE: DNA
<213> ORGANISM: Artificial Sequence
<220> FEATURE:
<223> OTHER INFORMATION: consensus DNA binding element of transcription
      factor HAP

<400> SEQUENCE: 46
ctgcgaatgt tcgcg                                                            15

<210> SEQ ID NO 47
<211> LENGTH: 19
<212> TYPE: DNA
<213> ORGANISM: Artificial Sequence
<220> FEATURE:
<223> OTHER INFORMATION: consensus DNA binding element of transcription
      factor HAP1

<400> SEQUENCE: 47
aacctccgtt atctccatt                                                        19

<210> SEQ ID NO 48
<211> LENGTH: 12
<212> TYPE: DNA
<213> ORGANISM: Artificial Sequence
<220> FEATURE:
<223> OTHER INFORMATION: consensus DNA binding element of transcription
      factor HIVEN86A

<400> SEQUENCE: 48
ggggaatctc cc                                                               12

<210> SEQ ID NO 49
<211> LENGTH: 19
<212> TYPE: DNA
<213> ORGANISM: Artificial Sequence
<220> FEATURE:
<223> OTHER INFORMATION: consensus DNA binding element of transcription
      factor HNF-1

<400> SEQUENCE: 49
ctgtgaaata ttaactaaa                                                        19

<210> SEQ ID NO 50
<211> LENGTH: 27
<212> TYPE: DNA
<213> ORGANISM: Artificial Sequence
<220> FEATURE:
```

```
<223> OTHER INFORMATION: consensus DNA binding element of transcription
      factor HNF1

<400> SEQUENCE: 50
ccttggttaa tattcaccag cagcctc                                        27

<210> SEQ ID NO 51
<211> LENGTH: 30
<212> TYPE: DNA
<213> ORGANISM: Artificial Sequence
<220> FEATURE:
<223> OTHER INFORMATION: consensus DNA binding element of transcription
      factor HNFI

<400> SEQUENCE: 51
aacaaactgt caaatattaa ctaaagggag                                     30

<210> SEQ ID NO 52
<211> LENGTH: 24
<212> TYPE: DNA
<213> ORGANISM: Artificial Sequence
<220> FEATURE:
<223> OTHER INFORMATION: consensus DNA binding element of transcription
      factor HSTF

<400> SEQUENCE: 52
aaataaagaa tattctagaa tccc                                           24

<210> SEQ ID NO 53
<211> LENGTH: 30
<212> TYPE: DNA
<213> ORGANISM: Artificial Sequence
<220> FEATURE:
<223> OTHER INFORMATION: consensus DNA binding element of transcription
      factor ICP4

<400> SEQUENCE: 53
cggatgggcg gggccggggg ttcgaccaac                                     30

<210> SEQ ID NO 54
<211> LENGTH: 13
<212> TYPE: DNA
<213> ORGANISM: Artificial Sequence
<220> FEATURE:
<223> OTHER INFORMATION: consensus DNA binding element of transcription
      factor ICSBP

<400> SEQUENCE: 54
yrgtttcryt tyy                                                       13

<210> SEQ ID NO 55
<211> LENGTH: 12
<212> TYPE: DNA
<213> ORGANISM: Artificial Sequence
<220> FEATURE:
<223> OTHER INFORMATION: consensus DNA binding element of transcription
      factor ICSbf

<400> SEQUENCE: 55
agtttcactt ct                                                        12

<210> SEQ ID NO 56
<211> LENGTH: 15
<212> TYPE: DNA
<213> ORGANISM: Artificial Sequence
<220> FEATURE:
<223> OTHER INFORMATION: consensus DNA binding element of transcription
```

-continued factor ITF

<400> SEQUENCE: 56
gagaagtgaa agtgg                                                       15

<210> SEQ ID NO 57
<211> LENGTH: 30
<212> TYPE: DNA
<213> ORGANISM: Artificial Sequence
<220> FEATURE:
<223> OTHER INFORMATION: consensus DNA binding element of transcription
      factor IgPE-1

<400> SEQUENCE: 57
atatgggcca aacaggatat ctgtggtaag                                       30

<210> SEQ ID NO 58
<211> LENGTH: 21
<212> TYPE: DNA
<213> ORGANISM: Artificial Sequence
<220> FEATURE:
<223> OTHER INFORMATION: consensus DNA binding element of transcription
      factor IgPE-2

<400> SEQUENCE: 58
ccaccaaacc gaaagtccag g                                                21

<210> SEQ ID NO 59
<211> LENGTH: 25
<212> TYPE: DNA
<213> ORGANISM: Artificial Sequence
<220> FEATURE:
<223> OTHER INFORMATION: consensus DNA binding element of transcription
      factor IgPE-3

<400> SEQUENCE: 59
cctgggtaat ttgcatttct aaaat                                            25

<210> SEQ ID NO 60
<211> LENGTH: 11
<212> TYPE: DNA
<213> ORGANISM: Artificial Sequence
<220> FEATURE:
<223> OTHER INFORMATION: consensus DNA binding element of transcription
      factor KBF1

<400> SEQUENCE: 60
ggggattccc c                                                           11

<210> SEQ ID NO 61
<211> LENGTH: 30
<212> TYPE: DNA
<213> ORGANISM: Artificial Sequence
<220> FEATURE:
<223> OTHER INFORMATION: consensus DNA binding element of transcription
      factor LF-A1

<400> SEQUENCE: 61
cagatcccag ccagtggact tagcccctgt                                       30

<210> SEQ ID NO 62
<211> LENGTH: 12
<212> TYPE: DNA
<213> ORGANISM: Artificial Sequence
<220> FEATURE:
<223> OTHER INFORMATION: consensus DNA binding element of transcription
      factor LF-A2

```
<400> SEQUENCE: 62
ctccgataac tg                                                          12

<210> SEQ ID NO 63
<211> LENGTH: 23
<212> TYPE: DNA
<213> ORGANISM: Artificial Sequence
<220> FEATURE:
<223> OTHER INFORMATION: consensus DNA binding element of transcription
      factor LF-B1

<400> SEQUENCE: 63
accttggtta atattcacca gca                                              23

<210> SEQ ID NO 64
<211> LENGTH: 20
<212> TYPE: DNA
<213> ORGANISM: Artificial Sequence
<220> FEATURE:
<223> OTHER INFORMATION: consensus DNA binding element of transcription
      factor LF-B2

<400> SEQUENCE: 64
gggtgacctt ggttaatatt                                                  20

<210> SEQ ID NO 65
<211> LENGTH: 24
<212> TYPE: DNA
<213> ORGANISM: Artificial Sequence
<220> FEATURE:
<223> OTHER INFORMATION: consensus DNA binding element of transcription
      factor LF-C

<400> SEQUENCE: 65
tgcccctctg gatccactgc ttaa                                             24

<210> SEQ ID NO 66
<211> LENGTH: 16
<212> TYPE: DNA
<213> ORGANISM: Artificial Sequence
<220> FEATURE:
<223> OTHER INFORMATION: consensus DNA binding element of transcription
      factor MAT-alpha-1

<400> SEQUENCE: 66
atgtagaaaa gtacat                                                      16

<210> SEQ ID NO 67
<211> LENGTH: 16
<212> TYPE: DNA
<213> ORGANISM: Artificial Sequence
<220> FEATURE:
<223> OTHER INFORMATION: consensus DNA binding element of transcription
      factor MATa1

<400> SEQUENCE: 67
atgtgaatga atacat                                                      16

<210> SEQ ID NO 68
<211> LENGTH: 15
<212> TYPE: DNA
<213> ORGANISM: Artificial Sequence
<220> FEATURE:
<223> OTHER INFORMATION: consensus DNA binding element of transcription
      factor MBF-I
```

```
<400> SEQUENCE: 68
ttttgcacac ggcac                                                15

<210> SEQ ID NO 69
<211> LENGTH: 14
<212> TYPE: DNA
<213> ORGANISM: Artificial Sequence
<220> FEATURE:
<223> OTHER INFORMATION: consensus DNA binding element of transcription
      factor MCM1

<400> SEQUENCE: 69
ttcctaatta ggaa                                                 14

<210> SEQ ID NO 70
<211> LENGTH: 15
<212> TYPE: DNA
<213> ORGANISM: Artificial Sequence
<220> FEATURE:
<223> OTHER INFORMATION: consensus DNA binding element of transcription
      factor MEP-1

<400> SEQUENCE: 70
ctctgcactc cgccc                                                15

<210> SEQ ID NO 71
<211> LENGTH: 33
<212> TYPE: DNA
<213> ORGANISM: Artificial Sequence
<220> FEATURE:
<223> OTHER INFORMATION: an example of consensus DNA binding element of
      transcription factor MTF1
<220> FEATURE:
<221> NAME/KEY: misc_feature
<222> LOCATION: 3, 18
<223> OTHER INFORMATION: n = A,T,C or G
<220> FEATURE:
<221> NAME/KEY: misc_feature
<222> LOCATION: (4)...(12), (18)...(27)
<223> OTHER INFORMATION: n = A,T,C,G or absent

<400> SEQUENCE: 71
ctnnnnnnnn nntgcrcnnn nnnnnnncgg ccc                            33

<210> SEQ ID NO 72
<211> LENGTH: 10
<212> TYPE: DNA
<213> ORGANISM: Artificial Sequence
<220> FEATURE:
<223> OTHER INFORMATION: consensus DNA binding element of transcription
      factor NF-GMa

<400> SEQUENCE: 72
gagattccac                                                      10

<210> SEQ ID NO 73
<211> LENGTH: 22
<212> TYPE: DNA
<213> ORGANISM: Artificial Sequence
<220> FEATURE:
<223> OTHER INFORMATION: consensus DNA binding element of transcription
      factor NF-I

<400> SEQUENCE: 73
aaaaccttaa ataggtttag aa                                        22

<210> SEQ ID NO 74
```

```
<211> LENGTH: 20
<212> TYPE: DNA
<213> ORGANISM: Artificial Sequence
<220> FEATURE:
<223> OTHER INFORMATION: consensus DNA binding element of transcription
      factor NF-I/CTF

<400> SEQUENCE: 74
tagttggccc gctgccctgg                                                 20

<210> SEQ ID NO 75
<211> LENGTH: 10
<212> TYPE: DNA
<213> ORGANISM: Artificial Sequence
<220> FEATURE:
<223> OTHER INFORMATION: consensus DNA binding element of transcription
      factor NF-InsE1

<400> SEQUENCE: 75
ggccatcttg                                                            10

<210> SEQ ID NO 76
<211> LENGTH: 10
<212> TYPE: DNA
<213> ORGANISM: Artificial Sequence
<220> FEATURE:
<223> OTHER INFORMATION: consensus DNA binding element of transcription
      factor NF-InsE2

<400> SEQUENCE: 76
tgccagctgc                                                            10

<210> SEQ ID NO 77
<211> LENGTH: 10
<212> TYPE: DNA
<213> ORGANISM: Artificial Sequence
<220> FEATURE:
<223> OTHER INFORMATION: consensus DNA binding element of transcription
      factor NF-InsE3

<400> SEQUENCE: 77
tgccacatga                                                            10

<210> SEQ ID NO 78
<211> LENGTH: 20
<212> TYPE: DNA
<213> ORGANISM: Artificial Sequence
<220> FEATURE:
<223> OTHER INFORMATION: consensus DNA binding element of transcription
      factor NF-MHCIIA

<400> SEQUENCE: 78
gagtgatgac tcacgtcaag                                                 20

<210> SEQ ID NO 79
<211> LENGTH: 15
<212> TYPE: DNA
<213> ORGANISM: Artificial Sequence
<220> FEATURE:
<223> OTHER INFORMATION: consensus DNA binding element of transcription
      factor NF-MHCIIB

<400> SEQUENCE: 79
agaaccaatg ggcac                                                      15

<210> SEQ ID NO 80
<211> LENGTH: 14
```

```
<212> TYPE: DNA
<213> ORGANISM: Artificial Sequence
<220> FEATURE:
<223> OTHER INFORMATION: consensus DNA binding element of transcription
      factor NF-X

<400> SEQUENCE: 80
cctagcaaca gatg                                                         14

<210> SEQ ID NO 81
<211> LENGTH: 22
<212> TYPE: DNA
<213> ORGANISM: Artificial Sequence
<220> FEATURE:
<223> OTHER INFORMATION: consensus DNA binding element of transcription
      factor NF-Y

<400> SEQUENCE: 81
atttttctga ttggttaaaa gt                                                22

<210> SEQ ID NO 82
<211> LENGTH: 11
<212> TYPE: DNA
<213> ORGANISM: Artificial Sequence
<220> FEATURE:
<223> OTHER INFORMATION: consensus DNA binding element of transcription
      factor NF-kB

<400> SEQUENCE: 82
agggactttc c                                                            11

<210> SEQ ID NO 83
<211> LENGTH: 11
<212> TYPE: DNA
<213> ORGANISM: Artificial Sequence
<220> FEATURE:
<223> OTHER INFORMATION: consensus DNA binding element of transcription
      factor NF-kB/H2TF1

<400> SEQUENCE: 83
ggggaatccc c                                                            11

<210> SEQ ID NO 84
<211> LENGTH: 10
<212> TYPE: DNA
<213> ORGANISM: Artificial Sequence
<220> FEATURE:
<223> OTHER INFORMATION: consensus DNA binding element of transcription
      factor NF-uE2

<400> SEQUENCE: 84
agcagctggc                                                              10

<210> SEQ ID NO 85
<211> LENGTH: 15
<212> TYPE: DNA
<213> ORGANISM: Artificial Sequence
<220> FEATURE:
<223> OTHER INFORMATION: consensus DNA binding element of transcription
      factor NF-uE3

<400> SEQUENCE: 85
aggtcatgtg gcaag                                                        15

<210> SEQ ID NO 86
<211> LENGTH: 15
<212> TYPE: DNA
```

```
<213> ORGANISM: Artificial Sequence
<220> FEATURE:
<223> OTHER INFORMATION: consensus DNA binding element of transcription
      factor NFBK

<400> SEQUENCE: 86
gggaatgcag ccaaa                                                          15

<210> SEQ ID NO 87
<211> LENGTH: 17
<212> TYPE: DNA
<213> ORGANISM: Artificial Sequence
<220> FEATURE:
<223> OTHER INFORMATION: consensus DNA binding element of transcription
      factor NFI

<400> SEQUENCE: 87
acattctcct tgccaag                                                        17

<210> SEQ ID NO 88
<211> LENGTH: 12
<212> TYPE: DNA
<213> ORGANISM: Artificial Sequence
<220> FEATURE:
<223> OTHER INFORMATION: consensus DNA binding element of transcription
      factor Oct-1

<400> SEQUENCE: 88
aagtatgcaa ag                                                             12

<210> SEQ ID NO 89
<211> LENGTH: 43
<212> TYPE: DNA
<213> ORGANISM: Artificial Sequence
<220> FEATURE:
<223> OTHER INFORMATION: one example of consensus DNA binding element of
      transcription factor Oct-1/C1/C2
<220> FEATURE:
<221> NAME/KEY: misc_feature
<222> LOCATION: 6, 31
<223> OTHER INFORMATION: n = A,T,C or G
<220> FEATURE:
<221> NAME/KEY: misc_feature
<222> LOCATION: (7)...(15), (32)...(40)
<223> OTHER INFORMATION: n = A,T,C,G or absent

<400> SEQUENCE: 89
gyatgnnnnn nnnnntaatg arattcyttg nnnnnnnnnn ggg                           43

<210> SEQ ID NO 90
<211> LENGTH: 26
<212> TYPE: DNA
<213> ORGANISM: Artificial Sequence
<220> FEATURE:
<223> OTHER INFORMATION: consensus DNA binding element of transcription
      factor Oct-1/C1/a(prime)-TIF

<400> SEQUENCE: 90
gtgcatgcta atgatattct ttgggg                                              26

<210> SEQ ID NO 91
<211> LENGTH: 14
<212> TYPE: DNA
<213> ORGANISM: Artificial Sequence
<220> FEATURE:
<223> OTHER INFORMATION: consensus DNA binding element of transcription
      factor PEA1

<400> SEQUENCE: 91
```
gaagtgacta actg                                                         14

<210> SEQ ID NO 92
<211> LENGTH: 21
<212> TYPE: DNA
<213> ORGANISM: Artificial Sequence
<220> FEATURE:
<223> OTHER INFORMATION: consensus DNA binding element of transcription
      factor PEA2

<400> SEQUENCE: 92
actaactgac cgcagctggc c                                                 21

<210> SEQ ID NO 93
<211> LENGTH: 14
<212> TYPE: DNA
<213> ORGANISM: Artificial Sequence
<220> FEATURE:
<223> OTHER INFORMATION: consensus DNA binding element of transcription
      factor PEB1

<400> SEQUENCE: 93
cagagggcag tgtg                                                         14

<210> SEQ ID NO 94
<211> LENGTH: 21
<212> TYPE: DNA
<213> ORGANISM: Artificial Sequence
<220> FEATURE:
<223> OTHER INFORMATION: consensus DNA binding element of transcription
      factor RFX1

<400> SEQUENCE: 94
acccttcccc tagcaacaga t                                                 21

<210> SEQ ID NO 95
<211> LENGTH: 11
<212> TYPE: DNA
<213> ORGANISM: Artificial Sequence
<220> FEATURE:
<223> OTHER INFORMATION: consensus DNA binding element of transcription
      factor SBF-B

<400> SEQUENCE: 95
taaatataaa a                                                            11

<210> SEQ ID NO 96
<211> LENGTH: 11
<212> TYPE: DNA
<213> ORGANISM: Artificial Sequence
<220> FEATURE:
<223> OTHER INFORMATION: consensus DNA binding element of transcription
      factor SBF-E

<400> SEQUENCE: 96
atgggttttt g                                                            11

<210> SEQ ID NO 97
<211> LENGTH: 15
<212> TYPE: DNA
<213> ORGANISM: Artificial Sequence
<220> FEATURE:
<223> OTHER INFORMATION: consensus DNA binding element of transcription
      factor SCR-indf

<400> SEQUENCE: 97
cagttcccgt caatg                                                    15

<210> SEQ ID NO 98
<211> LENGTH: 30
<212> TYPE: DNA
<213> ORGANISM: Artificial Sequence
<220> FEATURE:
<223> OTHER INFORMATION: consensus DNA binding element of transcription
      factor STE7/12

<400> SEQUENCE: 98
gttagacgtt tcagcttcca aaacagaaga                                    30

<210> SEQ ID NO 99
<211> LENGTH: 13
<212> TYPE: DNA
<213> ORGANISM: Artificial Sequence
<220> FEATURE:
<223> OTHER INFORMATION: consensus DNA binding element of transcription
      factor Sp1/CRF

<400> SEQUENCE: 99
cgggcgggat tgg                                                      13

<210> SEQ ID NO 100
<211> LENGTH: 18
<212> TYPE: DNA
<213> ORGANISM: Artificial Sequence
<220> FEATURE:
<223> OTHER INFORMATION: consensus DNA binding element of transcription
      factor T3rec

<400> SEQUENCE: 100
aggtaagatc aggggacg                                                 18

<210> SEQ ID NO 101
<211> LENGTH: 15
<212> TYPE: DNA
<213> ORGANISM: Artificial Sequence
<220> FEATURE:
<223> OTHER INFORMATION: consensus DNA binding element of transcription
      factor TAB

<400> SEQUENCE: 101
tataaaagca gacgc                                                    15

<210> SEQ ID NO 102
<211> LENGTH: 19
<212> TYPE: DNA
<213> ORGANISM: Artificial Sequence
<220> FEATURE:
<223> OTHER INFORMATION: consensus DNA binding element of transcription
      factor TAF

<400> SEQUENCE: 102
tcgttttgta cgtttttca                                                19

<210> SEQ ID NO 103
<211> LENGTH: 12
<212> TYPE: DNA
<213> ORGANISM: Artificial Sequence
<220> FEATURE:
<223> OTHER INFORMATION: consensus DNA binding element of transcription
      factor TUF

<400> SEQUENCE: 103
aacatccgtg ca                                                       12

```
<210> SEQ ID NO 104
<211> LENGTH: 13
<212> TYPE: DNA
<213> ORGANISM: Artificial Sequence
<220> FEATURE:
<223> OTHER INFORMATION: consensus DNA binding element of transcription
      factor TyBF

<400> SEQUENCE: 104
gtcatcatag acg                                                          13

<210> SEQ ID NO 105
<211> LENGTH: 20
<212> TYPE: DNA
<213> ORGANISM: Artificial Sequence
<220> FEATURE:
<223> OTHER INFORMATION: consensus DNA binding element of transcription
      factor f-EBP

<400> SEQUENCE: 105
gatgtccata ttaggacatc                                                   20

<210> SEQ ID NO 106
<211> LENGTH: 51
<212> TYPE: DNA
<213> ORGANISM: Artificial Sequence
<220> FEATURE:
<223> OTHER INFORMATION: consensus DNA binding element of transcription
      factor uEBP-E
<220> FEATURE:
<221> NAME/KEY: misc_feature
<222> LOCATION: 2, 15, 26,  38,
<223> OTHER INFORMATION: n = A,T,C or G
<220> FEATURE:
<221> NAME/KEY: misc_feature
<222> LOCATION: (3)...(11), (16)...(24), (27)...(35), (39)...(47)
<223> OTHER INFORMATION: n = A,T,C,G or absent

<400> SEQUENCE: 106
tnnnnnnnnn nakynnnnnn nnnnknnnnn nnnnnmtnnn nnnnnnnatg a                51

<210> SEQ ID NO 107
<211> LENGTH: 14
<212> TYPE: DNA
<213> ORGANISM: Artificial Sequence
<220> FEATURE:
<223> OTHER INFORMATION: consensus DNA binding element of transcription
      factor x-box-bp

<400> SEQUENCE: 107
cctagcaaca gatg                                                         14

<210> SEQ ID NO 108
<211> LENGTH: 10
<212> TYPE: DNA
<213> ORGANISM: Artificial Sequence
<220> FEATURE:
<223> OTHER INFORMATION: consensus DNA binding element of transcription
      factor Sp-1

<400> SEQUENCE: 108
accccgccca                                                              10

<210> SEQ ID NO 109
<211> LENGTH: 12
<212> TYPE: DNA
<213> ORGANISM: Artificial Sequence
```

-continued

```
<220> FEATURE:
<223> OTHER INFORMATION: consensus DNA binding element of transcription
      factor c-Myc

<400> SEQUENCE: 109
raccacgtgc tc                                                            12
```